US011292833B2

(12) United States Patent
Heitzmann et al.

(10) Patent No.: US 11,292,833 B2
(45) Date of Patent: Apr. 5, 2022

(54) SELECTIVE REDUCTION OF CYSTEINE RESIDUES IN IL-17 ANTIBODIES

(71) Applicant: Novartis AG, Basel (CH)

(72) Inventors: Markus Heitzmann, Lörrach (DE); Johann Winkler, Kiefersfelden (DE)

(73) Assignee: NOVARTIS AG, Basel (CH)

( * ) Notice: Subject to any disclaimer, the term of this patent is extended or adjusted under 35 U.S.C. 154(b) by 393 days.

(21) Appl. No.: 15/538,266

(22) PCT Filed: Dec. 21, 2015

(86) PCT No.: PCT/IB2015/059824
§ 371 (c)(1),
(2) Date: Jun. 21, 2017

(87) PCT Pub. No.: WO2016/103146
PCT Pub. Date: Jun. 30, 2016

(65) Prior Publication Data
US 2017/0369567 A1    Dec. 28, 2017

Related U.S. Application Data

(60) Provisional application No. 62/095,361, filed on Dec. 22, 2014.

(51) Int. Cl.
*C07K 16/24* (2006.01)

(52) U.S. Cl.
CPC ........ *C07K 16/244* (2013.01); *C07K 2317/14* (2013.01); *C07K 2317/21* (2013.01); *C07K 2317/24* (2013.01); *C07K 2317/40* (2013.01); *C07K 2317/565* (2013.01); *C07K 2317/76* (2013.01)

(58) Field of Classification Search
CPC ... C07K 2317/76; C07K 16/24; A61K 39/395
See application file for complete search history.

(56) References Cited

U.S. PATENT DOCUMENTS

| | | | |
|---|---|---|---|
| 6,331,415 | B1 | 12/2001 | Cabilly et al. |
| 7,807,155 | B2 | 10/2010 | Di Padova et al. |
| 7,923,221 | B1 | 4/2011 | Cabilly et al. |
| 7,928,205 | B2 | 4/2011 | Dillon et al. |
| 8,378,073 | B2 | 2/2013 | Heywood |
| 2005/0123532 | A1 | 6/2005 | Kouno et al. |
| 2006/0194280 | A1 | 8/2006 | Dillon et al. |
| 2006/0257393 | A1 | 11/2006 | Sasaki et al. |
| 2012/0353962 | | 7/2012 | Hashizume et al. |
| 2013/0202610 | A1 | 8/2013 | Guettner et al. |

FOREIGN PATENT DOCUMENTS

| | | |
|---|---|---|
| CN | 101212984 A | 7/2007 |
| CN | 104011223 A | 8/2014 |
| EP | 2360170 A2 | 8/2011 |
| EP | 2896404 B1 | 8/2017 |
| JP | 2008507988 A | 8/2005 |
| JP | 2008520190 A | 10/2005 |
| JP | 2008-507988 A | 3/2008 |
| JP | 2008520190 A | 6/2008 |
| JP | 2014530891 A | 10/2012 |
| JP | 2014-530891 A | 11/2014 |
| WO | WO2006/013107 A1 | 2/2006 |
| WO | 2009092011 A1 | 7/2009 |
| WO | 2011061492 A2 | 5/2011 |
| WO | 2013077907 A1 | 5/2013 |

OTHER PUBLICATIONS

Third Party Observations filed in counterpart EP15823803 on Feb. 19, 2020.
Reference 'Rapporteur day 80 Critical Assessment Report', filed Nov. 18, 2019 by third party in counterpart EP15823803.
Reference 'Jeschke', filed Nov. 18, 2019 by third party in counterpart EP15823803.
Reference 'Banks et al', filed Nov. 18, 2019 by third party in counterpart EP15823803.
Reference 'Lewis et al', filed Nov. 18, 2019 by third party in counterpart EP15823803.
Reference 'Trexler-Schmidt et al', filed Nov. 18, 2019 by third party in counterpart EP15823803.
Buchanan et al., "Engineering a therapeutic IgG molecule to address cysteinylation, aggregations and enhance thermal stability and expression". MABS, 2013, vol. 5, No. 2, pp. 255-262.
Gosrrez et al., "Effect of Temperature, pH, Dissolved Oxygen, and Hydrolysate on the Formation of Triple Light Chain Antibodies in Cell Culture", Biotechnology Progress, 2010, vol. 26, No. 5, pp. 1438-1445.
Badino et al. (2001) Biochemical Engineering Journal 8:111-119
Banks et al. (2008) Journal of Pharmaceutical Sciences, 97(2) 764-789.
Garcia Ochoa and Gomez (2009) Biotechnology Advances 27:153-176.

(Continued)

*Primary Examiner* — Dong Jiang
(74) *Attorney, Agent, or Firm* — David Goetz

(57) ABSTRACT

The present disclosure relates to methods for selectively reducing CysL97 in a preparation of IL-17 antibodies or antigen binding fragments thereof (e.g., a preparation of secukinumab antibodies) that have been recombinantly produced by mammalian cells. Also provided are purified preparations of IL-17 antibodies or antigen binding fragments thereof produced by such methods, e.g, purified preparations of secukinumab, wherein the level of intact IL-17 antibodies or antigen binding fragments thereof (e.g., secukinumab) in the preparation is high, e.g., at least about 90%, as measured by sodium dodecyl sulfate capillary electrophoresis (CE-SDS), and wherein the level of activity of IL-17 antibodies or antigen binding fragments thereof (e.g., secukinumab) in the preparation is high, e.g., at least about 92%, as measured by cation exchange chromatograph (CEX).

25 Claims, 21 Drawing Sheets
Specification includes a Sequence Listing.

(56) References Cited

OTHER PUBLICATIONS

Brody, T. (1997) Analytical Biochemistry 247:247-256.
Gosh and Ganguli (1934) Biochem J. 28:381-383.
Green (1933) Biochem J. 27(3):678-689.
Harrison and Quastel (1928) Biochem J. 22(3): 683-688.
Jocelyn, P. (1967) European J. Biochem. 2:327-331.
Juarez and Orejas (2001) Latin American Applied Research 31:433-439.
Petersen and Dorrington (1974) J. Biol. Chem 249(17):5633-5641.
Trexler Schmidt et al. (2010) Biotechnology and Bioengineering 106(3):452-461.
Sears et al. (1977) Biochemistry 16(9) 2031-2035.
Yang and Wang (1992) Biotechnol. Prog. 8:244-251.
Ohtsuki et al. (2014) Journal of Dermatology 41:1039-1046.
Langley, R et al. Poster presented at the 22nd Congress of the EADV; Oct. 2-6, 2013; Istanbul, Turkey.
Mrowietz U et al. Poster presented at the 22nd Congress of the EADV; Oct. 2-6, 2013; Istanbul, Turkey.
Papp et. a. (2013) British Association of Dermatologists 168:412-421.
Rich et al. (2013) British Association of Dermatologists 168:402-411.
Langley et al. (2014) N Engl J Med 371:326-38.
Jancin (2013) Skin & Allergy News Digital Network, available at: http://www.skinandallergynews.com.
Hueber et al. (2012) Gut 61:1693-1700.
Hueber et al. (2010) Sci Transl Med 2, 52ra72.
"Rapporteurs Day 80 critical assessment report: non-clinical aspects, Cosentyx, secukinumab, EMEA/H/C3729", European Medicines Agency, dated Feb. 7, 2014.
"Rapporteurs Day 80 critical assessment report: overview and list of questions, Cosentyx, secukinumab, EMEA/H/C3729", European Medicines Agency, dated Feb. 7, 2014.
Adami et al., Abstract 501, 2013 ACR/ARHP Annual Meeting, Oct. 25-30, 2013, San Diego, CA.
Burmester et al., Abstract 1737, 2013 ACR/ARHP Annual Meeting, Oct. 25-30, 2013, San Diego, CA.
Dick et al. (2013) Ophthalmology 120:777-787 Elewski et. al. Abstract P7969 and Gottlieb et al. Abstract P9738, JAAD May 2014, vol. 70, Issue 5, Supplement 1, p. AB189.
Genovese et al. (2013) Ann Rheum Dis 72:863-869.
Gottlieb et al. (2014) AB0738, Annals of the Rheumatic Diseases 73:1047-1048.
Gottlieb et al. Abstract 319, 2013 ACR/ARHP Annual Meeting, Oct. 25-30, 2013, San Diego, CA.
Gottlieb et al. Abstract L7, 2013 ACR/ARHP Annual Meeting, Oct. 25-30, 2013, San Diego, CA.
Mullan, B.,et al, "Disulphide Bond Reduction of a Therapeutic Monoclonal Antibody During Cell Culture Manufacturing Operations" BMC Proc 5, 2011, Article 110, pp. 1-3 https://doi.org/10.1186/1753-6561-5-S8-P110.
Liu, H, "In Vitro and In Vivo Modifications of Recombinant and Human IgG Antibodies," mAbs, 6:5, Oct. 30, 2014 (Oct. 30, 2014), pp. 1145-1154, https://doi.org/10.4161/mabs.29883.
Gevondyan, N.M. et al., Four Free Cysteine Residues are Normally Found in Human IgG1, Biochemistry, 2006, vol. 71, No. 3, pp. 353-360.
Lewis, R. ,et al, "Summary of DIA Workshop: Comparability Challenges: Regulatory and Scientific Issues in the Assessment of Biopharmaceuticals", Drug Information Journal, Feb. 3, 2010 (Feb. 3, 2010), vol. 44, pp. 485-504.
ClinicalTrials.gov, NCT01365455, [retrieved on Jan. 22, 2021], Retrieved from the Internet, URL, <https://clinicaltrials.gov/ct2/show/study/NCT01365455>, pp. 1-10.
ClinicalTrials.gov, NCT01358578, [retrieved on Jan. 22, 2021], Retrieved from the Internet, URL, <https://clinicaltrials.gov/ct2/show/study/NCT01358578>, pp. 1-8.
Report on the Deliberation Results, Evaluation and Licensing Division, Pharmaceutical and Food Safety Bureau, Ministry of Health, Labour and Welfare, (Dec. 3, 2014), front page, pp. 1-90 (English and Japanese languages).
WHO Drug Information, 24(3):259-260 and 278-279 (2010).
Analytical comparability of a human IgG1 from different manufacturing sites after cell line switch and process changes: A case study, DIA conference, Feb. 4, 2009.
Hutterer, K. et al., "Monoclonal Antibody Disulfide Reduction During Manufacturing," mAbs, 5(4), pp. 608-613, Jul. 1, 2013.

SELECTIVE REDUCTION OF CYSTEINE RESIDUES IN IL-17 ANTIBODIES

RELATED APPLICATIONS

This application claims priority to U.S. Provisional Patent Application No. 62/095,361, filed on Dec. 22, 2014, which is incorporated by reference herein in its entirety.

TECHNICAL FIELD

The present disclosure relates to methods for selectively reducing CysL97 in a preparation of IL-17 antibodies or antigen binding fragments thereof, e.g., a preparation of secukinumab, that have been recombinantly produced by mammalian cells.

BACKGROUND OF THE DISCLOSURE

Classical antibodies are composed of two light chains (L) with a molecular weight of about 25 kD each and two heavy chains (H) with a molecular weight of about 50 kD each. The light and heavy chains are connected by a disulfide bond (L-S—S—H) and the two LH units are further linked between the heavy chains by two disulfide bonds. The general formula of a classical antibody is L-SS—H(—SS—)$_2$H—SS-L or simply H$_2$L$_2$ (HHLL). Besides these conserved inter-chain disulfide bonds, there are also conserved intra-chain disulfide. Both types of disulfide bonds are important for the stability and behavior (e.g., affinity) of an antibody. Generally, a disulfide bond is produced by two cysteine residues (Cys-SH) found at conserved positions in the antibody chains, which spontaneously form the disulfide bond (Cys-S—S-Cys). Disulfide bonds formation is determined by the redox potential of the environment and by the presence of enzymes specialized in thiol-disulfide exchange. The internal disulfide bonds (Cys-S—S-Cys) stabilize the three-dimensional structure of an antibody.

There are unusual antibodies that contain an additional free cysteine(s) (i.e., unpaired cysteine) that is involved in antigen recognition and binding. For these antibodies, modification of a free cysteine can have a negative effect on the activity and stability of the molecule, and can lead to increased immunogenicity. As a result, processing of these antibodies can be difficult, as the end product may contain a substantial amount of inactive, misfolded and useless antibody material. US20090280131, which is incorporated by reference herein in its entirety, provides IL-17 antibodies, e.g., secukinumab (i.e., AIN457) with a free cysteine residue after the cis-proline in the light chain complementarity determining region (CDR) 3 loop (L-CDR3) (i.e., amino acid eight of L-CDR3 as set forth as SEQ ID NO:6, which corresponds to amino acid 97 of the light chain variable region as set forth as SEQ ID NO:10, herein after referred to as "CysL97"). In order to maintain full activity, the unpaired cysteine residue of secukinuamb cannot be masked by oxidative disulfide pairing with other cysteine residues or by oxidation with exogenous compounds (e.g., formation of mixed disulfides with other proteins, derivatization with cell metabolites [e.g., cysteine or glutathione], and formation of sulfoxides by oxygen). Unfortunately, because secukinuamb is manufactured using mammalian cells, undesired cell-based modifications of CysL97 do occur.

The literature describes refolding of mammalian proteins expressed in bacterial cells, which produce mammalian proteins as unfolded, insoluble aggregates having mixed disulfides (inclusion bodies). To obtain mammalian proteins from bacteria, inclusion body proteins are isolated, solubilized, and denatured with strong chaotropic reagents and reducing agents. Complete denaturation and reduction of disulfide bonds using a denaturing agent, reducing agent, disulfide adduct forming agent, and a mild oxidizing/reducing environment (pH 7-9) has also been used to properly refold plant proteins obtained from commercial sources or recombinantly produced in yeast (U.S. Pat. No. 4,766,205). These processes, which employ complete denaturation and refolding of proteins, are expensive, caustic, time-consuming, and unnecessary for a protein produced in mammalian cells.

The use of reduction/oxidation coupling reagents to correct misfolding of non-naturally occurring Fc fusion proteins is known (WO02/68455). The Fc fusion proteins of WO02/68455 presumably contain interchain disulfides in the Fc region that are reduced and reoxidized by the disclosed process, but there is no teaching therein of how to produce a molecule having a selectively reduced cysteine residue. Moreover, an Fc fusion protein is simply not an antibody, a highly complex immunoglobulin that relies on numerous properly linked inter-chain and intra-chain disulfides for structure and activity.

US20050123532 provides methods of producing an antibody having a free cysteine by activating the antibody with a reducing agent, or by culturing the antibody-producing cells in a serum-free medium supplemented with L-cysteine. When using this cell-culture method, later processing steps, e.g., filtration, viral inactivation and chromatography, could lead to oxidation of the free cysteine produced by cell-culture methods. In such cases, the free cysteine is ideally protected during later steps by modifying the free thiol group with an oxidizing agent, which is itself later removed using various techniques, e.g., filtration (US20060257393). For commercial production, such methods require large quantities of reducing agent in the original culture medium, large quantities of an oxidizing agent during later processing, and additional filtration methods to remove the oxidizing agent, adding time and expense to the cost of production.

U.S. Pat. No. 7,928,205 teaches a preference for using redox pairs for refolding IgG$_2$ antibodies obtained from mammalian cell cultures, as well as methods for decysteinylation of a free cysteine in the variable region of the 146B7 (IgG$_1$) antibody. The corresponding research publication, Banks et al. (2008) J. Pharmaceutical Sci. 97:764-779, teaches decysteinylation of an unpaired sulfhydryl in the variable region of a recombinant monoclonal IgG$_1$ antibody (MAB007). Banks et al. studied whether decysteinylation of MAB007 required the use of a strong denaturant (GdnHCL) and a reducing agent (cysteine) or whether selective reduction could occur in the presence of cysteine alone. The authors determined that cysteinylation was effectively removed from MAB007 in the presence and absence of denaturant.

None of the above references teach whether selective reduction of CysL97 in secukinumab is possible. Nor do the above references teach the reagents and conditions necessary for selective reduction of CysL97 in secukinumab, which depend upon, inter alia, the primary, secondary and tertiary structure of secukinumab; the position and location of oxidized CysL97 in secukinumab (e.g., solvent-accessible or inaccessible); and the relative strength of the conserved disulfide bonds in the antibody (e.g., whether CysL97 reacts first with a given reducing agent, or only after conserved cysteines have been reduced). Moreover, none of these references describe whether selective reduction of oxidized CysL97 in secukinumab would result in changes to the antibody structure (e.g., folding), chemical composition (e.g., deamidation), or properties (binding activity, propensity to aggregate or degrade), all of which could make it technically unfeasible/impractical to selective reduce secukinumab at commercial scale.

SUMMARY OF THE DISCLOSURE

In order to maintain maximal secukinumab antigen-binding activity, we have determined that it is necessary during processing of secukinumab to convert CysL97 from masked (1) to free (2) form (see I, below) without significant reduction of the conserved disulfide bonds; otherwise lower activity and inactive lower molecular weight variants will form by chain unlinking ($H_2L_2 \rightarrow H_2L$, $HL_2$, HL, H and L).

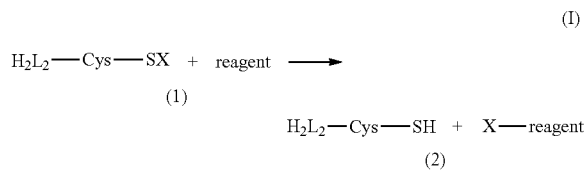

(I)

Introducing reducing conditions during commercial scale antibody preparation is counterintuitive (see, e.g., Trexler-Schmidt et al. 2010 Biotech and Bioengineering 106:452-61, which employs various reagents and methods to prevent antibody disulfide bond reduction during cell culture manufacturing of antibodies). Nevertheless, we have determined that it is possible to selectively reduce CysL97 in secukinumab during large scale commercial production in mammalian cells without significant denaturation of the antibody. Disclosed herein are methods for selectively reducing CysL97 in the antigen binding sites of the IL-17 antibodies (and fragments thereof) disclosed in US20090280131, particularly secukinumab. These methods assist in restoring the binding activity of these antibodies, and thus increase the bioactivity of preparations thereof. Furthermore, these methods assist in increasing the level of intact antibody and enhancing the homogeneity of preparations of these antibodies. The disclosed processes rely on the combined effect of particular ratios of antibody:reductant and controlled oxygen transfer rates in the system during incubation.

Accordingly, disclosed herein are methods for selectively reducing CysL97 in a preparation of IL-17 antibodies that have been recombinantly produced by mammalian cells, comprising:
a) contacting the preparation with at least one reducing agent in a system to form a reducing mixture; and
b) incubating the reducing mixture while maintaining a volumetric oxygen mass-transfer coefficient ($k_La^*$) in the system of ≤about 0.37 h$^{-1}$, said $k_La^*$ being calculated by adapting a dissolved oxygen curve to a saturation curve;
wherein the IL-17 antibodies each comprise an immunoglobulin heavy chain variable domain ($V_H$) comprising the three complementarity determining regions (CDRs) of the $V_H$ set forth as SEQ ID NO:8 and an immunoglobulin light chain variable domain ($V_L$) comprising the three CDRs of the $V_L$ set forth as SEQ ID NO:10, and further wherein prior to step a) the initial percent oxygen saturation in the preparation is at least about 60%, as measured using an oxygen probe calibrated at 25° C.

Also disclosed herein are methods for selectively reducing CysL97 in a preparation of IL-17 antibodies that have been recombinantly produced by mammalian cells, comprising:
a) contacting the preparation with a set of oxidation/reduction reagents selected from cysteine/cysteine and cysteine/cystamine to form a reducing mixture; and
b) incubating the reducing mixture at a temperature of about 37° C. under anaerobic conditions for at least about 4 hours, or incubating the reducing mixture at a temperature of about 18-24° C. for about 16-24 hours;
wherein the IL-17 antibodies each comprise an immunoglobulin heavy chain variable domain ($V_H$) comprising the three complementarity determining regions (CDRs) of the $V_H$ set forth as SEQ ID NO:8 and an immunoglobulin light chain variable domain ($V_L$) comprising the three CDRs of the $V_L$ set forth as SEQ ID NO:10.

Also disclosed herein are also purified preparations of secukinumab, wherein the level of intact secukinumab in the preparation is at least about 90%, as measured by sodium dodecyl sulfate capillary electrophoresis (CE-SDS), and wherein the level of activity of secukinumab in the preparation is at least about 90%, as measured by cystamine-CEX.

DETAILED DESCRIPTION OF THE DISCLOSURE

Figure 1:
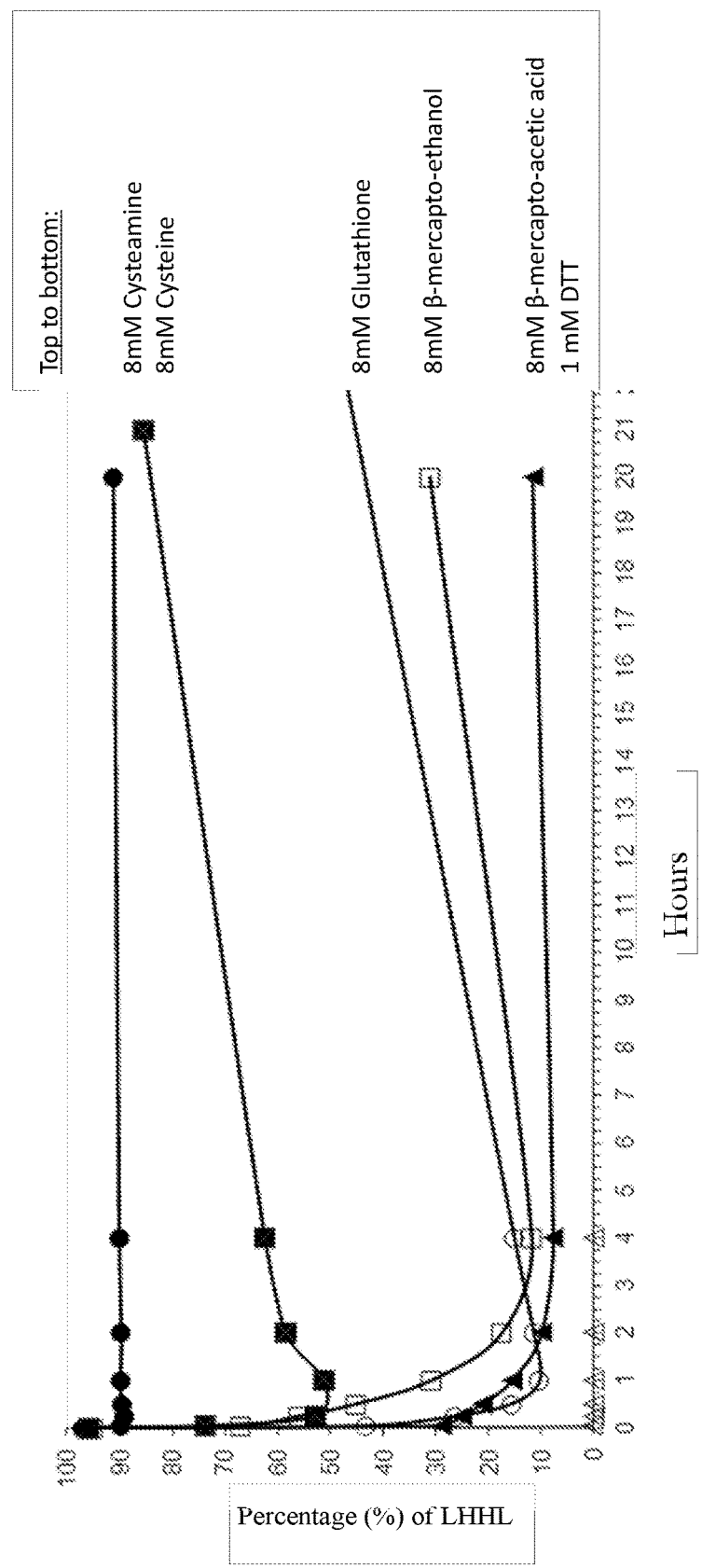
FIG. 1 shows the percentage of intact antibody (LHHL) over time after subjection to different reducing agents.

It is an object of the disclosure to provide methods for selectively reducing CysL97 in the antigen binding sites of certain IL-17 antibodies or antigen binding fragments thereof, such as secukinumab. By "selectively reducing" is meant that CysL97 in a disclosed IL-17 antibody or antigen binding fragment thereof is reduced to an oxidized form without reduction of the conserved cysteine residues of these antibodies. The conserved cysteine residues, in the case of a classical IgG$_1$ antibody, are: two disulfide bridges in the hinge region, two inter-chain disulfide bridges (one in each Fab), four intra-chain disulfide bridges in the Fc region, and eight intra-chain disulfide bridges in the Fab portion of the antibody. During the selective reduction process, transient reduction of the conserved cysteines of some antibodies in a particular preparation may occur. However, upon completion of the reaction, the vast majority of the conserved cysteines that were transiently reduced will have reoxidized to form the conserved disulfide bonds found in typical antibodies, resulting in high purity and activity in the selectively reduced preparation (i.e., purified preparation) of antibodies. It will be understood that upon completion of the selective reduction reaction, the selectively reduced preparation (i.e., purified preparation) is not expected to contain 100% intact antibodies; instead the selectively reduced preparation will ideally contain at least about 80, 81, 82, 83, 84, 85, 86, 87, 88, 89, 90, 91, 92, 93 94, 95, 96, 97, 98, 99, or about 100% (relative to theoretical maximum), intact antibodies as measured by CE-SDS.

The term "comprising" encompasses "including" as well as "consisting" e.g. a composition "comprising" X may consist exclusively of X or may include something additional e.g. X+Y.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The relative molecular mass of secukinumab, based on post-translational amino acid sequence, is 147,944 Daltons. This molecular weight (i.e., 147,944 Daltons) is used in the calculation of secukinumab molarity values and molar ratios throughout the instant disclosure. However, during production in CHO cells, a C-terminal lysine is commonly removed from each heavy chain. The relative molecular mass of secukinumab lacking a C-terminal lysine from each heavy chain is 147,688 Daltons. A preparation of secukinumab contains a mixture of molecules with and without C-terminal lysine residues on the heavy chain. The secukinumab molarity values (and ratios employing these molarity values) used in the instant disclosure are therefore estimates, and the term "about", "approximate" and the like in reference to these numerical values encompasses at least this variation in relative molecular mass and the resulting calculations made therewith.

The word "substantially" does not exclude "completely" e.g. a composition which is "substantially free" from Y may be completely free from Y. Where necessary, the word "substantially" may be omitted from the definition of the disclosure.

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "antigen-binding fragment" of an antibody as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen binding sites include the CDRs of secukinumab as set forth in SEQ ID NOs:1-6 and 11-13 (Table 1), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art.

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed processes and compositions, the IL-17 antibody is a human antibody, an isolated antibody, and/or a monoclonal antibody.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. In some embodiments, the IL-17 antibody or antigen binding fragment, e.g., secukinumab, has a $K_D$ of about 100-250 pM for humanIL-17.

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore analysis.

An antibody that "inhibits" one or more of these IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least about 10% of the measured parameter, by at least 50%, 80% or 90%, and in certain embodiments of the disclosed methods and compositions, the IL-17 antibody used may inhibit greater than 95%, 98% or 99% of IL-17 functional activity.

"Inhibit IL-6" as used herein refers to the ability of an IL-17 antibody or antigen binding fragment thereof (e.g., secukinumab) to decrease IL-6 production from primary human dermal fibroblasts. The production of IL-6 in primary human (dermal) fibroblasts is dependent on IL-17 (Hwang et al., (2004) Arthritis Res Ther; 6:R120-128). In short, human dermal fibroblasts are stimulated with recombinant IL-17 in the presence of various concentrations of an IL-17 binding molecule or human IL-17 receptor with Fc part. The chimeric anti-CD25 antibody Simulect® (basiliximab) may be conveniently used as a negative control. Supernatant is taken after 16 h stimulation and assayed for IL-6 by ELISA. An IL-17 antibody or antigen binding fragment thereof, e.g., secukinumab, typically has an $IC_{50}$ for inhibition of IL-6 production (in the presence 1 nM human IL-17) of about 50 nM or less (e.g., from about 0.01 to about 50 nM) when tested as above, i.e., said inhibitory activity being measured on IL-6 production induced by hu-IL-17 in human dermal fibroblasts. In some embodiments of the disclosed methods and compositions, IL-17 antibodies or antigen binding fragments thereof, e.g., secukinumab, and functional derivatives thereof have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

The term "derivative", unless otherwise indicated, is used to define amino acid sequence variants, and covalent modifications (e.g., pegylation, deamidation, hydroxylation, phosphorylation, methylation, etc.) of an IL-17 antibody or antigen binding fragment thereof, e.g., secukinumab, according to the present disclosure, e.g., of a specified sequence (e.g., a variable domain). A "functional derivative" includes a molecule having a qualitative biological activity in common with the disclosed IL-17 antibodies. A functional derivative includes fragments and peptide analogs of an IL-17 antibody as disclosed herein. Fragments comprise regions within the sequence of a polypeptide according to the present disclosure, e.g., of a specified sequence. Functional derivatives of the IL-17 antibodies disclosed herein (e.g., functional derivatives of secukinumab) preferably comprise $V_H$ and/or $V_L$ domains having at least about 65%, 75%, 85%, 95%, 96%, 97%, 98%, or 99% overall sequence identity with the $V_H$ and/or $V_L$ sequences of the IL-17 antibodies and antigen binding fragments thereof disclosed herein (e.g., the $V_H$ and/or $V_L$ sequences of Table 1), and substantially retain the ability to bind human IL-17 or, e.g., inhibit IL-6 production of IL-17 induced human dermal fibroblasts.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this application. In some embodiments, the sequence identity of a derivative IL-17 antibody (e.g., a derivative of secukinumab, e.g., a secukinumab biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of an antibody according to the present disclosure, e.g., of a specified sequence, still have the ability to bind the human IL-17 or, e.g., inhibit IL-6 production of IL-17 induced human dermal fibroblasts. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The phrases "free cysteine", "non-traditional cysteine" and "unpaired cysteine" interchangeably refer to a cysteine that is not involved in conserved antibody disulfide bonding. The free cysteine may be present in an antibody framework region or a variable region (e.g., within a CDR). In secukinumab, amino acid eight of L-CDR3 as set forth as SEQ ID NO:6, which corresponds to amino acid 97 of the light chain variable region as set forth as SEQ ID NO:10 (herein after referred to as CysL97) is a free cysteine. Each molecule of secukinumab comprises two such free cysteine residues—one in each $V_L$ domain. The disclosed processes are capable of selectively reducing both free cysteine residues in secukinumab. In some embodiments, e.g., due to deletions and/or substitutions in the light chain of a disclosed IL-17 antibody or antigen binding fragment thereof, the free cysteine will not be present at position CysL97. In such case, the corresponding free cysteine is the target of the selective reduction reaction and is included within the term "CysL97".

IL-17 Antibodies and Antigen Binding Fragments Thereof

The various disclosed processes and relate to the selective reduction of certain IL-17 antibodies or antigen binding fragments thereof (e.g., secukinumab). In one embodiment, the IL-17 antibody or antigen binding fragment thereof comprises at least one immunoglobulin heavy chain variable domain ($V_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-17 antibody or antigen binding fragment thereof comprises at least one immunoglobulin light chain variable domain ($V_L$) comprising hypervariable regions CDR1', CDR2' and CDR3', said CDR1' having the amino acid sequence SEQ ID NO:4, said CDR2' having the amino acid sequence SEQ ID NO:5 and said CDR3' having the amino acid sequence SEQ ID NO:6. In one embodiment, the IL-17 antibody or antigen binding fragment thereof comprises at least one immunoglobulin heavy chain variable domain ($V_H$) comprising hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13.

In one embodiment, the IL-17 antibody or antigen binding fragment thereof comprises at least one immunoglobulin $V_H$ domain and at least one immunoglobulin $V_L$ domain, wherein: a) the $V_H$ domain comprises (e.g., in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the $V_L$ domain comprises (e.g., in sequence) hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen binding fragment thereof comprises: a) an immunoglobulin heavy chain variable domain ($V_H$) comprising the amino acid sequence set forth as SEQ ID NO:8; b) an immunoglobulin light chain variable domain ($V_L$) comprising the amino acid sequence set forth as SEQ ID NO:10; c) an immunoglobulin $V_H$ domain comprising the amino acid sequence set forth as SEQ ID NO:8 and an immunoglobulin $V_L$ domain comprising the amino acid sequence set forth as SEQ ID NO:10; d) an immunoglobulin $V_H$ domain comprising the hypervariable regions set forth as SEQ ID NO:1, SEQ ID NO:2, and SEQ ID NO:3; e) an immunoglobulin $V_L$ domain comprising the hypervariable regions set forth as SEQ ID NO:4, SEQ ID NO:5 and SEQ ID NO:6; f) an immunoglobulin $V_H$ domain comprising the hypervariable regions set forth as SEQ ID NO:11, SEQ ID NO:12 and SEQ ID NO:13; g) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; or h) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

For ease of reference the amino acid sequences of the hypervariable regions of the secukinumab monoclonal antibody, based on the Kabat definition and as determined by the X-ray analysis and using the approach of Chothia and coworkers, is provided in Table 1, below.

ID NO:15 (with or without the C-terminal lysine). In other embodiments, the IL-17 antibody or antigen binding fragment thereof comprises the light chain of SEQ ID NO:14 and the heavy chain of SEQ ID NO:15 (with or without the C-terminal lysine). In some embodiments, the IL-17 antibody or antigen binding fragment thereof comprises the three CDRs of SEQ ID NO:14. In other embodiments, IL-17 antibody or antigen binding fragment thereof comprises the three CDRs of SEQ ID NO:15. In other embodiments, the IL-17 antibody or antigen binding fragment thereof comprises the three CDRs of SEQ ID NO:14 and the three CDRs of SEQ ID NO:15. CDRs of SEQ ID NO:14 and SEQ ID NO:15 may be found in Table 1.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another

TABLE 1

Amino acid sequences of the hypervariable regions of the secukinumab monoclonal antibodies.

Light-Chain

| | | |
|---|---|---|
| CDR1' | Kabat | R-A-S-Q-S-V-S-S-S-Y-L-A (SEQ ID NO: 4) |
| | Chothia | R-A-S-Q-S-V-S-S-S-Y-L-A (SEQ ID NO: 4) |
| CDR2' | Kabat | G-A-S-S-R-A-T (SEQ ID NO: 5) |
| | Chothia | G-A-S-S-R-A-T (SEQ ID NO: 5) |
| CDR2' | Kabat | Q-Q-Y-G-S-S-P-C-T (SEQ ID NO: 6) |
| | Chothia | Q-Q-Y-G-S-S-P-C-T (SEQ ID NO: 6) |

Heavy-Chain

| | | |
|---|---|---|
| CDR1 | Kabat | N-Y-W-M-N (SEQ ID NO: 1) |
| CDR1-x | Chothia | G-F-T-F-S-N-Y-W-M-N (SEQ ID NO: 11) |
| CDR2 | Kabat | A-I-N-Q-D-G-S-E-K-Y-Y-V-G-S-V-K-G (SEQ ID NO: 2) |
| CDR2-x | Chothia | A-I-N-Q-D-G-S-E-K-Y (SEQ ID NO: 12) |
| CDR3 | Kabat | D-Y-Y-D-I-L-T-D-Y-Y-I-H-Y-W-Y-F-D-L (SEQ ID NO: 3) |
| CDR3-x | Chothia | C-V-R-D-Y-Y-D-I-L-T-D-Y-Y-I-H-Y-W-Y-F-D-L-W-G (SEQ ID NO: 13) |

In preferred embodiments, the constant region domains preferably also comprise suitable human constant region domains, for instance as described in "Sequences of Proteins of Immunological Interest", Kabat E. A. et al, US Department of Health and Human Services, Public Health Service, National Institute of Health. DNA encoding the $V_L$ of secukinumab is set forth in SEQ ID NO:9. DNA encoding the $V_H$ of secukinumab is set forth in SEQ ID NO:7.

In some embodiments, the IL-17 antibody or antigen binding fragment thereof (e.g., secukinumab) comprises the three CDRs of SEQ ID NO:10. In other embodiments, the IL-17 antibody or antigen binding fragment thereof comprises the three CDRs of SEQ ID NO:8. In other embodiments, the IL-17 antibody or antigen binding fragment thereof comprises the three CDRs of SEQ ID NO:10 and the three CDRs of SEQ ID NO:8. CDRs of SEQ ID NO:8 and SEQ ID NO:10 may be found in Table 1. The free cysteine in the light chain (CysL97) may be seen in SEQ ID NO:6.

In some embodiments, IL-17 antibody or antigen binding fragment thereof comprises the light chain of SEQ ID NO:14. In other embodiments, the IL-17 antibody or antigen binding fragment thereof comprises the heavy chain of SEQ preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antibody or antigen binding fragment thereof (e.g., secukinumab) is selected from a human IL-17 antibody that comprises at least: a) an immunoglobulin heavy chain or fragment thereof comprising a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof comprising a variable domain comprising, in sequence, the hypervariable regions CDR1', CDR2', and CDR3' and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO:6.

In one embodiment, the IL-17 antibody or antigen binding fragment thereof is selected from a single chain antibody or antigen binding fragment thereof that comprises an antigen binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, an IL-17 antibody or antigen binding fragment thereof as used in the disclosed methods may comprise a derivative of the IL-17 antibodies set forth herein by sequence (e.g., a pegylated version of secukinumab). Alternatively, the $V_H$ or $V_L$ domain of an IL-17 antibody or antigen binding fragment thereof used in the disclosed methods may have $V_H$ or $V_L$ domains that are substantially identical to the $V_H$ or $V_L$ domains set forth herein (e.g., those set forth in SEQ ID NO:8 and 10). A human IL-17 antibody disclosed herein may comprise a heavy chain that is substantially identical to that set forth as SEQ ID NO:15 (with or without the C-terminal lysine) and/or a light chain that is substantially identical to that set forth as SEQ ID NO:14. A human IL-17 antibody disclosed herein may comprise a heavy chain that comprises SEQ ID NO:15 (with or without the C-terminal lysine) and a light chain that comprises SEQ ID NO:14. A human IL-17 antibody disclosed herein may comprise: a) one heavy chain which comprises a variable domain having an amino acid sequence substantially identical to that shown in SEQ ID NO:8 and the constant part of a human heavy chain; and b) one light chain which comprises a variable domain having an amino acid sequence substantially identical to that shown in SEQ ID NO:10 and the constant part of a human light chain.

Alternatively, an IL-17 antibody or antigen binding fragment thereof used in the disclosed methods may be an amino acid sequence variant of the reference IL-17 antibodies set forth herein, as long as it contains CysL97. The disclosure also includes IL-17 antibodies or antigen binding fragments thereof (e.g., secukinumab) in which one or more of the amino acid residues of the $V_H$ or $V_L$ domain of secukinumab (but not CysL97), typically only a few (e.g., 1-10), are changed; for instance by mutation, e.g., site directed mutagenesis of the corresponding DNA sequences. In all such cases of derivative and variants, the IL-17 antibody or antigen binding fragment thereof is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts as described in Example 1 of WO 2006/013107.

In some embodiments, the IL-17 antibodies or antigen binding fragments thereof, e.g., secukinumab, bind to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (ie., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 pM. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (s.c.) administered IL-17 antibody has a range of about 60-about 80%, e.g., about 76%. In some embodiments, the IL-17 antibody, such as secukinumab, has an elimination half-life of about 4 weeks (e.g., about 23 to about 35 days, about 23 to about 30 days, e.g., about 30 days). In some embodiments, the IL-17 antibody (such as secukinumab) has a $T_{max}$ of about 7-8 days.

Particularly preferred IL-17 antibodies or antigen binding fragments thereof used in the disclosed methods are human antibodies, especially secukinumab as described in Examples 1 and 2 of WO 2006/013107. Secukinumab is a recombinant high-affinity, fully human monoclonal anti-human interleukin-17A (IL-17A, IL-17) antibody of the IgG1/kappa isotype that is currently in clinical trials for the treatment of immune-mediated inflammatory conditions. Secukinumab (see, e.g., WO2006/013107 and WO2007/117749) has a very high affinity for IL-17, i.e., a $K_D$ of about 100-200 pM and an $IC_{50}$ for in vitro neutralization of the biological activity of about 0.67 nM human IL-17A of about 0.4 nM. Thus, secukinumab inhibits antigen at a molar ratio of about 1:1. This high binding affinity makes the secukinumab antibody particularly suitable for therapeutic applications. Furthermore, it has been determined that secukinumab has a very long half-life, i.e., about 4 weeks, which allows for prolonged periods between administration, an exceptional property when treating chronic life-long disorders, such as rheumatoid arthritis.

Disclosed herein are processes for selectively reducing CysL97 in preparations of the above-mentioned IL-17 antibodies and antigen binding fragments thereof (e.g., secukinumab). The disclosed methods conveniently may be performed on preparations of antibodies (e.g., IL-17 antibodies, e.g., secukinumab) to reduce cost. A "preparation" of antibodies refers to a composition (e.g., solution) having a plurality of an antibody molecule. A "preparation" includes any liquid composition comprising the IL-17 antibody or antigen binding fragment thereof. As such, a preparation may comprise, e.g., IL-17 antibody or antigen binding fragment thereof, e.g., secukinumab, in water or a buffer, in a column elutate, in a dialysis buffer, etc. In some embodiments, the initial preparation of antibodies comprises a pool of the IL-17 antibodies or antigen binding fragments thereof, e.g., secukinumab, in a buffer (e.g., a Tris, e.g., 1 mM-1 M Tris, pH 6.0-8.0) or WFI. Prior to addition of the reducing agent to the antibody, the preparation may be adjusted by modifying dissolved oxygen levels, solution pH, antibody concentration, etc. In some embodiments, prior to addition of a reducing agent, the concentration of antibody (e.g., secukinumab) in the preparation is adjusted to between about 4 mg/ml-about 19.4 mg/ml, e.g., about 10 mg/ml-about 19.4 mg/ml, about 10 mg/ml-about 15.4 mg/ml, about 12 mg/ml-about 15 mg/ml, or about 13.5 mg/ml. In some embodiments, prior to addition of the reducing agent, the percent oxygen saturation in the preparation is adjusted to at least about 60% (as measured using an oxygen probe calibrated at 25° C.), e.g., at least about 80%. In some embodiments, prior to addition of the reducing agent, the pH of the preparation is adjusted to about 7.3-about 8.5, e.g., about 7.8-about 8.2, e.g., about 7.9-about 8.1, e.g., about 8.0. The concentration of antibody, pH and level of oxygen may also be adjusted immediately after (or even during) addition of the reductant, and thus should be interpreted as equivalent.

The preparations of IL-17 antibodies or antigen binding fragments thereof for use in the disclosed processes may be recombinantly produced by any mammalian cells using any mammalian cell line, e.g., Chinese hamster ovary cells (CHO) cells, mouse myeloma NSO cells, baby hamster kidney (BHK) cells, human embryonic kidney cell line HEK-293, the human retinal cell line Per.C6 (Crucell, NL), HKB11 cell clone (derived from a hybrid cell fusion of HEK 293S with the Burkitt's lymphoma line 2B8), etc. By "recombinantly produced by mammalian cells" is meant that production of the antibody in the mammalian cells has been achieved using recombinant DNA technology. The IL-17 antibody preparation subjected to selective reduction may be a pool of antibodies harvested from the mammalian cells by centrifugation (with or without subsequent clarification). Alternatively, the IL-17 antibody preparation subjected to selective reduction may be a pool of antibodies from a further downstream chromatography step, e.g., an eluate from an affinity column (e.g., a protein A column), a cation exchange column, an anion exchange column, etc. Alternatively, the IL-17 antibody preparation subjected to selective reduction may be a pool of antibodies from a downstream filtration step, e.g., depth filtration, nanofiltration, ultrafiltaration, etc. Alternatively, the IL-17 antibody preparation subjected to selective reduction may be a pool of antibodies from a downstream step in which the pool has been treated to remove host cell proteins and/or to inactivate viri. In a one embodiment, the preparation of IL-17 antibodies subjected to selective reduction is a protein A eluate pool of antibodies.

Depending on the process conditions chosen, e.g., temperature, length of reaction time, pH, etc.) the concentration of antibody in the original preparation will vary. In some embodiments, the concentration of the IL-17 antibody used in the original preparation is between about 2 mg/ml to about 20 mg/ml, about 3.8 mg/ml to about 19.5 mg/ml, about 4 mg/ml to about 19.5 mg/ml, about 10 mg/ml to about 19.4 mg/ml, e.g., about 10 mg/ml to about 15.4 mg/ml, e.g., about 12 mg/ml to about 15 mg/ml, e.g., about 13.5 mg/ml of the IL-17 antibodies or antigen binding fragments thereof. Prior to selective reduction, the antibody concentration in the initial antibody preparation may be adjusted as desired using water for injection (WFI) or a buffer of choice.

The selective reduction processes described herein may be performed in any size vessel. In some embodiments, the vessel is lab-scale (e.g., 1L-2L). In other embodiments, the vessel is pilot-scale (e.g., 12 L-20 L). In further embodiments, the vessel is commercial-scale (e.g., greater than 10,000 L, e.g., 14,000 L, 15,000 L, 16,000 L, etc.).

Reducing Agents

Reducing agents are substances capable of electron donation in a redox (reduction-oxidation) reaction. Specifically, such agents are useful to deliver hydrogen to a masked (or blocked) cysteine present in the IL-17 antibody or antigen binding fragment thereof (e.g., secukinumab antibody). The process disclosed herein uses reducing agents for the selective reduction of the IL-17 antibody. Each reducing agent referred to herein include derivatives thereof (e.g., salts, esters and amides). Thus, e.g., reference to "cysteine" includes cysteine and cysteine-HCL, reference to "TCEP" includes TCEP and TCEP-HCL, reference to thioglycolic acid includes sodium thioglycolate, etc. Reducing agents for use in the disclosed methods include sodium bisulfate, ammonia, triethylsilane, glycycicysteine, sodium cyanoborohydride, ammonium thioglycolate, calcium thioglycolate, sodium thioglycolate, ascorbic acid, hydroquinone, aminomethanesulphonic acid, cysteic acid, cysteinesulphinic acid, ethanedisulphonic acid, ethanesulphonic acid, homotaurine, hypotaurine, isethionic acid, mercaptoethanesulphonic acid, N-methyltaurine (MTAU), TCEP (Tris(2-carboxyethyl)phosphine hydrochloride), N-N-dimethyl-N-N bis(mercaptoacetyl)hydrazine (DMH), dithiothreitol (DTT), 2-mercaptoethanol (beta-mercaptoethanol), 2-mercaptoacetic acid (thioglycolic acid, TGA), cysteine (L-cysteine), cysteamine (beta-mercaptoethylamine, or MEA), glutathione, and combinations thereof. In some embodiments, the reducing agent for use in the disclosed process is a thiol-containing reducing agent (i.e., a compound having an R—SH group), e.g., an organosulfur compound. In some embodiments, the reducing agent for use in the disclosed process is, e.g., dithiothreitol (DTT), 2-mercaptoethanol, 2-mercaptoacetic acid, cysteine, cysteamine, glutathione and combinations.

The strength of a reducing agent is indicated by its oxidation-reduction potential (redox potential), E°, which is given in Volts (V) and traditionally determined at pH 7, 25° C. For example, the standard oxidation-reduction potential, E°, for CSH/CSSC is given as about -0.20 V to about -0.23 V (pH 7, 25° C.) (P. C. Jocelyn (1967) Eu. J. Biochem 2:327-31; Liu "The role of Sulfur in Proteins," in The Proteins, 3rd Ed. (ed. Neurath) p. 250-252 Academic Press 1977). The standard oxidation-reduction potential, E°, of DTT is given as about -0.33 V (pH 7, 25° C.) (M. J. O'Neil, ed. by (2001). Merck Index: an encyclopedia of chemicals, drugs, & biologicals: 13th ed. (13. ed. ed.) United States: MERCK & CO INC.; Liu, supra). The standard oxidation-reduction potential, E°, of glutathione is given as about -0.24 V or about -0.26 V (pH 7, 25° C.) (Rost and Rapoport (1964) Nature 201:185; Gilbert (1990) Adv. Enzymol. Relat. Areas Mol. Biol. 63:69-172; Giles (2002) Gen. Physiol Biophys 21:65-72; Liu, supra). The standard oxidation-reduction potential, E°, of 2-mercaptoethanol is given as about -0.26 V (Lee and Whitesides (1990) J. Org. Chem 58:642-647). In some embodiments, the reducing agent has a standard oxidation-reduction potential, E°, similar to cysteine (e.g., about -0.20 V to about -0.23 V, about -0.20 V to about -0.22 V, about -0.20 V to about -0.21 V, about -0.21 V to about -0.23 V, about -0.21 V to -0.22 V, about -0.22 V to about -0.23 V, about -0.20 V, about -0.21 V, about -0.22 V, about -0.23 V).

The standard oxidation-reduction potential E° of thiol-containing compounds may be measured by thermal analysis, reduction of NAD+, polarography, reaction with Fe++, or thiol-disulfide exchange studies (Jocelyn, supra; Borsook et al. (1937) J. Biol. Chem 117:281; Ghosh et al. (1932) J. Indian Chem. Soc. 9:43; Kolthoff et al. (1955) J. Am. Chem. Soc. 77:4739; Tanaka et al. (1955) J. Am. Chem. Soc.

77:2004; Kolthoff et al. (1955) J. Am. Chem. Soc. 77:4733; Eldjarn (1957) J. Am. Chem. Soc. 79:4589). In some embodiments, the standard oxidation-reduction potential E° is determined by thermal analysis, polarography, reaction with Fe++, or thiol-disulfide exchange studies, e.g., preferably by thiol-disulfide exchange studies. In some embodiments, the standard oxidation-reduction potential E° is determined at pH 7, 25° C.

The reducing agent, when combined with the antibody preparation, forms a "reducing mixture." The reducing mixture may comprise excipients in addition to the reducing agent and the IL-17 antibody. For example, in certain embodiments, a small molar ratio of the oxidized form (e.g., cystine, cystamine) of the reducing agent may be added to the reducing mixture either simultaneously with the reducing agent or sequentially, e.g., 10-30 minutes or more after the start of incubation. For example, if cysteine is the reducing agent, than a small amount of cystine may be added to the reducing mixture, e.g., concurrently with the cysteine or, e.g., 15, 20, 30 minutes after cysteine is combined with the IL-17 antibody or antigen binding fragment thereof. Thus, in some embodiments the reducing mixture comprises a set of oxidation/reduction reagents. By "set of oxidation/reduction reagents" is meant a redox pair or redox couple, i.e., an oxidizing and reducing agent that appear on opposite sides of a half-equation (e.g., a reducing species and its corresponding oxidized form, e.g., $Fe^{2+}/Fe^{3+}$, cysteine/cystine, cysteamine/cystamine).

Depending on the reaction conditions (temperature, length of reaction time, quantity of IL-17 antibody or antigen binding fragment thereof, pH, etc.) the concentration of reducing agent used in a particular reducing mixture and selective reduction reaction will vary. In some embodiments, the amount of reducing agent used in the reducing mixture will vary from about 1 to about 20 mM. In some embodiments, the concentration of reducing agent employed in the reducing mixture is about 1, 2, 3, 4, 5, 6, 7, 8, 9, 10, 11, 12, 13, 14, 15 or 16 mM. In one embodiment, the amount of reducing agent (e.g., cysteine) is between about 4 mM and about 8 mM, e.g., 5.9 mM, 6 mM, 7.7 mM, 7.9 mM, 8 mM.

In one embodiment, the reducing agent is beta-mercaptoethanol. In certain embodiments, beta-mercaptoethanol is employed at a concentration of about 2.0 mM to about 8.0 mM.

In one embodiment, the reducing agent is glutathione. In certain embodiments, glutathione is employed at a concentration of about 2.0 mM to about 5.0 mM.

In one embodiment, the reducing agent is cysteamine. In certain embodiments, cysteamine is employed at a concentration of about 1.0 mM to 20 mM, about 4.0 mM to about 19 mM, about 2.0 mM to about 8.0 mM, about 4.0 mM to about 8.0 mM, about 4.8 mM to about 8.0 mM, about 5.5 mM to about 6.7 mM, or about 6.0 mM.

In one embodiment, the reducing agent is cysteine. In certain embodiments, the concentration of cysteine in the reducing mixture is about 1.0 mM to 20 mM, about 4.0 mM to about 19 mM, about 2.0 mM to about 8.0 mM, about 4.0 mM to about 8.0 mM, about 4.8 mM to about 8.0 mM, about 5.5 mM to about 6.7 mM, or about 6.0 mM. Cysteine concentration may be adjusted using a stock solution of, e.g., 120 mM cysteine-HCL.

Each IL-17 antibody has two CysL97 residues in need of selective reduction. The amount of reducing agent employed should therefore be sufficient to selectively reduce both CysL97 residues on a substantial portion of IL-17 antibodies in a preparation of antibodies, without concomitantly over-reducing the antibody by irreversibly reducing the traditional disulfide bonds. Depending on the reaction conditions (presence of oxidizing agent, temperature, length of reaction time, pH, etc.) the molar ratio of reducing agent:IL-17 antibody used in a particular reducing mixture and selective reduction reaction will vary. We have found that the molar ratio of reducing agent (e.g., cysteine):antibody (e.g., secukinumab) can range from about 11:1 (Example 5.2) to as high as about 546:1 (Example 6.2). In some embodiments of the disclosed methods, the molar ratio of reducing agent (e.g., cysteine):antibody (e.g., secukinumab) is between about 11:1 to about 462:1 (e.g., about 21:1), about 31:1 to about 545:1 (e.g., about 31:1 to about 156:1), about 21:1 to about 296:1, or about 46:1 to about 91:1. In other embodiments, the molar ratio of reducing agent (e.g., cysteine):antibody (e.g., secukinumab) is between about 23:1 to about 91:1 (e.g., about 23:1 to about 57:1), about 44:1 to about 275:1 (e.g., about 44:1), about 44:1 to about 66:1 (e.g., about 44:1 to about 66:1), preferably about 46:1 to about 118:1 (e.g., about 56:1 to about 118:1), more preferably about 54:1 to about 82:1. In one embodiment, the molar ratio of reducing agent (e.g., cysteine):antibody (e.g., secukinumab) is about 66:1.

If a higher molar ratio of reducing agent (e.g., cysteine): antibody (e.g., secukinumab) is used (representing excess reducing agent c.f. to antibody), then addition of a small amount of the corresponding oxidizing agent (e.g., cystine or cystamine) may be useful to mitigate the reductive power of the reducing agent (e.g., cysteine or cysteamine). This is particularly beneficial in an anaerobic environment. Thus, in some embodiments, selective reduction is carried out using a set of oxidation/reduction reagents (e.g., in an aerobic or anaerobic environment, preferably an anaerobic environment). In some embodiments, selective reduction is carried out using a molar ratio of reducing agent (e.g., cysteine): oxidizing agent (e.g., cystine) of about 2:1 to about 80:1, about 4:1 to about 80:1, about 26:1 to about 80:1, about 2:1 to about 10:1 (e.g., about 6:1 to about 10:1), about 4:1 to about 28:1 (about 4:1 to about 18:1), about 27:1 to about 53:1 (e.g., about 27:1) in the reducing mixture. In certain embodiments, cysteine is used in the reducing mixture in combination with the oxidizing agent cystine or cystamine (preferably cystine). In some embodiments, selective reduction is carried out in conditions using about 4 mM-14 mM cysteine (e.g., about 7.7 mM to about 8.0 mM cysteine) and about 0.1 to about 1 mM cystine (e.g., about 0.1 to about 0.3 mM cystine) in the reducing mixture. In certain embodiments, the reducing mixture contains about 8.0 mM cysteine and about 0.1 mM cystine, about 7.9 mM cysteine and about 0.1 mM cystine, or about 7.7 mM cysteine and about 0.3 mM cystine. It will be understood that if an oxidizing agent, e.g., cystine, is employed in combination with the reducing agent, e.g., cysteine, in the disclosed process, the oxidizing agent, e.g., cystine, may be added at a point after the reducing agent, e.g., cysteine, is combined with the IL-17 antibody or antigen binding fragment thereof. For example, the IL-17 antibody or antigen binding fragment thereof may be combined with cysteine to form a reducing mixture, which is then incubated for, e.g., 15-30 minutes; thereafter, cystine may be added to the reaction.

Dissolved Oxygen

As used herein, "dissolved oxygen", "$dO_2$" and "DO" refer to the amount of oxygen that is dissolved or carried in a given medium. It can be measured with an oxygen probe, such as an oxygen sensor or an optode in liquid media. DO is reported as either as a concentration (milligrams per liter (mg/L)) or as "percent saturation." Milligrams per liter is the amount of oxygen in a liter of solvent and is also equivalent to parts per million=ppm. Percent oxygen saturation is the amount of oxygen in a solution relative to the total amount of oxygen that the solution can hold at a particular temperature.

As used herein, "initial percent oxygen saturation" refers to the amount of dissolved oxygen in the preparation of IL-17 antibodies (e.g., secukinumab) prior to contacting the preparation with the reducing agent in the vessel to form the reducing mixture. The initial percent oxygen saturation can be adjusted directly (e.g., by sparging) or indirectly (e.g., by stirring) to achieve a desired level of oxygen prior to the beginning of the selective reduction process. For example, in some embodiments the initial percent oxygen saturation in the IL-17 antibody preparation is adjusted to at least 40%, 50%, 60%, 70%, 80%, 90%, or even as high as 100% prior to contact with the reducing agent. This may be done in order to initially mitigate the power of the reducing agent once that agent is added to the IL-17 antibody preparation to form the reducing mixture, which avoids partial or complete reduction of the traditional disulfides of the antibody that otherwise would lead to loss of activity and purity. In preferred embodiments, the initial percent oxygen saturation in the IL-17 antibody preparation is adjusted to at least 60% (as measured using an oxygen probe calibrated at 25° C.). In preferred embodiments, the initial percent oxygen saturation in the IL-17 antibody preparation is adjusted to at least 80% (as measured using an oxygen probe calibrated at 25° C.).

We have determined that elevated oxygen levels during the cysteine treatment step can have a deleterious effect on antibody activity, which is likely due to the oxygen abrogating the reductive power of the cysteine, leading to insufficient reduction of C97 of secukinumab. This issue of oxygen uptake from the atmosphere can be managed by varying the amount of reducing agent, varying the molar ratio of reducing agent:antibody, using defined stirring speeds, or even employing stirring interruptions, especially when working at production scale. It will be understood that higher amounts of reducing agent (e.g., cysteine) are capable of handling higher oxygen levels in the reducing mixture. In some embodiments, during the incubation step of the selective reduction process, the oxygen saturation in the reducing mixture is generally maintained at a low percentage (e.g., less than about 40%, less than about 30%, less than about 20%, less than about 15%, less than about 10%, less than about 5%).

A loss of reductive power of the reducing agent (e.g., cysteine) likely leads to incomplete deblocking of CysL97-SH at earlier time points during the incubation step, and if there is no residual reducing agent (e.g., cysteine) available to protect deblocked Cys97L at later portions of the incubation step (or during the cooling step), then reoxidation of deblocked Cys97L-SH can occur. Therefore, ideally, a low percentage oxygen saturation will be maintained for at least about 60 minutes to about 330 minutes, e.g., at least about 60 minutes, at least about 90 minutes, at least about 120 minutes, at least about 150 minutes, at least about 180 minutes, at least about 210 minutes, at least about 240 minutes, at least about 270 minutes, at least about 300 minutes, or at least about 330 minutes. In some embodiments, this low percentage oxygen saturation will be maintained for the full incubation step, as well as part of the cooling step.

Percent oxygen saturation can be adjusted directly (e.g., by sparging) or indirectly (e.g., by stirring) to achieve a desired level of oxygen during incubation of the reducing mixture. In an aerobic environment, a low percent oxygen saturation may be achieved by using intermittent (rather than continuous) mixing of the reducing solution, e.g., <15 min/hr, e.g., <2 min/hr, or by using continuous stirring with a low spin speed. In an anaerobic environment, no (or little) oxygen is present that would lead to consumption of the reducing agent.

Volumetric Oxygen Mass-Transfer ($k_La^*$)

When selective reduction is performed under aerobic conditions, the level of oxygen in the reaction is not controlled directly, but via other process parameters, e.g., stir speed. The physical setup of each reaction also influences the level of oxygen present in the reaction mixture. Therefore, it is important to identify a variable that can be used to compare the oxygen transferred into a solution between physical setups and during particular antibody processing steps—that variable is "$k_La^*$" (see, e.g., Garcia-Ochoa and Gomez (2009) Biotechnology Advances 27:153-176; Bandino et al. (2001) Biochem. Engineering J. 8:111-119; Juarez and Orejas (2001) Latin Am. Appl. Res. 31:433-439; Yange and Wang (1992) Biotechnol. Prog. 8:244-61). The $k_La^*$ represents the amount of oxygen transferred into a solution over time via the headspace without sparging. This value is specific for each setup and scale, and depends on stirrer type, stirrer speed, filling volume and surface area of the solution in contact with the headspace, which is influenced by the individual geometry of each vessel. While the $k_La^*$ of each physical setup differs, because the level of oxygen in the solution during the selective reduction process effects the activity and integrity of secukinumab, we expect that the selective reduction process, when performed in systems displaying similar $k_La^*$ ranges, will lead to preparations of secukinumab having similar quality.

As used herein the term "system" encompasses both the physical setup (vessel, stir type, etc.) and the process conditions (fill volume, spin speed, etc.) that influence the oxygen transfer into a solution over time via the headspace without sparging, i.e., scale, stirrer speed, filling volume, surface area of the solution in contact with the headspace, which is influenced by the individual geometry of each vessel, etc.

As used herein the term "vessel" means any container in which the selective reduction reaction takes place. Vessels include, without limitation, bioreactors (e.g., steel, stirred tank, disposable or non-disposable, etc.) used for pilot and commercial scale antibody production, as well as common laboratory containers, such as flasks, tubes, etc. In some embodiments, the vessel is a bioreactor capable of holding a volume of at least about 2 liters, at least about 100 liters, at least about 500 liters, at least about 1000 liters, at least about 2000 liters, at least about 5000 liters, at least about 10,000 liters, at least about 15,000 liters or greater.

The $k_La^*$ cannot be directly determined in the oxygen transfer experiments. Instead, the $dO_2$ in a test solution is replaced by nitrogen and the increase of $dO_2$ over time is monitored using a calibrated $dO_2$ probe, which allows creation of an experimental $dO_2$ curve. Thereafter, the $k_La^*$ values used herein are calculated for the particular systems by adapting the experimental $dO_2$ curve to a saturation curve (e.g., using Mathcad®) according the equation shown below:

$DO = C \times (1 - e^{-kLa^* \times (t-t0)})$, where DO=the measured value of dissolved oxygen, C is the saturation value of oxygen (meaning 100% when stirred infinitely and saturation is achieved), Euler's number e=2.718281 . . . , t=time point corresponding to the DO value, and $t_0$=starting time point.

The equation represents the integrated form of an empirical formula established for determination of the oxygen transfer into solutions ($k_L a^*$ value). The formula was confirmed by different authors in various experiments (Doran, P. M. 1995. Bioprocess Engineering Principles, Academic Press, San Diego, Calif.).

We have determined that the heating and cooling steps of the selective reduction process are generally more tolerable of a higher $k_L a^*$ than the incubation step. This is because elevated oxygen levels during the incubation step can have a deleterious effect on antibody activity, which is likely due to the increased oxygen transfer abrogating the reductive power of the reducing agent (e.g., cysteine), leading to insufficient reduction of C97 of secukinumab. In an aerobic environment, increasing the stir speed (or stir time) in the reducing mixture during the selective reduction process increases the $k_L a^*$. Continuous stirring of the reducing mixture, which leads to higher $k_L a^*$ values, can be tolerated during the heating and cooling steps. In some embodiments, the $k_L a^*$ during the heating and cooling steps (separately) can be from about 0.12 $h^{-1}$ to about 1.69 $h^{-1}$, about 0.08 $h^{-1}$ to about 0.69 $h^{-1}$, about 0.24 $h^{-1}$ to about 0.44 $h^{-1}$, about 0.39 $h^{-1}$ to about 0.69 $h^{-1}$. In some embodiments, the $k_L a^*$ in the system during the heating or cooling step is ≤about 0.69 $h^{-1}$, said $k_L a^*$ being calculated by adapting a saturation curve to a dissolved oxygen curve.

It is preferable to keep the $k_L a^*$ lower during the incubation step using, e.g., continuous stirring with low spin speeds, or, preferably, intermittent stirring. In some embodiments, the reducing mixture is incubated while maintaining a volumetric oxygen mass-transfer coefficient ($k_L a^*$) in the system of ≤about 0.37 $h^{-1}$, ≤about 0.27 $h^{-1}$, or ≤about 0.18 $h^{-1}$, said $k_L a^*$ being calculated by adapting a dissolved oxygen curve to a saturation curve. If the $k_L a^*$ in the system during the incubation step of the selective reduction reaction is less than (<) 0.37 $h^{-1}$, then the molar ratio of reducing agent (e.g., cysteine):antibody can vary between 46.11:1 (about 46:1) to 118.36:1 (about 118:1) (for both shorter and longer incubation times, e.g., about 210 to about 330 minutes). The $k_L a^*$ in the system during the incubation step of the selective reduction reaction can be as high as (≤) 0.37 $h^{-1}$ if the molar ratio of reducing agent (e.g., cysteine):protein is between 69.89:1 (about 70:1) to 118.36:1 (about 118:1) (for shorter incubation times, e.g., up to about 240 minute incubation) or between 76.85 (about 77:1) to 118.36:1 (about 118:1) (for longer incubation times, e.g., up to about 300 minute incubation).

The entire selective reduction process (i.e., heating step, incubation step, and cooling step) can be generally performed using a $k_L a^*$ of <0.37 $h^{-1}$, which includes about 210-about 330 minute incubation time (e.g., about 240 minute-300 minute incubation time), if the molar ratio of reducing agent (e.g., cysteine):antibody is between about 46:1-about 118:1. The entire selective reduction process (i.e., heating step, incubation step, and cooling step) can be generally performed using a $k_L a^* \leq 0.37$ $h^{-1}$ if the molar ratio of reducing agent (e.g., cysteine):antibody is between about 70:1-about 118:1, and incubation is up to about 240 minutes; or if the molar ratio of reducing agent (e.g., cysteine): antibody is between about 77:1-about 118:1, and incubation is up to about 300 minutes.

Further Process Components

The present disclosure provides a method for selective reduction of CysL97 in certain IL-17 antibodies, such as secukinumab, comprising contacting the antibody with a reducing agent to form a reducing mixture. It will be understood that the reducing mixture may comprise components in addition to the IL-17 antibody or antigen binding fragment thereof and the reducing agent. The reducing mixture may contain an aqueous component (e.g., a buffer, such as a Tris buffer), as well as reagents used to increase or decrease the pH of the reducing mixture, salt, EDTA, etc. Thus, while the reducing mixture will necessarily contain the IL-17 antibody (e.g., secukinumab) and the reducing agent, the reducing mixture may or may not contain additional components. In some embodiments, the reducing mixture contains a metal chelator (e.g, EDTA, DMSA, DMPS). In some embodiments, the reducing mixture contains 1.3 mM to about 0.8 mM, about 1.1 to about 0.9 mM, or about 1.0 mM EDTA (e.g., di-Na-EDTA).

Depending on the reaction conditions (temperature, length of reaction time, quantity of IL-17 antibody, concentration of reducing agent, ratio reducing agent:antibody, etc.) the pH of a particular antibody preparation may vary. However, it is recognized that, based upon the reaction conditions described herein, such conditions can be varied in order to achieve the desired selective reduction. In some embodiments, the pH of the antibody preparation prior to contact with the reducing agent will vary from about 6.5 to about 9.5, e.g., about 7 to about 9. In other embodiments, the pH of the antibody preparation will be about 7.4 to about 8.5, about 7.8 to about 8.2, about 7.9 to about 8.1, or about 8.0. In some embodiments, the pH of the antibody preparation may be adjusted (e.g., following gassing to adjust the initial percent oxygen saturation) using a buffer, e.g., a 1M Tris buffer (e.g., 1M Tris buffer pH 10.8).

Following contacting of the preparation containing the IL-17 antibody or antigen binding fragment thereof (e.g., secukinumab) with the reducing agent, there may be an initial reduction in the level of intact IL-17 antibody or antigen binding fragment thereof (HLLH). The term "intact" refers to an antibody having all conserved disulfide bridges (e.g., 14 conserved disulfide bridges in the case of a classical $IgG_1$ antibody). The formation of various IL-17 antibody fragments, i.e., $H_2L$, $HL_2$, HL, H and L bands, as well as the intact $H_2L_2$ (HHLL) band can be determined using different analytical tools known in the art (such as SDS-PAGE, Cation-exchange HPLC). Preferably, the level of intact IL-17 antibody or antigen binding fragment thereof in the mixture is measured by sodium dodecyl sulfate capillary electrophoresis (CE-SDS). CE-SDS separates proteins according to their molecular size in an electric field. Non-reducing CE-SDS can be used to assess size variants in a preparation of antibodies. In some embodiments, the level of intact IL-17 antibody or antigen binding fragment thereof in the mixture decreases to at least about 80%, as measured by CE-SDS, within about 1-30 minutes (e.g., about 15 minutes) of addition of the reducing agent to the antibody preparation. In some embodiments, the level of intact IL-17 antibody or antigen binding fragment thereof in the mixture decreases to at least about 83%, as measured by CE-SDS. In some embodiments, the level of intact IL-17 antibody or antigen binding fragment thereof in the mixture decreases to between about 75% to about 87%. In some embodiments, the level of intact IL-17 antibody or antigen binding fragment thereof in the mixture decreases to at least about 38, 39, 40, 41, 45, 50, 55, 60, 65, 70, 71, 72, 73, 74, 75, 76, 77, 78, 79, 80, 81, 82, 83, 84, 85, 86, or 87%, as measured by CE-SDS.

CE-SDS analyses may be performed using a Beckman Coulter PA-800 capillary electrophoresis system. Uncoated fused-silica capillaries with an inner diameter of 50 μm and a length of 30 cm (with 20 cm and 10 cm separation ranges for reducing CE-SDS and non-reducing CE-SDS analyses, respectively) are used for the analyses. The separation is monitored with a UV detector at 214 nm. For non-reducing CE-SDS analyses, antibody samples are diluted to 6.0 mg/mL with water, mixed thoroughly with non-reducing CE-SDS sample buffer (0.1 M Tris/1.0% SDS, pH 7.0) and 250 mM iodoacetamide, at a ratio of 20/75/5 (v/v/v), and heated at 70° C. for 10 minutes to prevent disulfide bridge shuffling. The capillary temperature is set at 25° C. for the separation. The electrophoresis is carried out at a constant voltage of 15 kV in the normal polarity mode for 20 minutes.

In some embodiments, the reducing mixture is heated. In some embodiments, heating occurs prior to the step of incubating. In some embodiments, the reducing mixture is heated to a temperature between about 32° C. to about 42° C., to between about 35° C. to about 39° C., to about 37° C. In some embodiments, the heating occurs for about 30 to about 120 minutes, about 45 to about 90 minutes, about 45 to about 75 minutes, about 60 minutes. During heating, the reducing mixture may be stirred, e.g., constantly or intermittently, using any means for stirring. Stirring may be axial (e.g., using a pitched blade impeller) or radial (e.g., using a rushton turbine). In some embodiments, during heating the reducing mixture is constantly stirred at 65-200 rpm (e.g., 50 rpm, 65 rpm, 75 rpm, 85 rpm, 100 rpm or 200 rpm).

During the incubating step, the reducing mixture will typically be incubated for a predetermined time to allow selective reduction of the free cysteine (e.g., the free cysteine of secukinumab). In some embodiments, incubation occurs following heating of the reducing mixture. Depending on the reaction conditions (reducing agent, temperature, quantity of IL-17 antibody or antigen binding fragment thereof, pH, etc.) the predetermined time for incubation of the reducing mixture will vary. In some embodiments, the time will vary between about 1 and 24 hours (e.g., 1, 2, 3, 4, 5, 6, 7, 8, 9, 10, 11, 12, 13, 16, 18, 20 or 24 hours). In some embodiments, incubating is performed for about 200 to about 500 minutes, about 210 to about 420 min., about 210 to about 330 minutes, about 240 to about 300 minutes, about 250 minutes.

During the incubating step, incubation will be performed at a predetermined temperature to allow selective reduction of the target free cysteine (e.g., CysL97 in the antigen binding sites of secukinumab). Depending on the reaction conditions (reducing agent, time, quantity of IL-17 antibody or antigen binding fragment thereof, pH, etc.) the incubation temperature will vary. In some embodiments, the predetermined temperature will vary between about 20 to about 42° C. In some embodiments, the predetermined temperature will be about 32° C.-about 42° C., between about 35° C.-about 39° C., or about 37° C.

During the incubating step, the reducing mixture may be stirred to ensure product homogeneity while the reductant is incubated with the IL-17 antibody preparation, e.g., secukinumab. However, the level of oxygen in the vessel should be kept low during this portion of the selective reduction reaction in order to allow the reducing agent to effectively selectively reduce CysL97 in the IL-17 antibodies. Under aerobic conditions, low oxygen may be achieved by avoiding continuous stirring, e.g., by using intermittent stirring, e.g., ≤15 min/hr, e.g., ≤2 min/hr. Under anaerobic conditions, transfer of oxygen is limited and therefore stifling may proceed for longer periods of time or may be continuous. Moreover, under anaerobic conditions, strict control of oxygen transfer (e.g., by regulated sparging) would also allow application of longer periods of stir time (including continuous stirring).

In some embodiments, the mixture is cooled following the incubating step. In some embodiments, the mixture is cooled to room temperature (e.g., a temperature between about 16° C. to about 28° C.). In some embodiments, cooling occurs for about 30 to about 120 minutes, about 45 to about 90 minutes, about 45 to about 75 minutes, about 60 minutes. During cooling, the reducing mixture may be stirred, e.g., constantly or intermittently using any means for stirring. Stirring may be axial (e.g., using a pitched blade impeller) or radial (e.g., using a rushton turbine). In some embodiments, during cooling the reducing mixture is constantly stirred at 65-200 rpm (e.g., 50 rpm, 65 rpm, 75 rpm, 85 rpm, 100 rpm or 200 rpm).

The selective reduction reaction may be quenched, e.g., using iodoacetamid or o-phosphoric acid (e.g., using a stock solution of 0.3 M o-phosphoric acid). In some embodiments, quenching occurs following the cooling step. In some embodiments, the selective reduction reaction is quenched by adjusting the pH of the mixture to between about 5.0 to about 5.5, about 5.1 to about 5.3, about 5.2. pH adjustment may be achieved using o-phosphoric acid.

The phrase "purified preparation" refers to a mixture of IL-17 antibodies or antigen binding fragments thereof that have been subjected to selective reduction. After completion of selective reduction, there will be an increase in the level of intact IL-17 antibody in the purified preparation. The level of intact antibodies in the purified preparation after selective reduction may be measured via various well known techniques (e.g., non-reducing SDS PAGE, CE-SDS PAGE, size exclusion chromatography (SEC), HPLC). In some embodiments, the level of intact antibody is measured by CE-SDS. In some embodiments, after completion of selective reduction (e.g., after the cooling step), the level of intact IL-17 antibody or antigen binding fragment thereof in the purified preparation is at least about 80%, as measured by CE-SDS. In some embodiments the level of intact IL-17 antibody or antigen binding fragment thereof in the purified preparation is at least about 80, 81, 82, 83, 84, 85, 86, 87, 88, 89, 90, 91, 92, 93 94, 95, 96, 97, 98, 99, or about 100%, as measured by CE-SDS, after selective reduction. In some embodiments, the level of intact IL-17 antibody or antigen binding fragment thereof in the purified preparation is at least about 90%, as measured by CE-SDS, after selective reduction.

The activity (e.g., affinity, biological activity, etc.) of the antibodies in a preparation prior to selective reduction, during selective reduction or after selective reduction (i.e., in a purified preparation) may be measured via various well known techniques (see, e.g., WO2006/013107; WO2007/117749; Shen and Gaffen (2008) Cytokine. 41(2): 92-104). In certain embodiments, the activity is measured using an ELISA based assay or a cell-based assay (e.g., inhibition of IL-17 dependent release of IL-6 or GROalpha from, e.g., C-20/A4 chondrocytes or BJ cell line). In some embodiments, activity is measured by a cystamine-CEX (cation exchange chromatography) method. The cystamine-CEX method includes derivatization of the antibody with cystamine (2,2'-dithiobis(ethylamine)), followed by analytical separation using cation exchange chromatography (CEX). Because the activity of the antibodies disclosed herein (e.g., secukinumab) is decreased if CysL97 is in oxidized form, derivatization of CysL97 with cystamine serves as a proxy to measure antibody activity, i.e., if selective reduction succeeds then reduced CysL97 can be derivitized with cystamine, whereas if selective reduction fails then oxidized CysL97 cannot be derivitized with cystamine. Derivatization by cystamine leads to an addition of one positive charge per free Cys97 residue. The resulting derivatized forms of secukinumab (e.g., +2, +1 charges) can then be separated from the non-derivatized form and quantified by CEX. A cystamine-derivatized secukinumab molecule with two cystamine bound to unpaired Cys97 on both light chains may be considered 100% biological active in theory. A cystamine-derivatized secukinumab molecule with addition of one cystamine bound to unpaired Cys97 on one of the light chains may be considered 50% biological active. A cystamine-derivatized secukinumab molecule without any cystamine bound to the molecule may be considered biological inactive. The level of cystamine derivitization in a preparation of antibodies (e.g., a preparation of secukinumab antibodies), in comparison to the theoretical maximum level of cystamine derivitization in that preparation (e.g., expressed as a percentage of theoretical maximum) may then be used as a measure of the activity of the preparation.

In brief cystamine-CEX may be performed as follows. Antibody samples (50 µg) are first treated with carboxypeptidase B (1:40, w:w) to remove the C-terminal lysine in the heavy chain and then derivatized with 4 mM cystamine in 5 mM sodium acetate, 0.5 mM EDTA, pH4.7 at room temperature for 2 hours. The derivatization is stopped by addition of 2 µL of 1M phosphoric acid. CEX is performed on the cystamine-derivatized antibody samples using a ProPac™ WCX-10 analytical column (4 mm×250 mm, Dionex). A gradient from 12.5 mM to 92.5 mM sodium chloride in 25 mM sodium phosphate, pH 6.0 at a flow rate of 1.0 ml/min is used for separation. Absorption at 220 nm is recorded by a UV detector (Agilent HPLC 1200).

Some initial preparations of IL-17 antibody with an oxidized free cysteine have activity levels as low as 45%. In some embodiments, prior to initiating the selective reduction process, the level of activity of the IL-17 antibodies or antigen binding fragments thereof in the preparation is less than about 80%, less than about 75%, less than about 70%, less than about 65%, less than about 60%, less than about 55%, less than about 50%, or less than about 45% (e.g., as measured by the cystamine-CEX method). During selective reduction, there will be an increase in the level of activity of the IL-17 antibodies in the purified preparation. In some embodiments, the level of activity of the IL-17 antibodies or antigen binding fragments thereof in the antibody preparation increases by at least about 15 percentage points (e.g., from about 60% to at least about 75%), at least about 20 percentage points (e.g., from about 60% to at least about 80%), at least about 25 percentage points (e.g., from about 60% to at least about 85%) or at least about 30 percentage points (e.g., from about 60% to at least about 90%) within about 60 minutes following contacting the antibody preparation with the reducing agent to form the reducing mixture (e.g., as measured by the cystamine-CEX method).

After selective reduction, the purified preparation will be enriched for IL-17 antibodies having the reduced form of CysL97 and will display an increased level of activity relative to the initial preparation. In some embodiments, after completion of selective reduction, the level of activity of the IL-17 antibodies or antigen binding fragments thereof in the purified preparation is at least about 80% (relative to a theoretical maximum), as measured by cystamine-CEX, an ELISA, or cell-based binding assay (e.g., a cystamine-CEX assay). In some embodiments, after completion of selective reduction, the level of activity of the IL-17 antibodies or antigen binding fragments thereof in the purified preparation is at least about 80, 81 82, 83, 84, 85, 86, 87, 88, 89, 90, 91, 92, 93 94, 95, 96, 97, 98, 99 or about 100%, as measured by CEX, an ELISA, or cell-based binding assay (e.g., a cystamine-CEX assay). In some embodiments, after completion of selective reduction, the level of activity of the IL-17 antibodies or antigen binding fragments thereof in the puri-fied preparation is at least about 93%, as measured by cystamine-CEX, an ELISA, or cell-based binding assay (e.g., a cystamine-CEX assay).

Accordingly, disclosed herein are methods for selectively reducing CysL97 in a preparation of IL-17 antibodies that have been recombinantly produced by mammalian cells, comprising:
 a) contacting the preparation with at least one reducing agent in a system to form a reducing mixture; and
 b) incubating the reducing mixture while maintaining a volumetric oxygen mass-transfer coefficient ($k_L a^*$) in the system of ≤about 0.37 h$^{-1}$, said $k_L a^*$ being calculated by adapting a dissolved oxygen curve to a saturation curve;
wherein the IL-17 antibodies each comprise an immunoglobulin heavy chain variable domain ($V_H$) comprising the three complementarity determining regions (CDRs) of the $V_H$ set forth as SEQ ID NO:8 and an immunoglobulin light chain variable domain ($V_L$) comprising the three CDRs of the $V_L$ set forth as SEQ ID NO:10, and further wherein prior to step a) the initial percent oxygen saturation in the preparation is at least about 60%, as measured using an oxygen probe calibrated at 25° C.

Also disclosed herein are methods for selectively reducing CysL97 in a preparation of IL-17 antibodies that have been recombinantly produced by mammalian cells, comprising:
 a) contacting the preparation with a set of oxidation/reduction reagents selected from cysteine/cystine and cysteine/cystamine to form a reducing mixture; and
 b) incubating the reducing mixture at a temperature of about 37° C. under anaerobic conditions for at least about 4 hours, or incubating the reducing mixture at a temperature of about 18-24° C. for about 16-24 hours;
wherein the IL-17 antibodies each comprise an immunoglobulin heavy chain variable domain ($V_H$) comprising the three complementarity determining regions (CDRs) of the $V_H$ set forth as SEQ ID NO:8 and an immunoglobulin light chain variable domain ($V_L$) comprising the three CDRs of the $V_L$ set forth as SEQ ID NO:10.

Also disclosed herein are methods for selectively reducing CysL97 in a preparation of secukinumab antibodies that have been recombinantly produced by mammalian cells, comprising:
 a) adjusting the concentration of secukinumab in the preparation to between about 4 mg/ml-about 19.4 mg/ml, e.g., about 10 mg/ml-about 19.4 mg/ml, e.g., about 10-about 15.4, e.g., about 12 mg/ml-about 15 mg/ml, e.g., about 13.5 mg/ml;
 b) adjusting the percent oxygen saturation in the preparation to at least about 60%, e.g., at least about 80%;
 c) adjusting the pH of the preparation to about 7.4-about 8.5, e.g., about 7.8-about 8.2, e.g., about 7.9-about 8.1, e.g., about 8.0;
 d) contacting the preparation with cysteine in a vessel to form a reducing mixture, wherein the concentration of cysteine in the reducing mixture is about 4.0 mM-about 8.0 mM, e.g., about 4.8 mM-about 8.0 mM, e.g., about 5.5 mM-about 6.7 mM, e.g., about 6.0 mM;
 e) heating the reducing mixture to a temperature between about 32° C.-about 42° C., e.g., to between about 35° C.-about 39° C., e.g., to about 37° C., said heating occurring for about 45-about 90 minutes, e.g., about 45-about 75 minutes, e.g., about 60 minutes;
 f) incubating the reducing mixture from step e) at a temperature between about 20° C.-about 42° C., e.g., 32° C.-about 42° C., e.g., to between about 35° C.-about 39° C., e.g., to about 37° C., said incubating occurring for about 210-about 420 minutes, e.g., about 210-about 330 minutes, e.g., about 240-about 300 minutes, e.g., about 250 minutes while maintaining a volumetric oxygen mass-transfer coefficient ($k_L a^*$) in the vessel of ≤0.37 h$^{-1}$, said $k_L a^*$ being calculated by adapting a saturation curve to a dissolved oxygen curve, g) cooling the mixture resultant from step f) to a temperature between about 16° C.-about 28° C., said cooling occurring for about 45-about 90 minutes, e.g., about 45-about 75 minutes, e.g., about 60 minutes; and h) adjusting the pH of the mixture resultant from step g) to between about 5.1-about 5.3, e.g., about 5.2.

Also disclosed herein are also purified preparations of secukinumab, wherein the level of intact secukinumab in the preparation is at least about 90%, as measured by sodium dodecyl sulfate capillary electrophoresis (CE-SDS), and wherein the level of activity of secukinumab in the preparation is at least about 90%, as measured by cystamine-CEX.

General

In some embodiments of the above methods, the IL-17 antibody or antigen binding fragment thereof comprises: i) an immunoglobulin heavy chain variable domain (VH) comprising the amino acid sequence set forth as SEQ ID NO:8; ii) an immunoglobulin light chain variable domain (VL) comprising the amino acid sequence set forth as SEQ ID NO:10; iii) an immunoglobulin VH domain comprising the amino acid sequence set forth as SEQ ID NO:8 and an immunoglobulin VL domain comprising the amino acid sequence set forth as SEQ ID NO:10; iv) an immunoglobulin VH domain comprising, in sequence, the hypervariable regions set forth as SEQ ID NO:1, SEQ ID NO:2, and SEQ ID NO:3; v) an immunoglobulin VL domain comprising, in sequence, the hypervariable regions set forth as SEQ ID NO:4, SEQ ID NO:5 and SEQ ID NO:6; vi) an immunoglobulin VH domain comprising, in sequence, the hypervariable regions set forth as SEQ ID NO:11, SEQ ID NO:12 and SEQ ID NO:13; vii) an immunoglobulin VH domain comprising, in sequence, the hypervariable regions set forth as SEQ ID NO:1, SEQ ID NO:2, and SEQ ID NO:3 and an immunoglobulin VL domain comprising, in sequence, the hypervariable regions set forth as SEQ ID NO:4, SEQ ID NO:5 and SEQ ID NO:6; and viii) an immunoglobulin VH domain comprising, in sequence, the hypervariable regions set forth as SEQ ID NO:11, SEQ ID NO:12 and SEQ ID NO:13 and an immunoglobulin VL domain comprising, in sequence, the hypervariable regions set forth as SEQ ID NO:4, SEQ ID NO:5 and SEQ ID NO:6. In some embodiments of the disclosed methods, the IL-17 antibody or antigen binding fragment thereof is a human antibody of the IgG$_1$ isotype. In some embodiments of the disclosed methods, the antibody is secukinumab.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

Example 1: Reduction of Secukinumab Protein a Intermediate by Different Sulfhydryl Agents Example 1.1

A variety of sulfhydryl group-containing reducing agents (e.g., dithiothreitol (DTT), 2-mercaptoethanol, 2-mercaptoacetic acid, cysteine, cysteamine, glutathione) were screened for their use in selectively reducing the oxidized Cys97 in the light chain of secukinumab. In a first set of experiments, 1-mL portions of inactive starting material obtained from an early fermentation process after the Protein A capture step were incubated at 37° C. at various pH with various concentrations of β-mercaptoethanol, cysteine and glutathione. After certain time-points, the samples were desalted by gel filtration into 20 mM acetate pH 6 buffer and restoration of activity was determined by an ELISA. Also, the content of free sulfhydryl groups was determined by Ellman test (deblocking of the sulfhydryl group should result in a value of 2 Mol free-SH per mol antibody). The results are listed in the Table 2, below.

TABLE 2

Activity and free-SH of samples following reaction at given conditions.

| | 2-ME° | Activity % * | Free SH Mol/Mol | Cysteine | Activity % * | Free SH Mol/Mol | Glutathione | Activity % * | Free SH Mol/Mol |
|---|---|---|---|---|---|---|---|---|---|
| pH 7 | | | | | | | | | |
| 37° C. | 5 mM/1 h | 59 | 1.3 | | | | | | |
| | /4 h | 85 | 1.6 | | | | | | |
| | /8 h | 85 | 1.6 | | | | | | |
| pH 8 | | | | | | | | | |
| 37° C. | | | | 1 mM/2 h | 61 | 1.4 | | | |
| | | | | /8 h | 90 | 1.8 | | | |
| | 2 mM/1 h | 64 | 1.4 | 2 mM/2 h | 80 | 1.8 | 2 mM/2 h | 45 | 1.4 |
| | /4 h | 82 | 1.9 | /4 h | 98 | 1.9 | /8 h | 65 | 2.0 |
| | /8 h | 88 | n.p. | | | | | | |

TABLE 2-continued

Activity and free-SH of samples following reaction at given conditions.

| 2-ME° | Activity % * | Free SH Mol/Mol | Cysteine | Activity % * | Free SH Mol/Mol | Glutathione | Activity % * | Free SH Mol/Mol |
|---|---|---|---|---|---|---|---|---|
| 4 mM/1 h | 88 | 1.3 | 4 mM/1 h | 77 | 0.9 | 4 mM/2 h | 59 | 1.6 |
| /4 h | 91 | 1.8 | /4 h | 105 | 1.9 | /4 h | 94 | 1.8 |
| /8 h | 106 | 2.0 | | | | 8 mM/1 h | 58 | 1.4 |
| | | | | | | /4 h | 75 | 1.7 |
| pH 9 | | | | | | | | |
| 37° C. | | | 1 mM/2 h | 48 | 1.2 | | | |
| | | | /8 h | 71 | 1.5 | | | |
| 2 mM/1 h | 82 | n.p. | 2 mM/2 h | 78 | 1.6 | 2 mM/2 h | 73 | 1.6 |
| /4 h | 97 | 0.9 | /4 h | 89 | 1.8 | /8 h | 81 | 2.1 |
| /8 h | 93 | 1.1 | | | | | | |
| 4 mM/1 h | 85 | 0.7 | 4 mM/1 h | 74 | 1.5 | 4 mM/2 h | 54 | 2.0 |
| /4 h | 102 | 2.0 | /4 h | 100 | 2.1 | /4 h | 73 | 2.1 |
| | | | | | | 8 mM/1 h | 68 | 1.7 |
| | | | | | | /4 h | 81 | 2.1 |

°: 2-Mercaptoetanol (2-ME)
*: % relative to reference

As a result of these studies, mercaptoethanol and cysteine in the pH range 7-9 at concentration of 1 to 20 mM and temperatures of 20-40° C. were found to be most suitable.

In the course of further investigations, it was realized that antibody can be overreduced during exposure to the reducing agents with formation of antibody having partially reduced interchain disulfide bridges. This overreduction is reversible at atmospheric conditions when the antibody is isolated from the reaction mixture, e.g., by diafiltration as described above or by chromatography, because dissolved oxygen present in the buffers leads to spontaneous re-oxidation with re-formation of intact antibody.

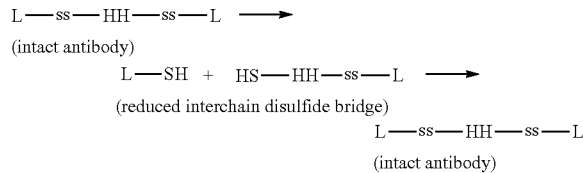

Example 1.2 (Anaerobic Conditions)

In a second set of experiments, the treatments of secukinumab antibody obtained after the Protein A capture step were performed under anaerobic conditions by using de-aerated solutions and argon or nitrogen atmosphere to exclude effects of dissolved oxygen on the reduction outcome. In brief, a secukinumab solution from a Protein A capture step was adjusted to pH 8.0 by addition of a Tris base stock solution. The solution was then adjusted to a concentration of 8 mM cysteine and 1 mM EDTA by addition of a cysteine/EDTA stock solution (e.g., 200 mM/12.5 mM EDTA at pH 8). The concentration of secukinumab in the reducing solution was 4 mg/mL (molar ratio of cysteine: antibody about 296:1). The mixture was incubated at room temperature for a period of 24 hours. At different time-points, samples were drawn and spiked with an excess of iodoacetamid, which stops the reaction by quenching sulfhydryl groups of the reducing agent and antibody.

The same set-up was used for the experiments with 2-mercaptoethanol, 2-mercaptoacetic acid, cysteine, cysteamine and glutathione. For DTT, a concentration of 1 mM was used.

The quenched samples were analyzed by capillary electrophoreses with SDS in the non-reduced mode (CE-SDS). This analytical method separates the different reduction products of antibody (HHL, HH, HL, H and L species) from intact antibody (LHHL) and quantifies them by on-line UV detection and area-integration of the obtained signals.

In FIG. 1, the data for intact antibody (LHHL) from 0, 3, 15 min, 1 h, 2 h, 4 h and 20-24 h reduction treatment shows that DTT and β-mercapto acetic acid reduce the antibody completely without re-equilibration to intact antibody. Glutathione and β-mercaptoethanol also show pronounced reduction, but were able to induce a re-equilibration to intact antibody (LHHL). Cysteine reduces the antibody to about 50%, which is followed by a straight-forward re-equilibration to intact antibody. The data for cysteamine shows that this reagent either exerts little reduction or leads very quickly (within a time of less than 3 min) to re-equilibration.

The reduction order found (i.e., DTT>β-mercapto acetic acid>β-mercaptoethanol>glutathione) correlates to published data for redox potentials or disulfide interchange. see T. Liu in "*The Proteins*, 3rd Edition, Volume 3 (1977) p. 239 which gives following comments and data:

$$\text{Redox potential } E = E_0 + 0.059 \times \log [R\text{-}SS\text{-}R]/[R\text{-}SH]$$

Standard redox potential ($E_0$ in Volt) not directly measurable as electrode is poised by the sulfur. Therefore, redox potential had to be deduced from indirect measurements:
Dithiothreitol DTT/DTTox: $E_0 \sim -0.33$ V (pH 7, 25° C.)
Glutathione GSH/GSSG: $E_0 \sim -0.24$ V (pH 7, 25° C.)
Cysteine CSH/CSSC: $E_0 \sim -0.22$ V (pH 7, 25° C.)

Example 2: Cysteine Selectively Reduces Secukinumab Under Aerobic and Anaerobic Conditions Additional experiments were performed at room temperature (RT) (about 25° C.) or 37° C. using 8 mM cysteine, 4 mg/ml secukinumab, pH 8 (molar ratio of cysteine:antibody about 295.88:1). Reactions were performed under either aerobic (i.e., preparation of the solutions and the treatment was carried out under normal air) or anaerobic (i.e., preparation of the solutions and the treatment was carried out under exclusion or reduction of oxygen by de-aeration and subsequent working under argon or nitrogen atmosphere) conditions.

Figure 2:
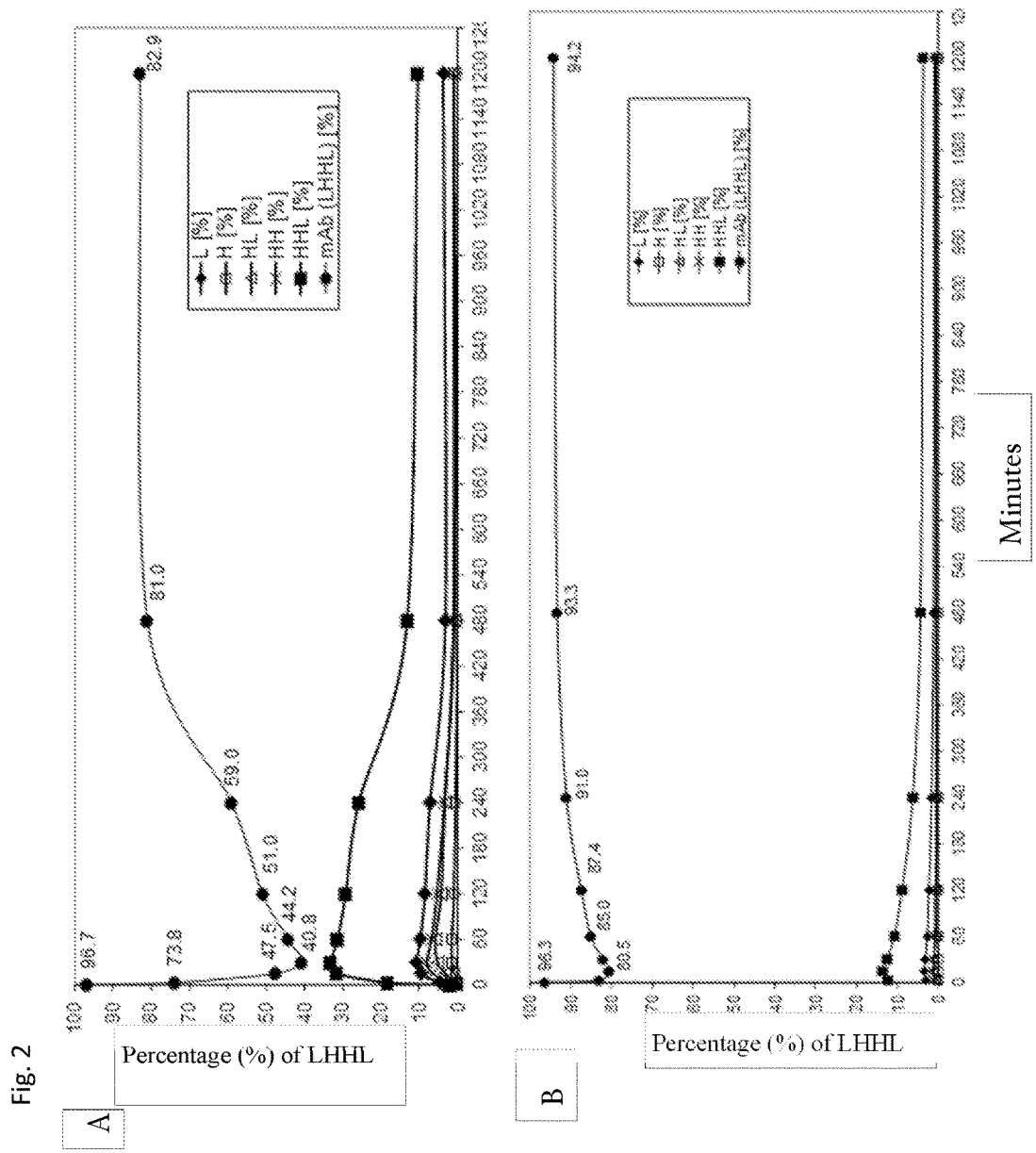
FIG. 2A shows the percentage of intact antibody (LHHL) over time at room temperature after subjection to selective reduction with 8 mM cysteine under anaerobic conditions.
FIG. 2B shows the percentage of intact antibody (LHHL) over time at room temperature after subjection to selective reduction with 8 mM cysteine under aerobic conditions.
FIG. 2C shows the percentage of intact antibody (LHHL) over time at 37° C. after subjection to selective reduction with 8 mM cysteine under anaerobic conditions.
FIG. 2D shows the percentage of intact antibody (LHHL) over time at 37° C. after subjection to selective reduction with 8 mM cysteine under aerobic conditions.
Figure 2:
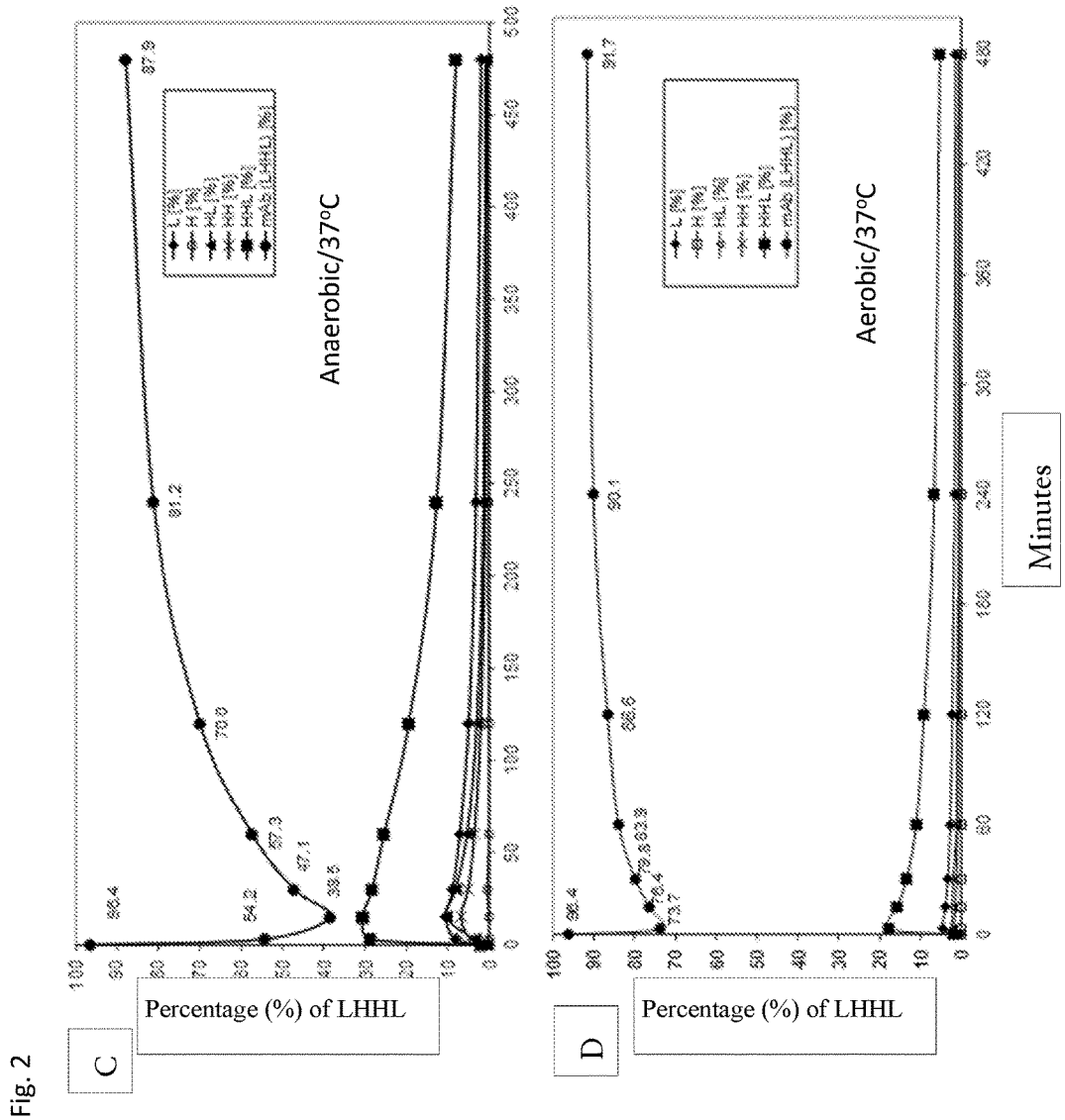

Under anaerobic conditions (e.g., nitrogen or argon atmosphere with 0% dissolved oxygen), in the early phase of the treatment there is a substantial degradation of antibody with formation of antibody fragments—a sign of over-reduction. The maximal decrease of intact antibody (LHHL) to about 40% occurs at around 15 minutes for experiments performed at either RT (FIG. 2A) or 37° C. (FIG. 2C). Re-equilibration to intact antibody at 20 hours shows about 17.1% over-reduced variants remaining in the RT samples and 12.1% over-reduced variants remaining in the 37° C. samples.

Under aerobic conditions, i.e., in presence of dissolved oxygen, there is a more moderate reaction. The maximal decrease of intact antibody (LHHL) to about 80% residual level occurs at around 15 minutes for experiments performed at RT (FIG. 2B) and to about 73% for experiments performed at 37° C. (FIG. 2D). Re-equilibration to intact antibody shows only 5.8% over-reduced variants remaining in the RT samples after 20 hours and only 9.3% over-reduced variants remaining in the 37° C. samples after 8 hours.

Thus, under anaerobic conditions the initial reduction is larger and re-equilibration to intact antibody is not as complete as under aerobic conditions.

Example 3: Influence of Dissolved Oxygen and Cystine on Selective Reduction

Because cysteine (Cys-SH) oxidizes in presence of air to cystine (Cys-SS-Cys), the difference observed under aerobic and anaerobic conditions could be caused by small amounts of cystine formed during preparation of cysteine solutions under aerobic conditions and also during the actual treatment of secukinumab with cysteine. In order to assess the influence of the level of $dO_2$ and cystine (or cystamine) on selective reduction of secukinumab, we performed several additional preparative experiments with isolation of the antibody.

For some samples, selective reduction of 4 mg/ml secukinumab was performed with 8 mM cysteine (molar ratio of cysteine:antibody 295.88:1) in a solution having a pH 8.0 at 37° C. under aerobic conditions at 100% $dO_2$ (no fumigation by nitrogen), 50%, and 20% $dO_2$ (stirring at ambient atmosphere with fumigation by nitrogen such that dissolved oxygen stayed at target level throughout the experiment), and anaerobic (0% $dO_2$) conditions (degassed solutions, full nitrogen atmosphere) without cystine, as well as under 100% $dO_2$ in presence of about 0.1 mM cystine [ratio cysteine:cystine=80:1]. In one experiment, 0.3 mM cystine was added following an initial 30 minute incubation with 8 mM cysteine under anaerobic conditions. In another experiment, selective reduction was performed under anaerobic conditions using 7.7 mM cysteine and 0.3 mM cystine [ratio cysteine:cystine=25.66:1]. In another sample, 0.1 mM cystamine was added instead of cystine.

In all these examples, samples were drawn at different time points. At the end of the treatment (240 min at 37° C.), the antibody was isolated by adjusting the pH of the bulk solution to 5.0 and loading onto a cation-exchange column that binds the antibody. After a wash to remove the reducing agent, antibody was eluted by a salt and/or pH-gradient and analyzed by CE-SDS, SE-HPLC and CEX.

Figure 3:
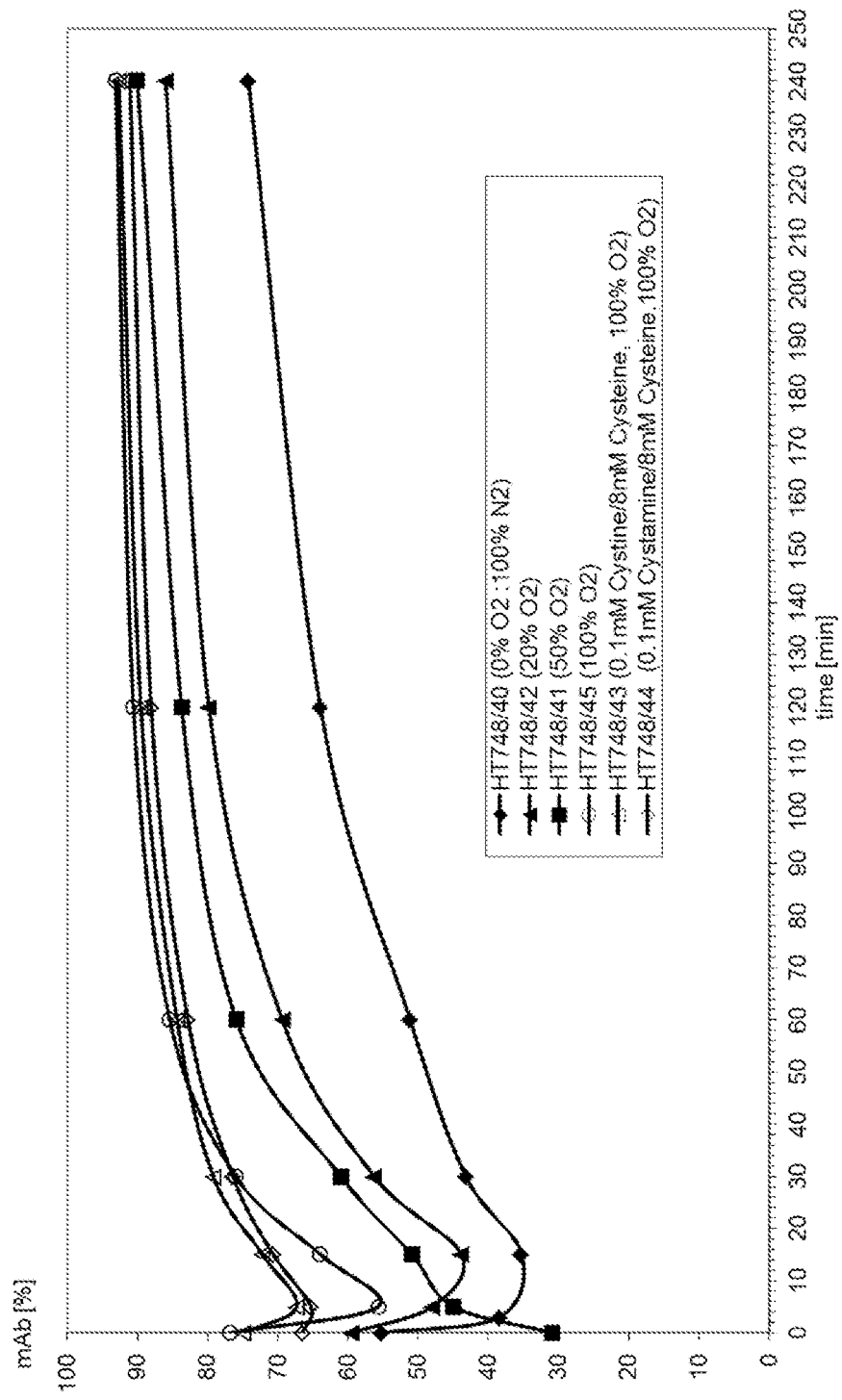
FIG. 3 shows the percentage of intact antibody over time at 37° C. temperature after subjection to selective reduction with 8 mM cysteine at various dissolved oxygen concentrations.

FIG. 3 shows CE-SDS analysis of iodacetamid quenched samples drawn at different time of the treatment. Less $dO_2$ leads to greater reduction in the early phase and slower equilibration in the later phase of selective reduction. Level of intact antibody was substantially lower (70%) at the end of treatment in total anaerobic conditions (0% $dO_2$). Level of intact antibody was improved to above 90% when the reaction was performed under conditions of 50% or more dissolved oxygen. Addition of a small amount of cystine (or cysteamine) decreased the initial reduction of antibody.

Table 3 shows activity and purity of antibody obtained after the samples from different reactivation treatments (anaerobic and aerobic conditions) were purified using subsequent chromatography on SP-Sepharose FF.

TABLE 3

Activity and purity of antibody following different reactivation treatments.

| | after SP-step | | | |
|---|---|---|---|---|
| Treatment conditions (37° C./pH 8.0/4 h) | CE-SDS purity % | SEC purity % | CEX activity % | Bio-activity % |
| Starting material | 96.4 | 98.4 | 61.2 | 45 |
| 8 mM cysteine/0% oxygene (anaerob) | 82.3 | 98.1 | 92.8 | 92 |
| 8 mM cysteine/0% oxygene/30 min: + 0.3 mM cystine | 92.6 | 98.4 | 92.3 | 95 |
| 8 mM cysteine/20% oxygene | 96.9 | 98.0 | 88.6 | 99 |
| 8 mM cysteine/50% oxygene | 96.1 | 98.2 | 87.0 | 90 |
| 8 mM cysteine/100% oxygene (aerob) | 95.8 | 98.1 | 90.6 | 96 |
| 7.7 mM cysteine/0.3 mM cystine/anaerob | 97.1 | 98.9 | 91.8 | 104 |
| 8 mM cysteine/0.1 mM cystine 100% oxygene (aerob) | 94.5 | 98.0 | 82.4 | 108 |
| 8 mM cysteine/0.1 mM cystamine 100% oxygene (aerob) | 94.8 | 98.6 | 86.1 | 86 |

With respect to bioactivity, in all cases fully active material was obtained (86-108% of theoretical maximum) versus the non-selectively reduced secukinumab starting material, which had only 45% activity. With respect to CE-SDS purity, impaired purity (82.3%) was found in antibody obtained under completely anaerobic treatment lacking cystine, which was probably due to over-reduction under these conditions (note: addition of cystine to anaerobic reactions increased the purity of the samples as measured by CE-SDS, because reduction potential is smaller and by this over-reduction less likely). However, all other selective reduction treatments led to similar, and high, antibody quality and activity. We also noted that some CE-SDS purity values prior to the SP-Sepharose chromatography step were slightly lower than the values obtained following the chromatography step (e.g., 65% before vs 82% after) (data not shown), which suggests that additional re-oxidation may occur during the chromatography step. CEX activity was generally lower under the various aerobic conditions because there was more oxygen to mitigate the reductive power of the cysteine. Addition of the oxidative agents cystine and cystamine under aerobic conditions further decreased CEX activity.

Summary and Conclusions Drawn from Examples 1-3

We have determined that CysL97 of secukinumab is available for reduction in solution, without requiring partial unfolding of the full antibody structure, e.g., using guanidine HCl. Moreover, secukinumab overall is amenable to selective reduction, which, under controlled conditions, should allow activation of the antibody without substantial degradation.

Cysteine was found to be particularly ideal for selective reduction of secukinumab, as it displayed only moderate over-reduction, coupled with fast equilibrium. In the first hour of selective reduction using cysteine, the antibody is partially reduced, e.g., up to 60% under anaerobic conditions and up to about 30% under fully-aerobic conditions. Subsequently, secukinumab slowly re-oxidizes to intact antibody. Re-oxidation of samples subjected to selective reduction with cysteine proceeded much more slowly at room temperature than reactions performed at 37° C. (c.f. 21 hours for re-equilibrium at room temperature versus 8 hrs for equilibrium at 37° C.). Room temperature samples also generally displayed smaller maximal decreases in intact antibody compared to selective reduction reactions performed at 37° C.

Under anaerobic conditions, we noted that the initial reduction of the antibody is larger and re-equilibration to intact secukinumab is not as complete as under aerobic conditions. However, addition of a small amount of cystine to anaerobic reactions resulted in improved purity and activity relative to anaerobic reactions performed in the absence of cystine. The aerobic reaction course can thus be simulated under anaerobic conditions when a small molar ratio of the oxidized from of the reducing reagent (e.g., cystine in the case of cysteine as the reducing agent) is present. Moreover, we noted that addition of cystine accelerated equilibrium of intact antibody—even when cystine was not present during the initial 30 minutes of incubation. Thus, selective reduction may be performed in the presence of air, as well as in the absence of dissolved oxygen by using an inert gas atmosphere (e.g., nitrogen or argon). If performed under fully anaerobic conditions, addition of a small molar ratio of the oxidized form of the reducing reagent is useful.

Example 4: Cysteine Selective Reduction Step Development Study: Proof of Concept (DoE1)

Example 4.1—Study Design and Methods

The main purpose of the cysteine treatment step is to regain the full biological activity of the secukinumab antibody by the masking of the —SH group of the cysteine in position 97 of the light chain, which can occur during cell cultivation, harvesting and/or Protein A chromatography. In the following Example, the purity of the antibody is analyzed by a non-reducing CE-SDS method that monitors antibody integrity (called "purity by CE-SDS") and the biologic activity of the antibody is analyzed by a cystamine-CEX chromatography method (called "activity by CEX"). In cystamine-CEX chromatography, cystamine is added to the antibody sample and allowed to derivatize any free cysteine in secukinumab. The sample is then subjected to analytical separation by cation exchange chromatography, whereby cystamine-derivatized antibody species elute after non-derivatized antibody species because they carry an additional positive charge. The chromatogram is then compared to the chromatogram of the non-treated sample. The portion of species in the chromatogram of the treated sample having a shifted elution position is a direct measure of the abundance of free CysL97-SH in the original sample and can be used as surrogate marker for activity.

The main purpose of the proof of concept study (DoE1) was to check the applicability of design of experiments studies for improving of the cysteine treatment step to test a first set of parameter ranges to identify main influencing factors and support definition of operating ranges. Additionally, DoE1 was performed to evaluate if the experimental setup is applicable to detect the influence of input parameters on output parameters. The concept study was analyzed using Modde 9.0 (Umetrics) Software.

The input parameters are shown in Table 4. The addition of cystine (oxidized form) was tested as an additional input parameter, as the redox potential is influenced by the ratio reduced form/oxidized form, in this case the ratio cysteine/cystine. The ratio cysteine/cystine and cysteine concentration were investigated on 3 levels each and the antibody concentration ("content by ALC") on 2 levels. For product quality output parameters, activity by CEC and purity by CE-SDS were determined.

TABLE 4

Input parameters.

| Name | Unit | Lower level | Medium level | Upper level |
|---|---|---|---|---|
| ratio cysteine/cystine | [-] | 2.00 | 6.00 | 10.0 |
| cysteine concentration | [mM] | 0.50 | 5.25 | 10.0 |
| content by ALC | [mg/mL] | 3.25 | n.a. | 6.5 |

The design is a $3^2 \times 2$ Multilevel Factorial Design without center point runs. The design was chosen to gain data and process understanding for improving the cysteine treatment step. This type of design supports calculation of mathematical models with linear, interaction and quadratic terms for the input parameters ratio cysteine/cystine and cysteine concentration. The experimental design plan is given in Table 5.

TABLE 5

Experimental design plan. The relative molecular mass of secukinumab, based on amino acid sequence, is 147,944 Daltons, which is used to calculate the molar ratio of cysteine to protein.

| RUN | Ratio cysteine to cystine [M/M] | Cysteine concentration [mM] | Protein Content by ALC [mg/mL] | Approx. molar ratio cysteine to protein [M/M] |
|---|---|---|---|---|
| React007_1 | 2 | 0.50 | 6.50 | 11.38 |
| React007_2 | 6 | 10.00 | 6.50 | 227.61 |
| React007_3 | 2 | 10.00 | 6.50 | 227.61 |
| React007_4 | 10 | 10.00 | 6.50 | 227.61 |
| React007_6 | 6 | 0.50 | 6.50 | 11.38 |
| React007_7 | 10 | 10.00 | 3.25 | 455.21 |
| React007_8 | 10 | 5.25 | 6.50 | 119.49 |
| React007_9 | 6 | 10.00 | 3.25 | 455.21 |
| React007_10 | 6 | 5.25 | 6.50 | 119.49 |
| React007_11 | 2 | 10.00 | 3.25 | 455.21 |
| React007_12 | 10 | 0.50 | 3.25 | 22.76 |
| React007_13 | 6 | 5.25 | 3.25 | 238.99 |
| React007_14 | 6 | 0.50 | 3.25 | 22.76 |
| React007_15 | 10 | 5.25 | 3.25 | 238.99 |
| React007_16 | 2 | 5.25 | 3.25 | 238.99 |
| React007_17 | 2 | 0.50 | 3.25 | 22.76 |
| React007_18 | 10 | 0.50 | 6.50 | 11.38 |

The selective reduction reactions were performed in 15 mL closed polypropylene tubes, which were placed in a water bath and warmed to 37° C. The protein solution was diluted to the target concentration with WFI and pH was adjusted to pH 8.0 with 1 M Tris. After addition of the cysteine and cystine solution the tubes were tempered and incubated in a water bath for 4 h. Then samples were withdrawn for determination of content by ALC. CE-SDS was performed with samples, which were withdrawn directly after incubation and the reaction was stopped by addition of a 10-fold excess (related to cysteine concentration) of iodoacetamide. The remaining solution was cooled to ambient temperature, the pH was adjusted to pH 5.0-5.5 and samples were withdrawn for CEX and SEC analytics.

The design was carried out according to the actual experimental design in Table 6.

TABLE 6

Actual experimental design. The relative molecular mass of secukinumab, based on amino acid sequence, is 147,944 Da, which is used to calculate the molar ratio of cysteine to protein.

| Run | Molar ratio cysteine to cystine [M/M] | Cysteine concentration [mM] | Protein Content by ALC [mg/mL] | Approx. molar ratio cysteine to protein [M/M] |
|---|---|---|---|---|
| React007_1 | 2 | 0.50 | 6.9 | 10.72 |
| React007_2 | 6 | 10.00 | 6.3 | 234.83 |
| React007_3 | 2 | 10.00 | 6.3 | 234.83 |
| React007_4 | 10 | 10.00 | 6.3 | 234.83 |
| React007_5 | 2 | 5.25 | 6.5 | 119.49 |
| React007_6 | 6 | 0.50 | 6.8 | 10.88 |
| React007_7 | 10 | 10.00 | 3.2 | 462.33 |
| React007_8 | 10 | 5.25 | 6.5 | 119.49 |
| React007_9 | 6 | 10.00 | 3.2 | 462.33 |
| React007_10 | 6 | 5.25 | 6.6 | 117.68 |
| React007_11 | 2 | 10.00 | 3.2 | 462.33 |
| React007_12 | 10 | 0.50 | 3.5 | 21.13 |
| React007_13 | 6 | 5.25 | 3.4 | 228.44 |
| React007_14 | 6 | 0.50 | 3.5 | 21.13 |
| React007_15 | 10 | 5.25 | 3.3 | 235.37 |
| React007_16 | 2 | 5.25 | 3.4 | 228.44 |
| React007_17 | 2 | 0.50 | 3.5 | 21.13 |
| React007_18 | 10 | 0.50 | 6.6 | 11.21 |

Example 4.2—Results of Proof of Concept Study

The values for the output parameters are listed in Table 7 together with the input parameters. The runs are listed with ascending values for activity by CEX. It can be seen that all runs with 0.5 mM concentration of cysteine have lower activities—probably because this cysteine concentration is too low to achieve complete unmasking of Cys97. In this set, a slight improvement in activity by CEX was noted when the ratio of cysteine:antibody was increased from about 11:1 to 21:1 (REACT00_17, _14 and _12). Of these three runs, those with a slightly higher ratio of cysteine:cystine (RE-ACT007_14 and _12) (probably representing slight mitigation in the reductive power of cysteine) also had good purity by CE-SDS parameter. Then, there is a series of runs where the difference in activity output parameter is small (92.4 to 93.1%) and probably within the analytical accuracy, making interpretation among this group difficult. Finally, there is a set of 4 runs where the activity was the highest (93.7 to 95.1%). Notably, these runs did not contain the highest cysteine/protein ratio (462.33).

TABLE 7

Input and output parameter values listed with ascending values for activity by CEX

| Run | Molar ratio cysteine to cystine [M/M] | Cysteine concentration [mM] | Protein content by ALC [mg/mL] | Approx. molar ratio cysteine to protein [M/M] | activity by CEX [%] | purity by CE-SDS [%] |
|---|---|---|---|---|---|---|
| React007_1 | 2 | 0.50 | 6.9 | 10.72 | 87.2 | 97.0 |
| React007_6 | 6 | 0.50 | 6.8 | 10.88 | 88.8 | 95.0 |
| React007_18 | 10 | 0.50 | 6.6 | 11.21 | 88.8 | 94.0 |
| React007_17 | 2 | 0.50 | 3.5 | 21.13 | 89.3 | 78.0 |
| React007_14 | 6 | 0.50 | 3.5 | 21.13 | 90.4 | 93.0 |
| React007_12 | 10 | 0.50 | 3.5 | 21.13 | 90.9 | 95.0 |
| React007_16 | 2 | 5.25 | 3.4 | 228.44 | 92.4 | 85.0 |
| React007_3 | 2 | 10.00 | 6.3 | 234.83 | 92.8 | 83.0 |
| React007_13 | 6 | 5.25 | 3.4 | 228.44 | 92.8 | 85.0 |
| React007_9 | 6 | 10.00 | 3.2 | 462.33 | 92.9 | 68.0 |
| React007_7 | 10 | 10.00 | 3.2 | 462.33 | 93.0 | 56.0 |
| React007_8 | 10 | 5.25 | 6.5 | 119.49 | 93.0 | 88.0 |
| React007_11 | 2 | 10.00 | 3.2 | 462.33 | 93.0 | 70.0 |
| React007_4 | 10 | 10.00 | 6.3 | 234.83 | 93.1 | 77.0 |
| React007_2 | 6 | 10.00 | 6.3 | 234.83 | 93.7 | 76.0 |
| React007_15 | 10 | 5.25 | 3.3 | 235.37 | 94.0 | 78.0 |
| React007_10 | 6 | 5.25 | 6.6 | 117.68 | 94.2 | 84.0 |
| React007_5 | 2 | 5.25 | 6.5 | 119.49 | 95.2 | 87.0 |

Figure 4:
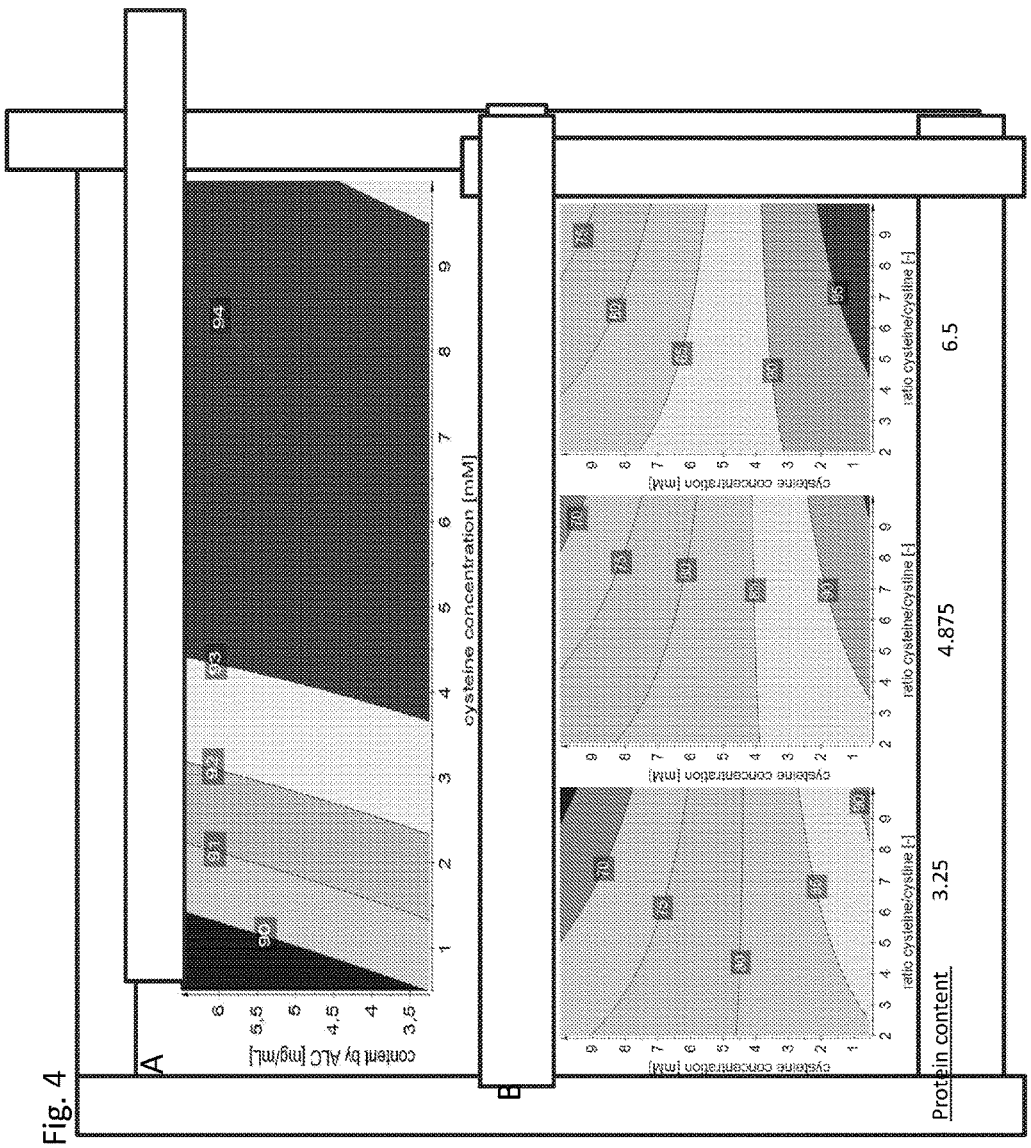
FIG. 4A shows a 4D contour plot for activity by CEX.
FIG. 4B shows a 4D contour plot for purity for CE-SDS. The plots of FIG. 4 analyze the impact of and interaction of cysteine concentration, protein content and ratio of cysteine/cysteine on the output parameters activity by CEX and purity by CE-SDS.

Because of a good model fit it was possible to use contour plots to understand the main influencing parameters of the system. The quality of the models is represented by 4 tools, namely the $R^2$, $Q^2$, Model validity and the Standard Deviation (SD) of replicates. A model that is in good agreement with the data will have a $R^2$ and $Q^2$ close to 1.0 and Model validity above 0.25. Models with lower statistical significance have lower $R^2$ and $Q^2$ values. The model diagnostics for the quality output parameters indicate that the models for activity by CEX and purity by CE-SDS have high statistical significance ($R^2=0.88$ and $Q^2=0.73$ for activity by CEX and $R^2=0.84$ and $Q^2=0.63$ for purity by CE-SDS). The contour plot for activity by CEX (FIG. 4A) teaches that activity by CEX values equal or higher than 93.0% are achieved if the input parameter cysteine concentration is between 4.0 mM and 9.0 mM. Furthermore, the input factor content by ALC can vary from the low level (3.25 mg/mL) to the high level (6.5 mg/mL) when the input factor ratio cysteine/cystine is set to its center point of 6. To improve activity by CEX, the model indicates that the input parameter content by ALC should be higher than the investigated upper level of 6.5 mg/mL.

In Table 8, the runs are listed according to increasing CE-SDS purity. Three groups can be seen: runs with lower purity (</=70%), to which the runs with the high molar ratio of 462 Mol/Mol belong; runs with medium purity (70-83%); and runs with higher purity (>83%). Due to a good model fit, it is possible to also use a contour plot to understand how the input parameter influence the purity by CE-SDS values shown in Table 8. According to the contour plot for CE-SDS in FIG. 4B, the area that comes closest to the theoretical optimum lies at the right lower side. This implies that the ratio cysteine/cystine should be set at a higher level and the cysteine concentration should be set to a lower level. Additionally, a higher content by ALC could be used to increase the purity by CE-SDS.

TABLE 8

Input and output parameters listed according to increasing CE-SDS purity.

| Run | Molar ratio cysteine to cystine [M/M] | Cysteine concentration [mM] | Protein content by ALC [mg/mL] | Approx. molar ratio cysteine to protein [M/M] | Activity by CEX [%] | Purity by CE-SDS [%] |
|---|---|---|---|---|---|---|
| React007_7 | 10 | 10.00 | 3.2 | 462.33 | 93.0 | 56 |
| React007_9 | 6 | 10.00 | 3.2 | 462.33 | 92.9 | 68 |
| React007_11 | 2 | 10.00 | 3.2 | 462.33 | 93.0 | 70 |
| React007_2 | 6 | 10.00 | 6.3 | 234.83 | 93.7 | 76 |
| React007_4 | 10 | 10.00 | 6.3 | 234.83 | 93.1 | 77 |
| React007_15 | 10 | 5.25 | 3.3 | 235.37 | 94.0 | 78 |
| React007_3 | 2 | 10.00 | 6.3 | 234.83 | 92.8 | 83 |
| React007_10 | 6 | 5.25 | 6.6 | 117.68 | 94.2 | 84 |
| React007_16 | 2 | 5.25 | 3.4 | 228.44 | 92.4 | 85 |
| React007_13 | 6 | 5.25 | 3.4 | 228.44 | 92.8 | 85 |
| React007_5 | 2 | 5.25 | 6.5 | 119.49 | 95.2 | 87 |
| React007_8 | 10 | 5.25 | 6.5 | 119.49 | 93.0 | 88 |
| React007_14 | 6 | 0.50 | 3.5 | 21.13 | 90.4 | 93 |
| React007_18 | 10 | 0.50 | 6.6 | 11.21 | 88.8 | 94 |
| React007_6 | 6 | 0.50 | 6.8 | 10.88 | 88.8 | 95 |
| React007_12 | 10 | 0.50 | 3.5 | 21.13 | 90.9 | 95 |
| React007_1 | 2 | 0.50 | 6.9 | 10.72 | 87.2 | 97 |

Example 4.3—Summary of Proof of Concept Study

The proof of concept study confirmed the applicability of the experimental setup to evaluate and refine the input parameters of the cysteine treatment step. We noted that a high molar ratio of cysteine to protein can lead to low values of purity by CE-SDS. The models also suggested that increasing protein and cysteine concentration might improve purity by CE-SDS and activity by CEX. Thus, cysteine concentration and the influence of an increased parameter range for content by ALC on the product quality attributes activity by CEX and purity by CE-SDS was evaluated in more detail in the following study (Response Surface Design 1).

Example 5: Cysteine Selective Reduction Step Development Study: Response Surface Design 1

Example 5.1—Study Design and Methods

Based on the data from Example 4, the input parameters of the selective reduction step were adjusted. The development study was analyzed using Modde 9.0 (Umetrics) Software. The input parameters are listed in Table 9. The factors are investigated on three levels each. The design was an adjusted version of the proof of concept study with adjusted levels of the input parameters content by ALC and cysteine concentration. The input parameter "ratio cysteine/cystine" was replaced by the parameter "concentration of cystine" to simplify the experimental setup and further the data evaluation.

TABLE 9

Input parameters.

| Name | Unit | Lower level | Medium level | Upper level |
|---|---|---|---|---|
| Cystine concentration | [mM] | 0.0 | 0.5 | 1.0 |
| cysteine concentration | [mM] | 4.0 | 9.0 | 14.0 |
| content by ALC | [mg/mL] | 3.8 | 11.6 | 19.5 |

The design is a $2^3$ Center Composite Face (CCF) design with 4 center runs at center point conditions. This type of design supports calculation of mathematical models with linear, interaction and quadratic terms. The experimental design plan is given in Table 10.

TABLE 10

Experimental design plan. 1) Center points. The relative molecular mass of secukinumab, based on amino acid sequence, is 147,944 Da, which is used to calculate the molar ratio of cysteine to protein.

| Run | Protein content by ALC (mg/mL) | Cysteine concentration (mM) | Cystine concentration (mM) | Molar ratio cysteine to cystine (M/M) | Approx. molar ratio cysteine to protein (M/M) |
|---|---|---|---|---|---|
| React016_1 | 19.5 | 14 | 0.0 | NA | 106.22 |
| React016_2[1] | 11.6 | 9 | 0.5 | 18 | 114.78 |
| React016_3 | 3.8 | 9 | 0.5 | 18 | 350.39 |
| React016_4 | 11.6 | 9 | 1.0 | 9 | 114.78 |
| React016_5 | 19.5 | 9 | 0.5 | 18 | 68.28 |
| React016_6 | 19.5 | 4 | 0.0 | NA | 30.35 |
| React016_7 | 3.8 | 4 | 1.0 | 4 | 155.73 |
| React016_8[1] | 11.6 | 9 | 0.5 | 18 | 114.78 |
| React016_9 | 11.6 | 14 | 0.5 | 28 | 178.55 |
| React016_10 | 3.8 | 4 | 0.0 | NA | 155.73 |
| React016_11 | 11.6 | 4 | 0.5 | 8 | 51.02 |
| React016_12 | 3.8 | 14 | 0.0 | NA | 545.06 |
| React016_13 | 19.5 | 4 | 1.0 | 4 | 30.35 |
| React016_14[1] | 11.6 | 9 | 0.5 | 18 | 114.78 |
| React016_15[1] | 11.6 | 9 | 0.5 | 18 | 114.78 |
| React016_16 | 19.5 | 14 | 1.0 | 14 | 106.22 |
| React016_17 | 11.6 | 9 | 0.0 | NA | 114.78 |
| React016_18 | 3.8 | 14 | 1.0 | 14 | 545.06 |

The selective reduction reactions were performed in 15 mL closed polypropylene tubes, which were placed in a water bath and warmed to 37° C. The design was carried out according to the actual experimental design in Table 11.

TABLE 11

Actual experimental design. 1) Center point; 2) This experiment is not regarded as a center point of the used DoE software, due to a deviation of more than 10% protein concentration from the originally planned center point. The relative molecular mass of secukinumab, based on amino acid sequence, is 147,944 Da, which is used to calculate the molar ratio of cysteine to protein.

| Run | Protein content by ALC (mg/mL) | Cysteine concentration (mM) | Cystine concentration (mM) | Molar ratio cysteine to cystine (M/M) | Approx. molar ratio cysteine to protein (M/M) |
|---|---|---|---|---|---|
| React016_1 | 19.5 | 14 | 0.0 | NA | 106.22 |
| React016_2[1] | 11.9 | 9 | 0.5 | 18 | 111.89 |
| React016_3 | 4.0 | 9 | 0.5 | 18 | 332.87 |
| React016_4 | 11.5 | 9 | 1.0 | 9 | 115.78 |
| React016_5 | 19.4 | 9 | 0.5 | 18 | 68.63 |
| React016_6 | 19.4 | 4 | 0.0 | NA | 30.50 |
| React016_7 | 3.8 | 4 | 1.0 | 4 | 155.73 |
| React016_8[1] | 11.6 | 9 | 0.5 | 18 | 114.78 |
| React016_9 | 11.5 | 14 | 0.5 | 28 | 180.11 |
| React016_10 | 3.7 | 4 | 0.0 | NA | 159.94 |
| React016_11 | 11.6 | 4 | 0.5 | 8 | 51.02 |
| React016_12 | 3.8 | 14 | 0.0 | NA | 545.06 |
| React016_13 | 19.3 | 4 | 1.0 | 4 | 30.66 |
| React016_14[1] | 11.7 | 9 | 0.5 | 18 | 113.80 |
| React016_15[1,2] | 11.1 | 9 | 0.5 | 18 | 119.95 |
| React016_16 | 17.8 | 14 | 1.0 | 14 | 116.36 |
| React016_17 | 10.9 | 9 | 0.0 | NA | 122.16 |
| React016_18 | 3.8 | 14 | 1.0 | 14 | 545.06 |

Example 5.2—Results of Response Surface Design 1

The input parameters and values for the output parameters are listed in Table 12. The runs are listed according increasing activity by CEX. It can be seen that runs with high CEX activity used higher cysteine concentration. The single run with lower activity (React016_13) had high protein concentration, low cysteine concentration and high cystine concentration.

The model diagnostics for the product quality output parameter were $R^2=0.95$, $Q^2=0.76$, SD=0.20, and Model validity=0.78 for the activity by CEX and $R^2=0.79$, $Q^2=0.53$, SD=2.91, and Model validity=0.83 for purity by CE-SDS, indicating significant models for both output parameters. Contour plots were calculated (FIG. 5), to gain more insight into the impact of the input parameter settings and the impact on activity by CEX.

TABLE 12

Input and output parameters listed according increasing activity by CEX.

| Run | Protein content by ALC (mg/mL) | Cysteine concen- tration (mM) | Cystine concen- tration (mM) | Molar ratio cysteine to cystine (M/M) | Approx. molar ratio cysteine to protein (M/M) | Activity by CEX [%] | Purity by CE-SDS [%] |
|---|---|---|---|---|---|---|---|
| React016_13 | 19.3 | 4 | 1 | 4 | 30.66 | 91.6 | 93 |
| React016_7 | 3.8 | 4 | 1.0 | 4 | 155.73 | 93.3 | 92 |
| React016_6 | 19.4 | 4 | 0.0 | NA | 30.50 | 93.5 | 94 |
| React016_11 | 11.6 | 4 | 0.5 | 8 | 51.02 | 93.5 | 93 |
| React016_5 | 19.4 | 9 | 0.5 | 18 | 68.63 | 94.1 | 85 |
| React016_10 | 3.7 | 4 | 0.0 | NA | 159.94 | 94.2 | 79 |
| React016_2[1] | 11.9 | 9 | 0.5 | 18 | 111.89 | 94.3 | 86 |
| React016_3 | 4.0 | 9 | 0.5 | 18 | 332.87 | 94.3 | 85 |
| React016_4 | 11.5 | 9 | 1.0 | 9 | 115.78 | 94.5 | 87 |
| React016_8[1] | 11.6 | 9 | 0.5 | 18 | 114.78 | 94.5 | 91 |
| React016_15[1,2] | 11.1 | 9 | 0.5 | 18 | 119.95 | 94.5 | 86 |
| React016_14[1] | 11.7 | 9 | 0.5 | 18 | 113.80 | 94.7 | 86 |
| React016_17 | 10.9 | 9 | 0.0 | NA | 122.16 | 94.7 | 85 |
| React016_1 | 19.5 | 14 | 0.0 | NA | 106.22 | 94.9 | 76 |
| React016_9 | 11.5 | 14 | 0.5 | 28 | 180.11 | 95.1 | 85 |
| React016_12 | 3.8 | 14 | 0.0 | NA | 545.06 | 95.1 | 74 |
| React016_16 | 17.8 | 14 | 1.0 | 14 | 116.36 | 95.1 | 78 |
| React016_18 | 3.8 | 14 | 1.0 | 14 | 545.06 | 95.1 | 77 |

[1]Center points;
[2]This experiment is not regarded as a center point of the used DoE software, due to a deviation of more than 10% protein concentration from the originally planned center point.

Figure 5:
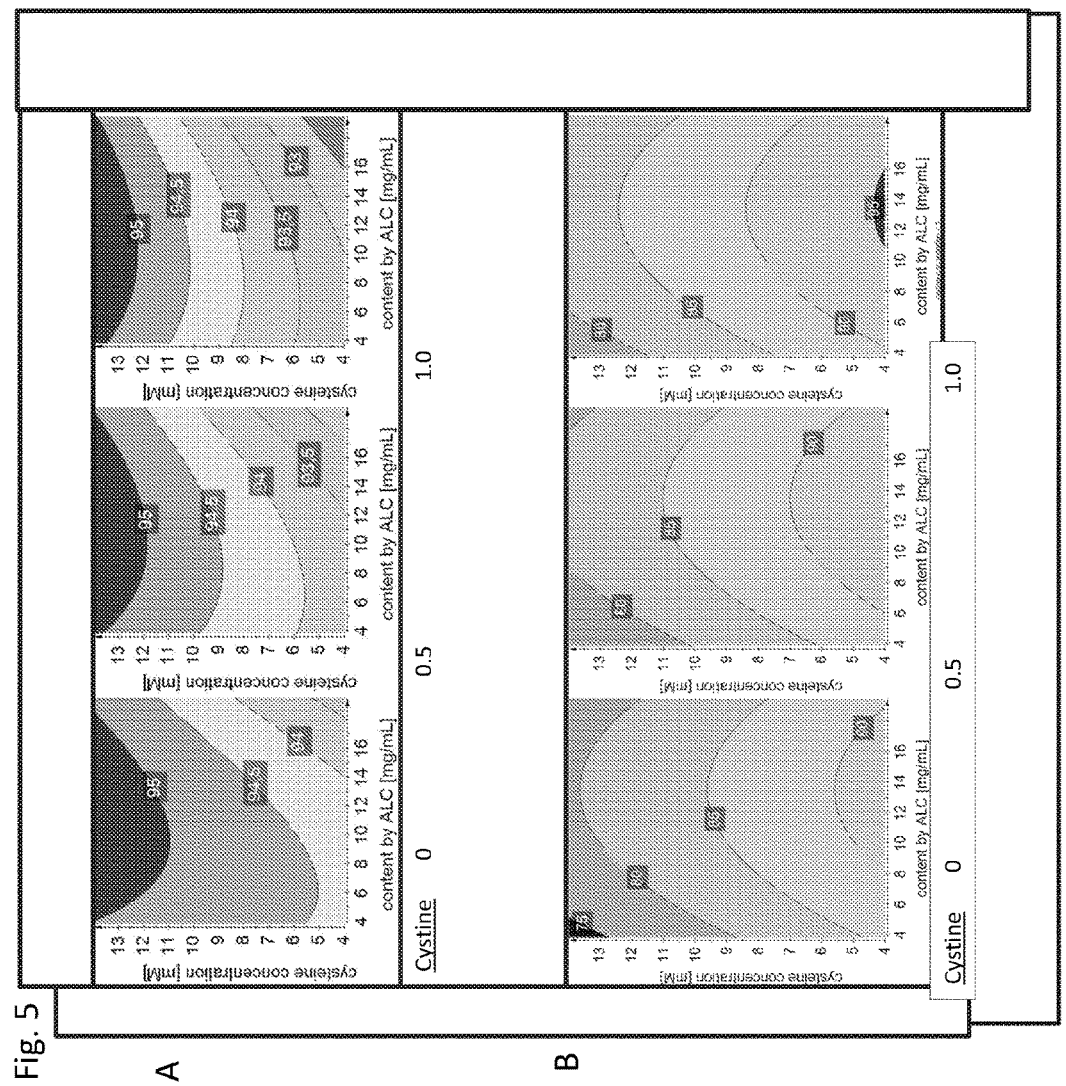
FIG. 5A shows a 4D contour plot for activity by CEX.
FIG. 5B shows a 4D contour plot for purity for CE-SDS. The plots of FIG. 5 analyze the impact of and interaction of cysteine concentration, protein content and cystine concentration on the output parameters activity by CEX and purity by CE-SDS.

As shown in the contour plot in FIG. 5, to achieve a high activity by CEX, the most influential input parameter is the cysteine concentration, which should be set to its high level. But, even at the low level of cysteine concentration high CEX activity (>93%) is met if the content by ALC and the cystine concentration are not at the upper limit. The input parameters content by ALC and cystine concentration also have influence on the output parameter activity by CEX, but to a smaller extent.

In Table 13 the runs are listed according to ascending CE-SDS purity. The runs can be divided into three groups. There was a series of six runs (mainly the 14 mM runs) with low purity (<80%), a series of runs with medium purity (85-91%), and a series of runs with higher purity (>91%), the later all being 4 mM cysteine runs.

suggested that content by ALC should be set to 12 mg/mL as ideal. The cysteine concentration has an ideal at 4.0 mM in this particular experiment. For the cystine concentration, the ideal is 0.32 mM.

According to the results of this study, the cysteine treatment step is mainly influenced by the cysteine concentration. High cysteine concentration promotes high activity by CEX, but leads simultaneously to low purity by CE-SDS. According to the design space estimator, the cysteine con-

TABLE 13

Input and output parameters listed according to ascending CE-SDS purity.

| Run | Protein content by ALC (mg/mL) | Cysteine concentration (mM) | Cystine concentration (mM) | Molar ratio cysteine to cystine (M/M) | Approx. molar ratio cysteine to protein (M/M) | Activity by CEX [%] | Purity by CE-SDS [%] |
|---|---|---|---|---|---|---|---|
| React016_12 | 3.8 | 14 | 0.0 | NA | 545.06 | 95.1 | 74 |
| React016_1 | 19.5 | 14 | 0.0 | NA | 106.22 | 94.9 | 76 |
| React016_18 | 3.8 | 14 | 1.0 | 14 | 545.06 | 95.1 | 77 |
| React016_16 | 17.8 | 14 | 1.0 | 14 | 116.36 | 95.1 | 78 |
| React016_10 | 3.7 | 4 | 0.0 | NA | 159.94 | 94.2 | 79 |
| React016_5 | 19.4 | 9 | 0.5 | 18 | 68.63 | 94.1 | 85 |
| React016_3 | 4.0 | 9 | 0.5 | 18 | 332.87 | 94.3 | 85 |
| React016_17 | 10.9 | 9 | 0.0 | NA | 122.16 | 94.7 | 85 |
| React016_9 | 11.5 | 14 | 0.5 | 28 | 180.11 | 95.1 | 85 |
| React016_2[1] | 11.9 | 9 | 0.5 | 18 | 111.89 | 94.3 | 86 |
| React016_15[1,2] | 11.1 | 9 | 0.5 | 18 | 119.95 | 94.5 | 86 |
| React016_14[1] | 11.7 | 9 | 0.5 | 18 | 113.80 | 94.7 | 86 |
| React016_4 | 11.5 | 9 | 1.0 | 9 | 115.78 | 94.5 | 87 |
| React016_8[1] | 11.6 | 9 | 0.5 | 18 | 114.78 | 94.5 | 91 |
| React016_7 | 3.8 | 4 | 1.0 | 4 | 155.73 | 93.3 | 92 |
| React016_13 | 19.3 | 4 | 1.0 | 4 | 30.66 | 91.6 | 93 |
| React016_11 | 11.6 | 4 | 0.5 | 8 | 51.02 | 93.5 | 93 |
| React016_6 | 19.4 | 4 | 0.0 | NA | 30.50 | 93.5 | 94 |

[1]Center points;
[2]This experiment is not regarded as a center point of the used DoE software, due to a deviation of more than 10% protein concentration from the originally planned center point.

Based on the results the cysteine concentration should be low and the content by ALC and cystine concentration set to high to achieve higher purity by CE-SDS values.

The experiments React016_6, React016_7, React016_8 and React016_11 have high values for both two quality output parameters. To estimate the risk of failure of the cysteine treatment step based on the model established by this DoE, a design space estimator using Monte Carlo simulations was performed. The design space estimator provides a range where the factors can vary within, while the output parameters do not exceed the target range for product quality and process performance output parameter. It is centration should be kept at 4 mM and the content by ALC should be set to 12 mg/mL (ratio cysteine to protein of about 49).

For verification of the results of the statistical designs, target runs were performed in stirred 2L-bioreactors having an air overlay and open headspace. No stirring was applied during incubation. The process parameters are listed in Table 14 and the analytical results are shown in Table 15.

TABLE 14

Process parameters of target runs. The relative molecular mass of secukinumab, based on amino acid sequence, is 147,944 Da, which is used to calculate the molar ratio of cysteine to protein.

| Process parameter | Unit | Target run 1 (REACT019) | Target run 2 (REACT020) | Target run 3 (REACT021) |
|---|---|---|---|---|
| Protein concentration | [mg/mL] | 12.90 | 13.00 | 12.60 |
| Cysteine concentration | [mM] | 4.00 | 8.00 | 4.00 |
| Cystine concentration | [mM] | 0.15 | 0.15 | 0.00 |
| Temperature | [° C.] | 37.00 | 37.00 | 37.00 |
| pH | [-] | 8.00 | 8.00 | 8.00 |
| Incubation time | [h] | 4.00 | 4.00 | 4.00 |
| Molar ratio cysteine/cystine | M/M | 26.67 | 53.33 | n.a. |
| Approx. molar ratio cysteine to protein | M/M | 45.87 | 91.04 | 46.97 |

TABLE 15

Analytical Results of target runs.

| Process parameter | Unit | Target run 1 (REACT019) | Target run 2 (REACT020) | Target run 3 (REACT021) |
|---|---|---|---|---|
| Activity by CEX | [%] | 94.8 | 94.3 | 95.4 |
| Purity by CE-SDS | [%] | 94.0 | 89.0 | 95.0 |

All three runs lead to similar results regarding activity by CEX. This corresponds to the results of the previous DoE study indicating that 4.0 mM cysteine is sufficient to regain the activity of the antibody. In the 3rd target run (REACT021) the cystine was omitted, leading to comparable results for purity by CE-SDS with run 1 (REACT019) and demonstrating that, under the conditions tested, cystine has only minor influence on performance of the cysteine treatment step. An increase of the cysteine concentration to 8.0 mM (ratio of cysteine to protein of about 91) led, not to higher values of activity by CEX, but to lower purity by CE-SDS in the pool, falling below the development target of 90%. Although cystine showed significance in the statistical design, a positive effect was not detectable in the target runs. Additionally, the influence in the statistical design on activity by CEX is minor (see FIG. 5) and preparation of a cystine containing buffer is difficult due to the low solubility of cystine in non-basic buffers. Hence, cystine can be omitted in the cysteine treatment buffer.

Example 6: Cysteine Selective Reduction Step Development Study: Response Surface Design 2

Example 6.1-Study Design and Methods

The main purpose of the response surface design 2 (DoE3) was the investigation of the process parameters temperature, time and pH on the cysteine treatment step in addition to the cysteine concentration. The data are also used to support definition of operating ranges and identify main influencing factors. The development study was analyzed using Modde 9.0 (Umetrics) Software. The input parameters are found in Table 16.

TABLE 16

Input parameters.

| Name | Unit | Lower level | Medium level | Upper level |
|---|---|---|---|---|
| temperature | [° C.] | 32.0 | 37.0 | 42.0 |
| time | [h] | 1.0 | 4.0 | 7.0 |
| pH | [-] | 7.5 | 8.0 | 8.5 |
| cysteine concentration | [mM] | 2.0 | 5.0 | 8.0 |

The design is a Central Composite Face (CCF) design with 3 center point runs. The experimental design plan is given in Table 17. The design was chosen to evaluate the influence of additional process parameters, as the cysteine treatment solution was improved in the former experiments. The cysteine concentration was analyzed again as it was the most influencing input parameter on the cysteine treatment step and interactions with the input parameters were expected. This type of design supports calculation of mathematical models with linear, interaction and quadratic terms.

TABLE 17

Experimental design plan.

| Run | Temperature [° C.] | Time (h) | pH [-] | Cysteine concentration [mM] | Protein content by ALC [mg/mL] | Approx. molar ratio of cysteine to protein (M/M) |
|---|---|---|---|---|---|---|
| React027_1 | 42 | 7 | 8.5 | 8 | 13 | 91.04 |
| React027_2 | 37 | 4 | 8.0 | 8 | 13 | 91.04 |
| React027_3 | 32 | 1 | 7.5 | 8 | 13 | 91.04 |
| React027_4 | 32 | 1 | 8.5 | 2 | 13 | 22.76 |
| React027_5[1] | 37 | 4 | 8.0 | 5 | 13 | 56.90 |
| React027_6 | 42 | 1 | 8.5 | 8 | 13 | 91.04 |
| React027_7 | 32 | 1 | 8.5 | 8 | 13 | 91.04 |
| React027_8 | 32 | 1 | 7.5 | 2 | 13 | 22.76 |
| React027_9[1] | 37 | 4 | 8.0 | 5 | 13 | 56.90 |
| React027_10 | 37 | 7 | 8.0 | 5 | 13 | 56.90 |
| React027_11 | 42 | 7 | 7.5 | 2 | 13 | 22.76 |
| React027_12 | 42 | 4 | 8.0 | 5 | 13 | 56.90 |
| React027_13 | 32 | 7 | 7.5 | 8 | 13 | 91.04 |
| React027_14 | 37 | 4 | 8.0 | 2 | 13 | 22.76 |
| React027_15 | 37 | 4 | 7.5 | 5 | 13 | 56.90 |
| React027_16 | 32 | 4 | 8.0 | 5 | 13 | 56.90 |
| React027_17 | 42 | 1 | 8.5 | 2 | 13 | 22.76 |
| React027_18 | 32 | 7 | 7.5 | 2 | 13 | 22.76 |
| React027_19 | 37 | 1 | 8.0 | 5 | 13 | 56.90 |
| React027_20 | 42 | 7 | 7.5 | 8 | 13 | 91.04 |
| React027_21 | 42 | 1 | 7.5 | 8 | 13 | 91.04 |
| React027_22[1] | 37 | 4 | 8.0 | 5 | 13 | 56.90 |
| React027_23 | 42 | 7 | 8.5 | 2 | 13 | 22.76 |
| React027_24 | 32 | 7 | 8.5 | 2 | 13 | 22.76 |
| React027_25 | 37 | 4 | 8.5 | 5 | 13 | 56.90 |
| React027_26 | 32 | 7 | 8.5 | 8 | 13 | 91.04 |
| React027_27 | 42 | 1 | 7.5 | 2 | 13 | 22.76 |

[1]Center points. The relative molecular mass of secukinumab, based on amino acid sequence, is 147,944 Da, which is used to calculate the molar ratio of cysteine to protein.

The selective reduction reactions were performed in 15 mL closed polypropylene tubes, which were placed in a water bath and warmed to 37° C.

Example 6.2—Results of Response Surface Design 2

The study was carried out according to the actual experimental design in Table 18.

TABLE 18

Actual experimental design plan.

| Run | Temperature [° C.] | Time (h) | pH [-] | Cysteine concentration [mM] | Protein content by ALC [mg/mL] | Approx. molar ratio of cysteine to protein (M/M) |
|---|---|---|---|---|---|---|
| React027_1 | 42 | 7 | 8.5 | 8 | 13 | 91.04 |
| React027_2 | 37 | 4 | 8.0 | 8 | 13 | 91.04 |
| React027_3 | 32 | 1 | 7.5 | 8 | 13 | 91.04 |
| React027_4 | 32 | 1 | 8.4 | 2 | 13 | 22.76 |
| React027_5[1,2] | 37 | 4 | 7.9 | 5 | 13 | 56.90 |
| React027_6 | 42 | 1 | 8.5 | 8 | 13 | 91.04 |
| React027_7 | 32 | 1 | 8.5 | 8 | 13 | 91.04 |
| React027_8 | 32 | 1 | 7.3 | 2 | 13 | 22.76 |
| React027_91 | 37 | 4 | 8.0 | 5 | 13 | 56.90 |
| React027_10 | 37 | 7 | 8.0 | 5 | 13 | 56.90 |
| React027_11 | 42 | 7 | 7.4 | 2 | 13 | 22.76 |
| React027_12 | 42 | 4 | 8.0 | 5 | 13 | 56.90 |
| React027_13 | 32 | 7 | 7.6 | 8 | 13 | 91.04 |
| React027_14 | 37 | 4 | 7.9 | 2 | 13 | 22.76 |
| React027_15 | 37 | 4 | 7.5 | 5 | 13 | 56.90 |
| React027_16 | 32 | 4 | 8.0 | 5 | 13 | 56.90 |

TABLE 18-continued

Actual experimental design plan.

| Run | Temperature [° C.] | Time (h) | pH [-] | Cysteine concentration [mM] | Protein content by ALC [mg/mL] | Approx. molar ratio of cysteine to protein (M/M) |
|---|---|---|---|---|---|---|
| React027_17 | 42 | 1 | 8.5 | 2 | 13 | 22.76 |
| React027_18 | 32 | 7 | 7.4 | 2 | 13 | 22.76 |
| React027_19 | 37 | 1 | 8.0 | 5 | 13 | 56.90 |
| React027_20 | 42 | 7 | 7.6 | 8 | 13 | 91.04 |
| React027_21 | 42 | 1 | 7.6 | 8 | 13 | 91.04 |
| React027_22[1] | 37 | 4 | 8.0 | 5 | 13 | 56.90 |
| React027_23 | 42 | 7 | 8.5 | 2 | 13 | 22.76 |
| React027_24 | 32 | 7 | 8.5 | 2 | 13 | 22.76 |
| React027_25 | 37 | 4 | 8.5 | 5 | 13 | 56.90 |
| React027_26 | 32 | 7 | 8.5 | 8 | 13 | 91.04 |
| React027_27 | 42 | 1 | 7.5 | 2 | 13 | 22.76 |

[1]Center points.
[2]Is not considered a center point of the used software. The relative molecular mass of secukinumab, based on amino acid sequence, is 147,944 Da, which is used to calculate the molar ratio of cysteine to protein.

The values for the product quality output parameters are listed in Table 19 in ascending order with respect to the CEX activity results. The model diagnostics for the product quality output parameter are $R^2=0.93$, $Q^2=0.80$, Model Validity=0.79 and SD=0.42 for activity by CEX; $R^2=0.96$, $Q^2=0.89$, Model Validity=0.67 and SD=0.00 for purity by CE-SDS.

TABLE 19

Input and output parameter values listed according to ascending activity by CEX.

| Run | Temperature [° C.] | Time (h) | pH [-] | Cysteine concentration [mM] | Protein Content by ALC (mg/mL) | Approx. molar ratio of cysteine to protein (M/M) | activity by CEX [%] | purity by CE-SDS [%] |
|---|---|---|---|---|---|---|---|---|
| React027_8 | 32 | 1 | 7.3 | 2 | 13 | 22.76 | 89.1 | 91 |
| React027_27 | 42 | 1 | 7.5 | 2 | 13 | 22.76 | 90.1 | 91 |
| React027_3 | 32 | 1 | 7.5 | 8 | 13 | 91.04 | 90.3 | 61 |
| React027_4 | 32 | 1 | 8.4 | 2 | 13 | 22.76 | 91.1 | 92 |
| React027_7 | 32 | 1 | 8.5 | 8 | 13 | 91.04 | 91.7 | 65 |
| React027_17 | 42 | 1 | 8.5 | 2 | 13 | 22.76 | 91.8 | 89 |
| React027_18 | 32 | 7 | 7.4 | 2 | 13 | 22.76 | 92.5 | 93 |
| React027_14 | 37 | 4 | 7.9 | 2 | 13 | 22.76 | 93.3 | 94 |
| React027_21 | 42 | 1 | 7.6 | 8 | 13 | 91.04 | 93.3 | 77 |
| React027_19 | 37 | 1 | 8.0 | 5 | 13 | 56.90 | 93.4 | 79 |
| React027_23 | 42 | 7 | 8.5 | 2 | 13 | 22.76 | 93.6 | 93 |
| React027_24 | 32 | 7 | 8.5 | 2 | 13 | 22.76 | 94.1 | 93 |
| React027_11 | 42 | 7 | 7.4 | 2 | 13 | 22.76 | 94.2 | 95 |
| React027_6 | 42 | 1 | 8.5 | 8 | 13 | 91.04 | 94.3 | 74 |
| React027_16 | 32 | 4 | 8.0 | 5 | 13 | 56.90 | 94.4 | 86 |
| React027_13 | 32 | 7 | 7.6 | 8 | 13 | 91.04 | 94.5 | 82 |
| React027_9[1] | 37 | 4 | 8.0. | 5 | 13 | 56.90 | 95.0 | 89 |
| React027_5[1,2] | 37 | 4 | 7.9 | 5 | 13 | 56.90 | 95.2 | 89 |
| React027_10 | 37 | 7 | 8.0 | 5 | 13 | 56.90 | 95.3 | 90 |
| React027_22[1] | 37 | 4 | 8.0 | 5 | 13 | 56.90 | 95.6 | 88 |
| React027_25 | 37 | 4 | 8.5 | 5 | 13 | 56.90 | 95.7 | 87 |
| React027_20 | 42 | 7 | 7.6 | 8 | 13 | 91.04 | 95.8 | 85 |
| React027_12 | 42 | 4 | 8.0 | 5 | 13 | 56.90 | 95.9 | 90 |
| React027_1 | 42 | 7 | 8.5 | 8 | 13 | 91.04 | 96.0 | 85 |
| React027_15 | 37 | 4 | 7.5 | 5 | 13 | 56.90 | 96.1 | 88 |
| React027_2 | 37 | 4 | 8.0 | 8 | 13 | 91.04 | 97.1 | 82 |
| React027_26 | 32 | 7 | 8.5 | 8 | 13 | 91.04 | 97.1 | 82 |

[1]Center point.
[2]Is not considered a center point of the used software.

Figure 6:
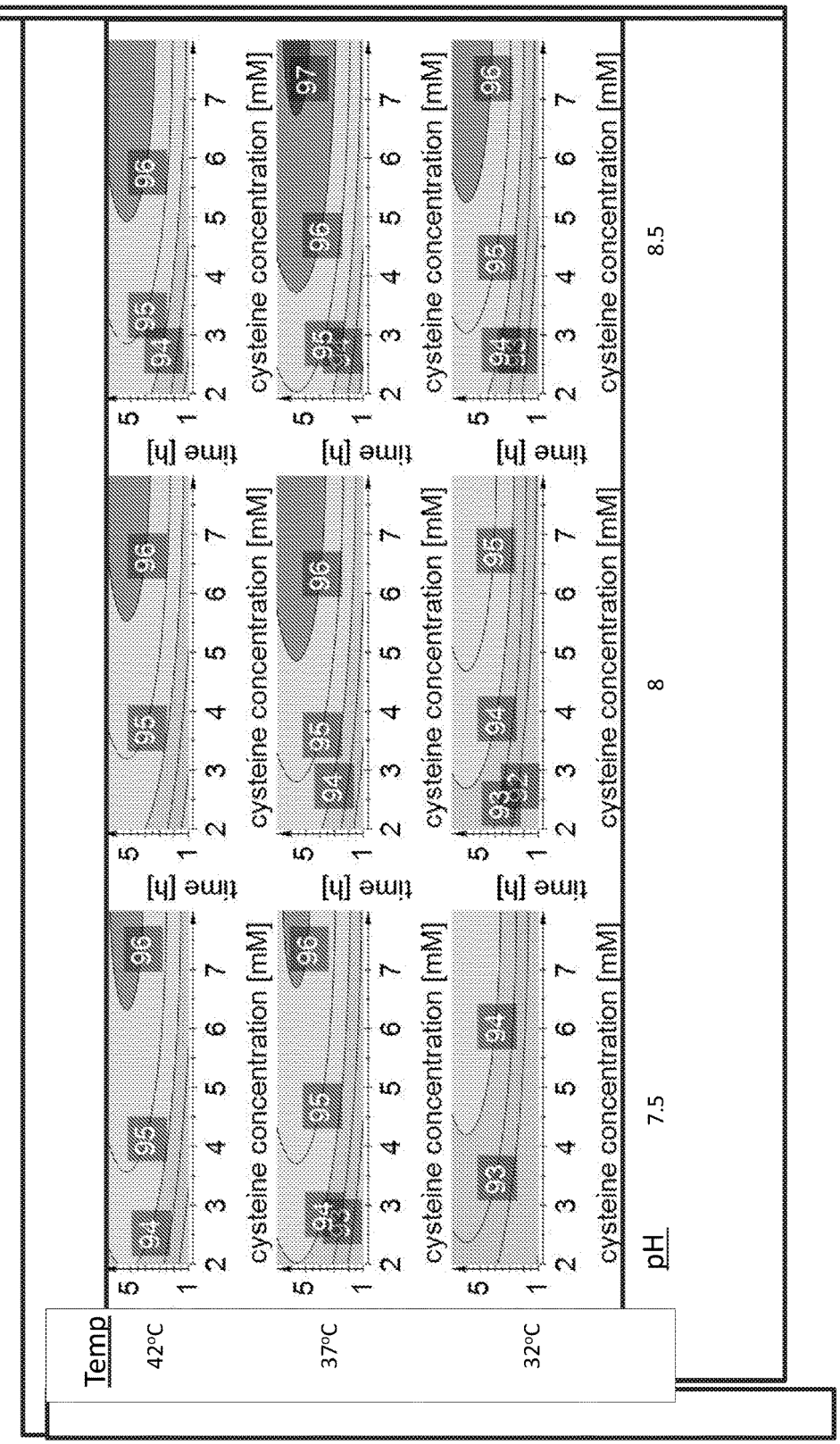
FIG. 6 shows a 4D contour plot for activity by CEX, looking at the impact and interaction of pH, time, temperature and cysteine concentration.

Table 19 shows that the runs can be divided mainly in three groups: lower activity (<93%), medium activity (93-95%), and high activity (>95%). Due to a good model fit, it is possible to use the contour plot (FIG. 6) to identify the main influencing parameters of the system. FIG. 6 shows that medium to high incubation (e.g., 4 to 7 hours) time and high cysteine concentration is beneficial to increase activity by CEX. Incubation temperature and process pH have less influence on the output parameter activity by CEX. Nevertheless, the areas for purity of 95% and above are the greatest in the plots for pH 8.0 and 8.5 at 37° C., suggesting that this is an optimal operating range.

In Table 20, the runs are listed by increasing purity by CE-SDS. The runs can be divided in three groups: runs with low purity (<82%), runs with medium purity and runs with high purity (>90%). All runs with high purity by CD-SDS employed 2 mM cysteine.

lations was run. For this simulation, a target of >93% for CEX activity and >90% for CE-SDS purity was set. The Monte Carlo simulations predicted that these quality targets are fulfilled when temperature is ideally at 39.1° C., but temperature can vary between 38.6° C. to 39.7° C. The incubation time has an ideal at 5.0 h, but can vary between 4.0 h and 6.0 h. For the pH, the ideal is 8.2 and it can vary from 8.15 to 8.25. For the last input parameter, cysteine concentration, the ideal predicted is 2.4 mM and can vary between 2.2 mM to 2.5 mM. Within these ranges, the design space estimator has found that for the product quality output parameter activity by CEX the estimated DPMO (Defect Per Million Operations) value will be 110 and the DPMO value for Purity by CE-SDS will be 20. This means that 110 times out of one million the target limit for activity by CEX will not be met and 20 times out of a million the target limit for the purity by CE-SDS.

TABLE 20

Input and output parameters listed with increasing purity by CE-SDS.

| Run | Temperature [° C.] | Time (h) | pH [-] | Cysteine concentration [mM] | Protein Content by ALC (mg/mL) | Approx. molar ratio of cysteine to protein (M/M) | activity by CEX [%] | purity by CE-SDS [%] |
|---|---|---|---|---|---|---|---|---|
| React027_3 | 32 | 1 | 7.5 | 8 | 13 | 91.04 | 90.3 | 61 |
| React027_7 | 32 | 1 | 8.5 | 8 | 13 | 91.04 | 91.7 | 65 |
| React027_6 | 42 | 1 | 8.5 | 8 | 13 | 91.04 | 94.3 | 74 |
| React027_21 | 42 | 1 | 7.6 | 8 | 13 | 91.04 | 93.3 | 77 |
| React027_19 | 37 | 1 | 8.0 | 5 | 13 | 56.90 | 93.4 | 79 |
| React027_13 | 32 | 7 | 7.6 | 8 | 13 | 91.04 | 94.5 | 82 |
| React027_2 | 37 | 4 | 8.0 | 8 | 13 | 91.04 | 97.1 | 82 |
| React027_26 | 32 | 7 | 8.5 | 8 | 13 | 91.04 | 97.1 | 82 |
| React027_20 | 42 | 7 | 7.6 | 8 | 13 | 91.04 | 95.8 | 85 |
| React027_1 | 42 | 7 | 8.5 | 8 | 13 | 91.04 | 96.0 | 85 |
| React027_16 | 32 | 4 | 8.0 | 5 | 13 | 56.90 | 94.4 | 86 |
| React027_25 | 37 | 4 | 8.5 | 5 | 13 | 56.90 | 95.7 | 87 |
| React027_22[1] | 37 | 4 | 8.0 | 5 | 13 | 56.90 | 95.6 | 88 |
| React027_15 | 37 | 4 | 7.5 | 5 | 13 | 56.90 | 96.1 | 88 |
| React027_17 | 42 | 1 | 8.5 | 2 | 13 | 22.76 | 91.8 | 89 |
| React027_9[1] | 37 | 4 | 8.0 | 5 | 13 | 56.90 | 95.0 | 89 |
| React027_5[1,2] | 37 | 4 | 7.9 | 5 | 13 | 56.90 | 95.2 | 89 |
| React027_10 | 37 | 7 | 8.0 | 5 | 13 | 56.90 | 95.3 | 90 |
| React027_12 | 42 | 4 | 8.0 | 5 | 13 | 56.90 | 95.9 | 90 |
| React027_8 | 32 | 1 | 7.3 | 2 | 13 | 22.76 | 89.1 | 91 |
| React027_27 | 42 | 1 | 7.5 | 2 | 13 | 22.76 | 90.1 | 91 |
| React027_4 | 32 | 1 | 8.4 | 2 | 13 | 22.76 | 91.1 | 92 |
| React027_18 | 32 | 7 | 7.4 | 2 | 13 | 22.76 | 92.5 | 93 |
| React027_23 | 42 | 7 | 8.5 | 2 | 13 | 22.76 | 93.6 | 93 |
| React027_24 | 32 | 7 | 8.5 | 2 | 13 | 22.76 | 94.1 | 93 |
| React027_14 | 37 | 4 | 7.9 | 2 | 13 | 22.76 | 93.3 | 94 |
| React027_11 | 42 | 7 | 7.4 | 2 | 13 | 22.76 | 94.2 | 95 |

[1]Center point.
[2]Is not considered a center point of the used software.

Figure 7:
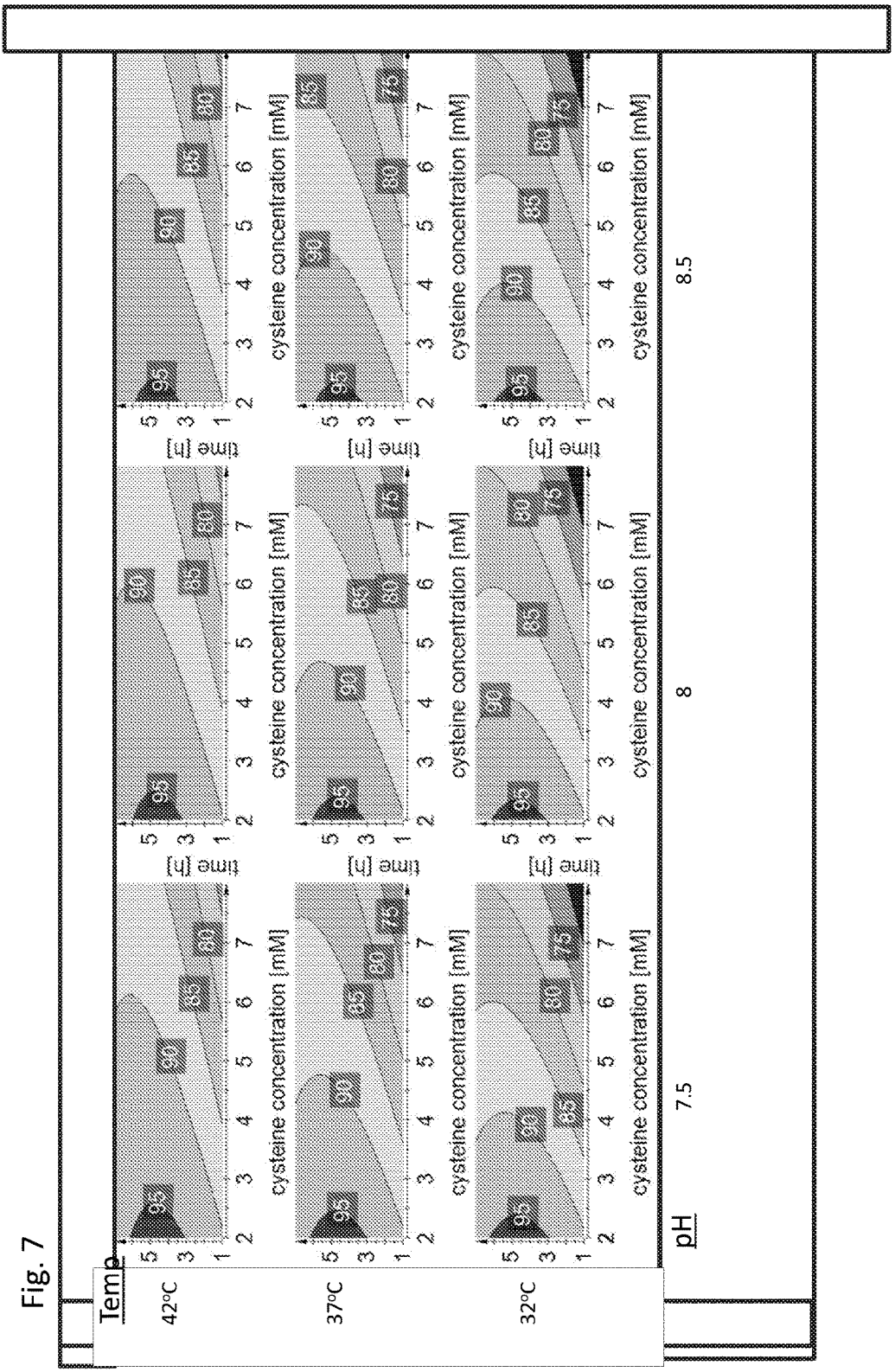
FIG. 7 shows a 4D contour plot for purity by CE-SDS, looking at the impact and interaction of pH, time, temperature and cysteine concentration.

Because of the good model fit, a contour plot (FIG. 7) can be used to understand the process and the main influencing input parameters. FIG. 7 shows that medium to high incubation time and low cysteine concentration increase purity by CE-SDS. The input parameters incubation temperature and process pH have a minor influence on purity by CE-SDS.

Summary and Conclusions Drawn from Example 6

The development targets are fulfilled when the cysteine concentration is held at a low level, while the temperature can vary from center to high, the pH can vary from center to high, and the time can vary from center to high. To help estimate the input parameter ranges that lead to high product quality, a design space estimator using Monte Carlo simu- According to the results of the contour plots, and taking into account the results of the previous development studies (DoE1 and DoE2), the target for incubation temperature was set to 37° C. The incubation time target was set to 4 hours (240 minutes), as with the present experimental setup no heating and cooling time was included, which will be considered for manufacturing scale applications. Combined with heating and cooling time, an overall process time of approximately 6 hours will be applied. The influence of pH on purity by CE-SDS is not detectable and on activity by CEX the influence is minor. Therefore, the target was set to 8.0, as it is well within the tested range, the development target for activity by CEX can be safely met, and the risk of formation of acidic variants by CEX (enhanced by basic conditions) will be decreased. The results for the input parameter cysteine concentration indicates a low optimum level of 2.4 mM; however, most experiments employing 2 mM cysteine resulted in lower activity by CEX than was desired. This, combined with the results of the target runs, suggests that the target for cysteine concentration should be higher, i.e., 4 mM, during confirmation runs.

Example 7: Process Comparisons and Analysis of Continuous Stirring

Example 7.1—Comparison of Process B2 and Process C

The considerations described in Example 6 suggested that the selective reduction could preferably be done at higher protein concentration and lower cysteine concentration (4-6 mM) than so far carried out at manufacturing scale (Process B2 herein). Table 21 compares the input parameters for earlier Process B2 and Proposed process C. Comparison runs were performed in duplicate at 50 mL scale in polypropylene tubes, which were placed in a water bath and warmed to 37° C. The results are shown in Table 22.

TABLE 21

Input parameters of process B2 and proposed process C. 1) Before pH adjustment and cysteine addition. The relative molecular mass of secukinumab, based on amino acid sequence, is 147,944 Da, which is used to calculate the molar ratio of cysteine to protein.

|  | Unit | Process B2 | Proposed process C |
|---|---|---|---|
| Cysteine concentration | [mM] | 8.00 | 4.00 |
| Protein concentration[1)] | [mg/mL] | 4.30 | 13.50 |
| Approx. molar ratio cysteine to protein | [M/M] | 275.24 | 43.84 |
| pH | [-] | 8.00 | 8.00 |
| Incubation time | [h] | 4.00 | 4.00 |
| temperature | [° C.] | 37.00 | 37.00 |

TABLE 22

Output parameters of process B2 and proposed process C.

| Run | Step performance | Unit | Activity by CEX | Purity by CE-SDS |
|---|---|---|---|---|
| REACT030 | Proposed process C | [%] | 95.5 | 95 |
| REACT031 | Proposed process C | [%] | 95.0 | 95 |
| REACT032 | Process B2 | [%] | 96.7 | 79 |
| REACT033 | Process B2 | [%] | 97.0 | 79 |

Table 22 shows that the modified cysteine treatment step of Process C leads to a significant increase in CE-SDS purity with only a very slight decrease in activity by CEX. The higher values of purity by CE-SDS are achieved by increased protein concentration and decreased cysteine concentration during the selective reductive step (i.e., a smaller molar ratio of cysteine to protein). This leads to a lower reductive power that is nevertheless still sufficient to ensure adequate activity of secukinumab.

Example 7.2—Testing of Continuous Stirring During Incubation

During clinical manufacturing according to process B2, an intermittent mixing was applied (2 minutes every hour) to avoid inhomogeneities during the incubation phase at 37° C. The feasibility of using continuous stirring to assure homogeneity throughout incubation was tested in a 2L bioreactor (run REACT029). The experimental setup and process conditions are shown in Table 23.

TABLE 23

Input parameters for testing continuous stirring during reaction. 1) Before pH adjustment and cysteine addition. The relative molecular mass of secukinumab, based on amino acid sequence, is 147,944 Da, which is used to calculate the molar ratio of cysteine to protein.

|  | Unit | REACT029 |
|---|---|---|
| Cysteine concentration | [mM] | 4.00 |
| Protein concentration[1)] | [mg/mL] | 13.50 |
| Approx. molar ratio cysteine to protein | [M/M] | 43.84 |
| Stirrer speed during incubation | [rpm] | 200.00 |
| Filling volume | [L] | 1.20 |
| Incubation time | [h] | 4.00 |

For REACT029, purity by CE-SDS was 96% and activity by CEX was 92.7%, which is a lower CEX activity than shown by runs REACT030 and REACT 031 (proposed Process C) performed at small scale without stirring. Thus, increased oxygen transfer into the cysteine treatment solution caused by continuous mixing could abrogate the reductive power of the cysteine. Nevertheless, the activity by CEX in the cysteine treatment pool was close to the quality target. Since oxygen transfer and the ratio surface/volume decreases with scale-up to manufacturing scale, this experiment was considered the worst case regarding high oxygen transfer. Continuous mixing was therefore used for the pilot scale runs ("Process C"), in order to ensure the homogeneity of the process solution.

Summary and Conclusions Drawn from Examples 5-7

We determined that the protein concentration during cysteine treatment can be increased threefold, which decreases process volumes significantly. We also demonstrated that lower cysteine concentrations provide similar product activity and increased product purity by CE-SDS after cysteine treatment. Thus, lower ratios of cysteine:protein are able to ensure quality product.

The data also shows that temperature and pH have minor influence on the cysteine treatment step and that addition of the oxidized form of cysteine—cystine—is not necessary to obtain quality product. Although the incubation time showed an ideal at 5 hours, we set the target to 4 hours, as with the present experimental setup no heating and cooling time was included, which must be accounted for during manufacturing-scale applications. Continuous stirring under open conditions without active aeration appeared to be feasible for use in the selective reduction method; however, as we will show in later Examples, the oxygen transfer into the solution should be limited (e.g., using low/slow stirring).

Example 8: Process Confirmation at Pilot Scale

The proposed purification conditions after process improvement were tested by process confirmation at 7 L pilot-scale in order to perform a first scale-up and obtain a first impression on the reproducibility and robustness of the process. The selective reduction step according to Process C (Table 21) was used in the pilot scale experiments (RE- ACT035). Continuous stirring was applied. The dissolved oxygen concentration was measured by a $pO_2$ probe.

Figure 8:
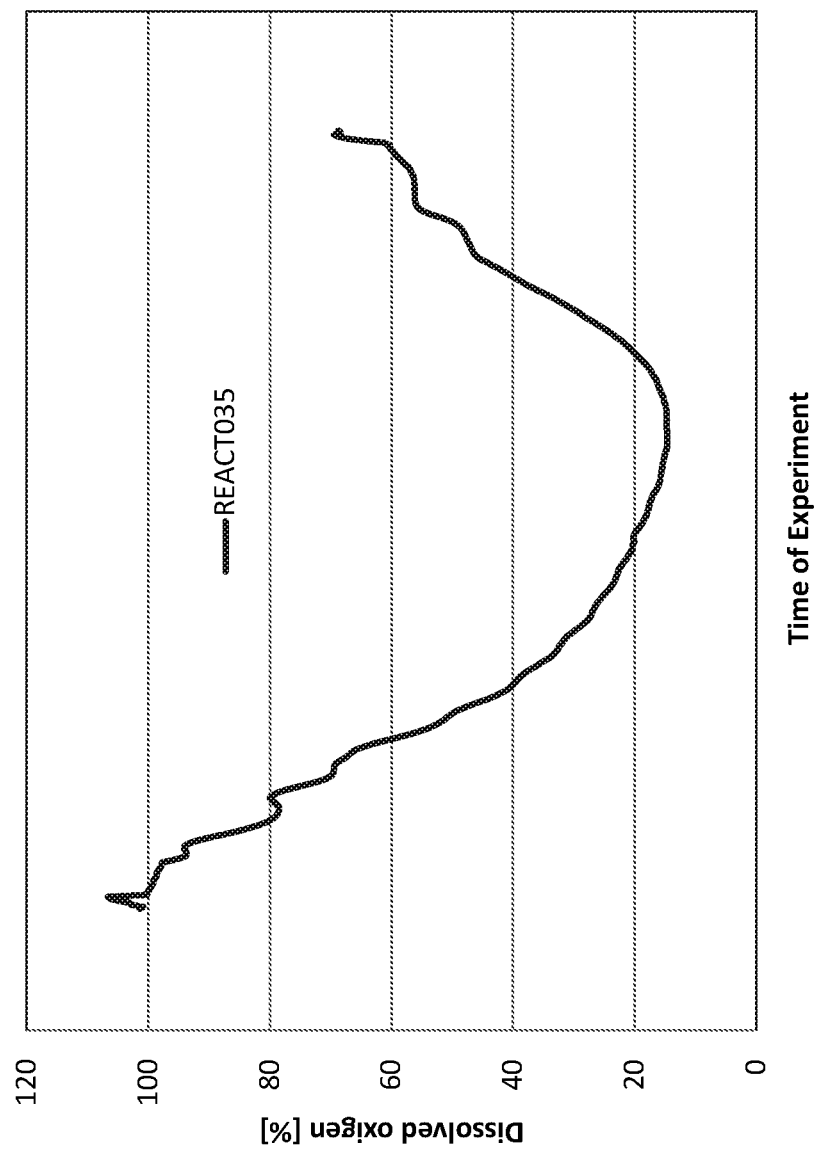
FIG. 8 shows the dissolved oxygen chart of the cysteine treatment of the confirmation run 1.

The activity by CEX of REACT035 following the selective reduction step according to confirmation run 1 was only 90.4%. Analysis of the dissolved oxygen curve (see FIG. 8) revealed that there is a steady decrease of $pO_2$ in the first three hours of the treatment, indicating that oxygene consumption takes place in the solution faster than oxygen transfer into the solution triggered by stirring. We assume that oxygene consumption is caused by oxidation of the cysteine reagent (Cys-SH) to cystine or either cysteic acid (Cys-$SO_3$). The increase of the oxygene level in the last hour of the reaction would then indicate that the cysteine reagent had been consumed and oxygen take up by the solution caused by stirring becomes visible. This implies that the reductive power of cysteine is not effective in the last period of the treatment, which could explain the impaired activity obtained from this run.

Example 8.1—Investigation of the Cysteine Step During Confirmation Run 1

To investigate the root cause for the low activity (90.4%) determined by CEX in the first pilot scale run REACT035, the possible influencing factors were assessed. As mentioned above, a low cysteine concentration, introduction of oxygen by extended stirring during the reaction, and the scale change (increased reaction volume) could result in insufficient reductive power. Hence, the stirrer speed during incubation and cysteine concentration were evaluated.

The experimental plan and output parameter activity by CEX is shown in Table 24. In this experiment, the dissolved oxygen concentration was measured by a $pO_2$ probe.

TABLE 24

Investigation of stirring and cysteine concentration on the cysteine treatment step. 1) confirmation run 1, performed in a 20 L bioreactor with 7 L filling volume. 2) experiment performed in a 2 L bioreactor with 1.7 L filling volume. 3) mixing every hour for 2 minutes with 50 rpm. The relative molecular mass of secukinumab, based on amino acid sequence, is 147,944 Da, which is used to calculate the molar ratio of cysteine to protein.

| Run | Cysteine concentration [mM] | Approx. molar ratio cysteine to protein [M/M] | Stirring during incubation [rpm] | Activity by CEX [%] |
|---|---|---|---|---|
| REACT035 [1] | 4 | 43.84 | 100 | 90.4 |
| REACT038 [2] | 4 | 43.84 | 0 [3] | 92.5 |
| REACT039 [2] | 4 | 43.84 | 50 | 93.7 |
| REACT040 [2] | 6 | 65.75 | 50 | 91.9 |

All three smaller scale reactions (REACT038, REACT039, and REACT040) showed improved activity by CEX in comparison to confirmation run 1 (REACT035) (Table 24). However, the corresponding activity by CEX was not increased in the experiment with elevated cysteine concentration (REACT040) or in the experiment without continuous mixing during incubation time (REACT038) when compared to REACT039. Hence, neither the cysteine concentration nor the stirring during incubation could be identified at this point as the main influencing factor. Nevertheless, the dissolved oxygen ($dO_2$) profile of the pilot scale confirmation run 1 (REACT035) (FIG. 8) showed an increase in $dO_2$ after approximately 3 hours incubation, indicating that the reductive power of cysteine has been exhausted. The $dO_2$ chart of the two smaller scale experiments REACT039 and REACT040, in which continuous stirring was performed, show no increase in $dO_2$ towards the end of the treatment (data not shown), indicating that the reductive power of the cysteine had not been exhausted in these smaller scale experiments.

Example 8.2—Investigation of the Cysteine Step During Confirmation Run 2

The filling volume was 14 L instead of 7 L as in confirmation run 1 and two stirrers were used for stirring (radial stirrer at the bottom and in addition axial on the top). Cysteine concentration (4 mM) and stirrer speed (100 rpm) were the same as in confirmation run 1, REACT 035. Following selective reduction, the activity of the antibody solution was only 85.5% measured by CEX. According to the $dO_2$ chart shown in FIG. 9, the reductive power of the cysteine was exhausted even earlier than during confirmation run 1 (FIG. 8), suggesting that the oxygen transfer into the solution by continuous stirring was more pronounced in this run.

Figure 9:
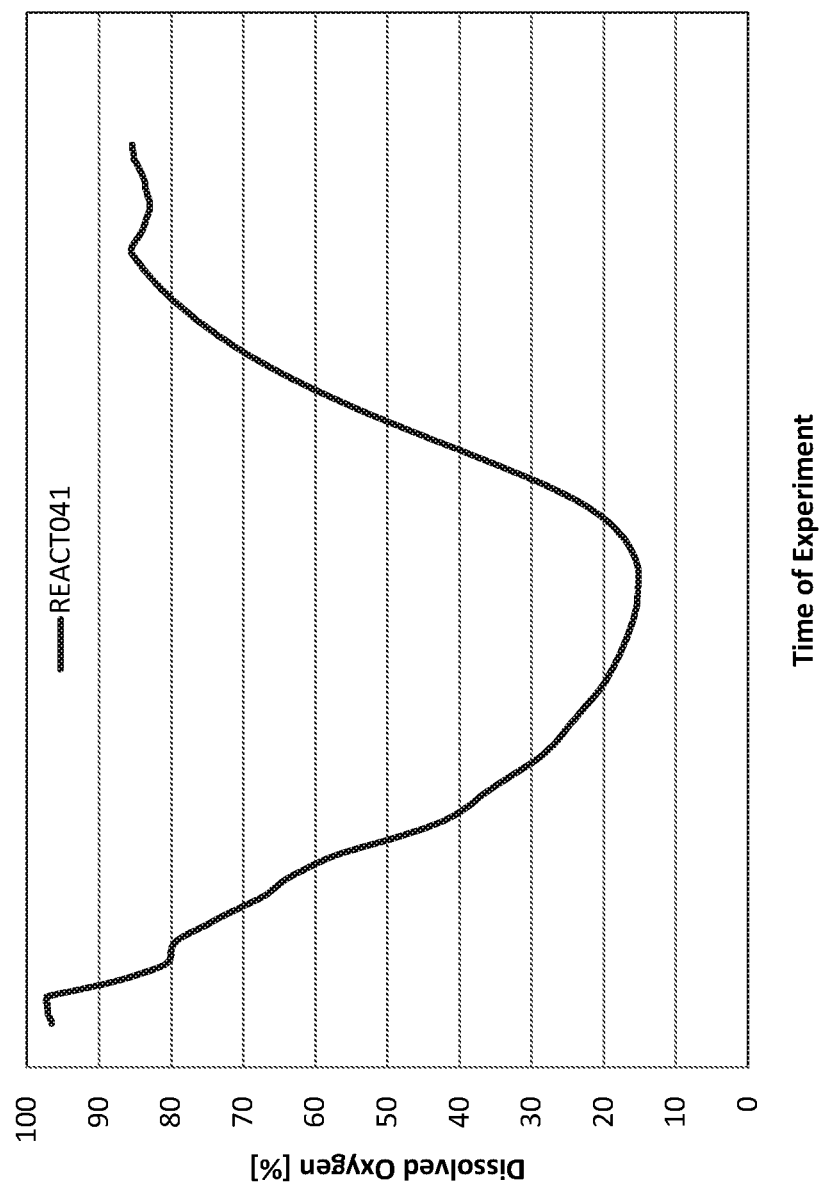
FIG. 9 shows the dissolved oxygen chart of the cysteine treatment of the confirmation run 2.

The $dO_2$ curve trends in (FIG. 8-9) suggest that the oxygen transfer over the headspace by continuous stirring is the main root cause for lower activity after the selective reduction step during confirmation run 1 and 2. With 7 L filling volume at confirmation run 1, only one stirrer (radial stirrer at the bottom) was submerged in the process solution of the cysteine treatment step. With 14 L filling volume at confirmation run 2, two stirrers (radial stirrer at the bottom and axial on the top) were submerged in the process solution, leading to even further increased oxygen transfer into the solution. Hence, the even poorer result of confirmation run 2 is most probably due to the elevated oxygen transfer into the process solution, visible by the $dO_2$ curve (FIG. 9). Due to the higher oxygen transfer into the solution for confirmation run 2, the reductive power of the cysteine is exhausted earlier, resulting in less activity by CEX. Therefore, the oxygen transfer into the process intermediate should be restricted, e.g., by adjustment of mixing (speed, duration, frequency) during incubation.

Example 8.3—Investigation of the Cysteine Step During Confirmation Run 3

The filling volume was 16 L instead of 14 L as in confirmation run 2 and the stirring profile was adapted. Instead of continuous stirring during the cysteine treatment, only mixing for 2 minutes every hour was applied, corresponding to earlier process B2. The activity of the antibody solution measured by CEX following the selective reduction step was 92.5%.

Figure 10:
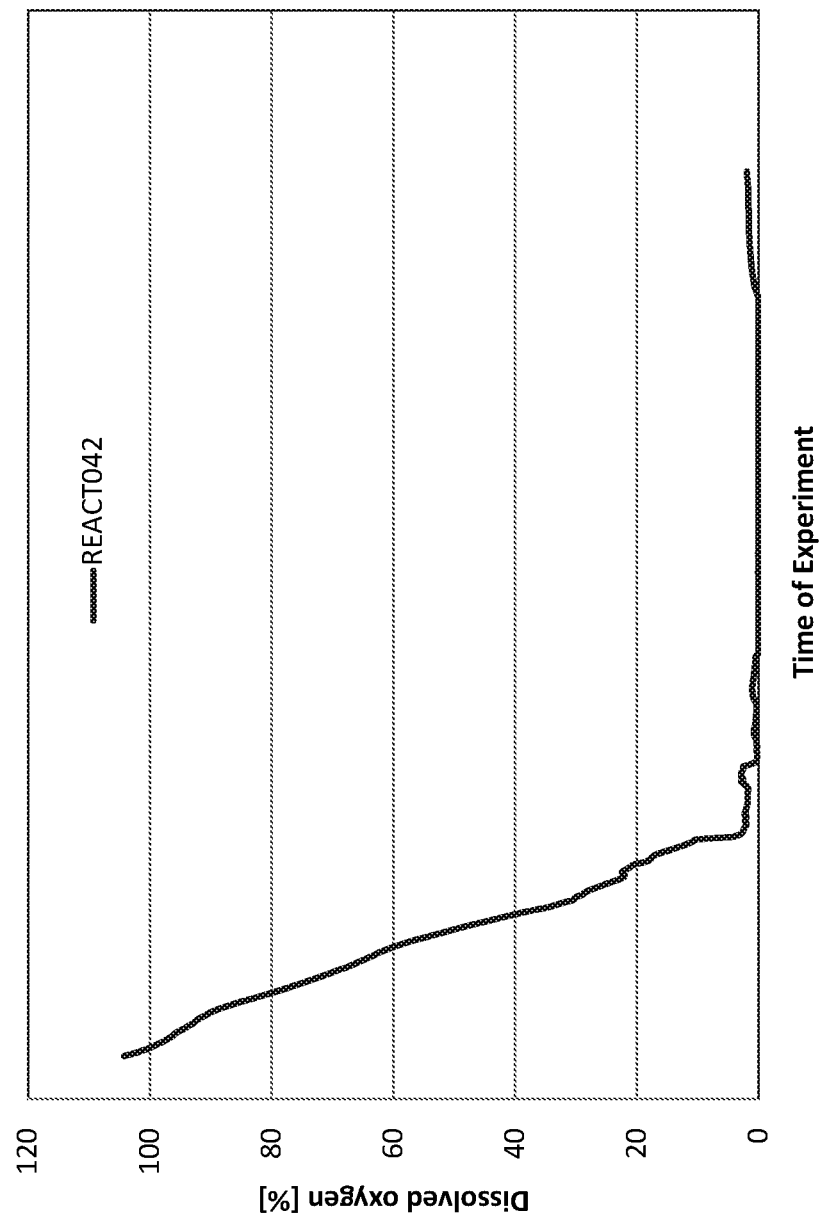
FIG. 10 shows the dissolved oxygen chart of the cysteine treatment of the confirmation run 3.

Due to omission of continuous mixing in the cysteine treatment step, oxygen transfer was restricted, ensuring sufficient reductive power and leading to high activity by CEX. The $dO_2$ chart shown in FIG. 10 shows a steep decrease of the oxygen level-almost to zero % in the beginning of the treatment. This experiment demonstrates that regulating the amount of oxygen introduced during the cysteine treatment ensures proper reaction conditions and consequently a high activity by CEX.

Example 8.4—Investigation of the Cysteine Step During Confirmation Run 4

Based on the results of confirmation run 3, the 4th pilot-scale confirmation run (REACT040) was performed with the identical setup and process conditions of confirmation run 3. However, the cysteine treatment in the pool was increased from 4 mM to 6 mM such that the process of confirmation run 4 is capable of handling higher oxygen transfer into the solution. This increased reductive power must be balanced against possible antibody over reduction. Nevertheless, based on the results of REACT040 (see Table 24), this adaptation represents a change with a low risk of failure. The activity by CEX of REACT040 following the selective reduction step was 91.9%.

Figure 11:
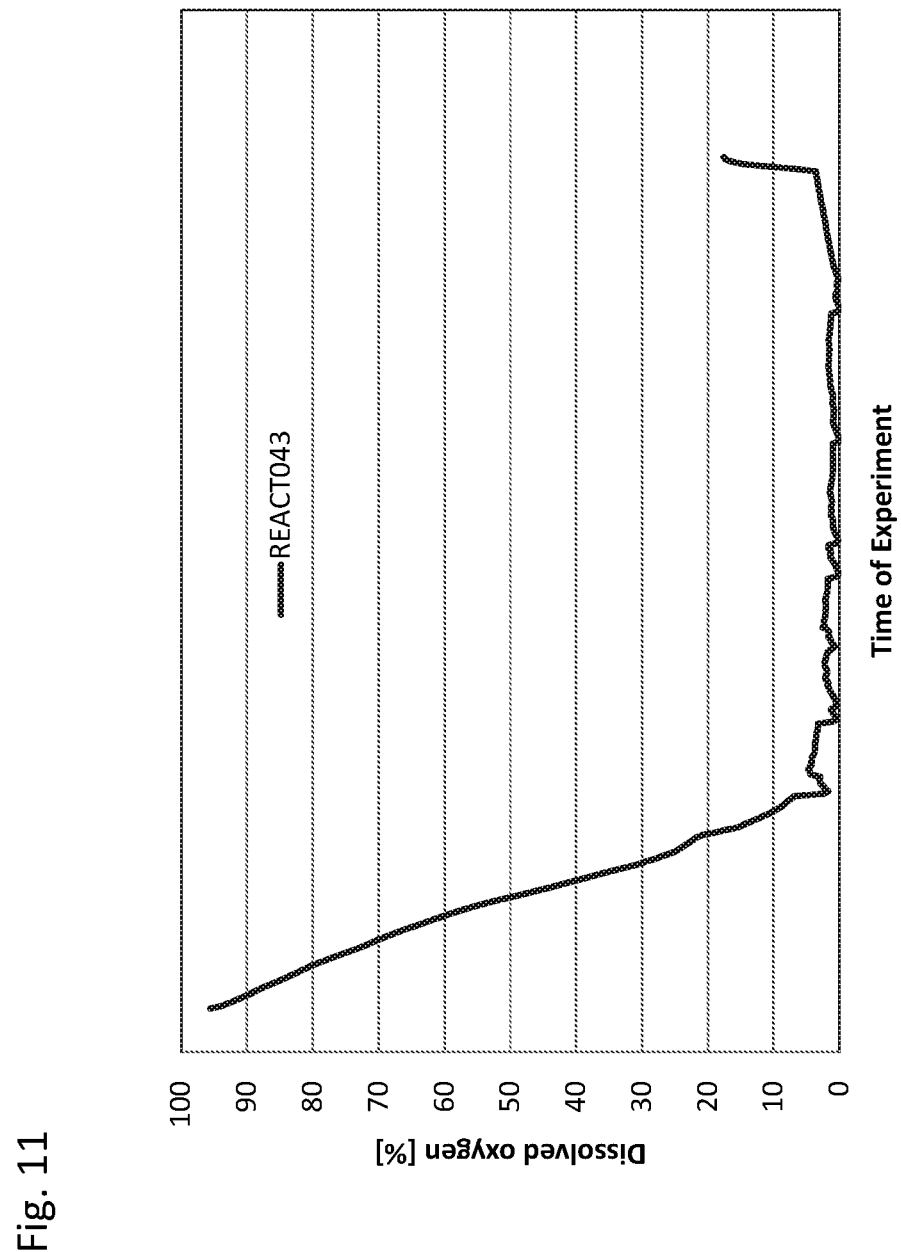
FIG. 11 shows the dissolved oxygen chart of the cysteine treatment of the confirmation run 4.
Figure 12:
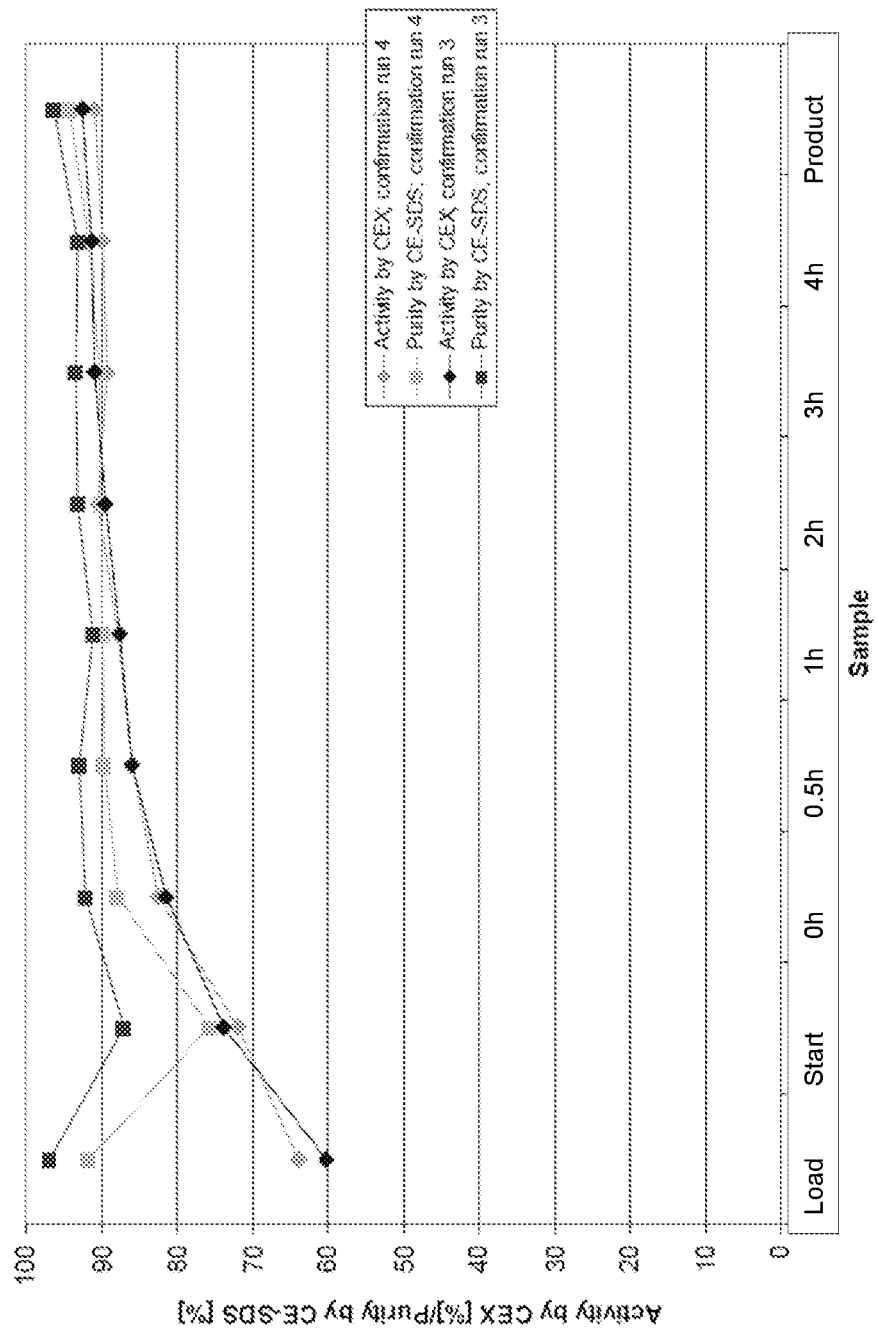
FIG. 12 compares the reaction kinetic of confirmation run 3 and confirmation run 4 with respect to activity by CEX and purity by CE-SDS.

In FIG. 11, the $dO_2$ chart of confirmation run 4 is shown. Similarly to confirmation run 3, the $dO_2$ decreased after cysteine addition and remained at low levels, indicating that the reductive power of the cysteine in this experiment is not exhausted, while the product purity requirement determined by CE-SDS is fulfilled In FIG. 12, the reaction kinetic of confirmation run 3 and confirmation run 4 are compared with respect to activity by CEX and purity by CE-SDS. The kinetic of activity by CEX is comparable for both experiments; after approximately 2 h a plateau is reached, and thereafter the increase of activity is small in the following 2 hours treatment. The purity by CE-SDS curves are slightly different in the early phase of the reaction, in that the purity drop is more pronounced in the run at the higher cysteine concentration (6 mM). However, as both procedures lead to comparable product quality at the end of the cysteine treatment, both are appropriate to ensure adequate product quality. Nevertheless, considering the effect of elevated oxygen levels in the process solution, the process with the increased cysteine concentration applied in confirmation run 4 is expected to be more robust in respect to variations of the oxygen transfer into the process solution during cysteine treatment. Conclusively, a cysteine concentration of 6 mM (with 13.5 mg antibody=65.75:1 molar ratio of cysteine:antibody [i.e., about 66:1]) was selected for the cysteine treatment step at manufacturing-scale, identical to the conditions of confirmation run 4. We also noted faster kinetics for CEX activity (plateau in 1 hour) in a run performed at a molar ratio of about 275:1 (cysteine:protein) (data not shown).

Summary and Conclusions Drawn from Example 8

We determined that elevated oxygen levels during the cysteine treatment step can have a deleterious effect on activity by CEX, which is likely due to the oxygen abrogating the reductive power of the cysteine, leading to insufficient reduction of C97 of secukinumab. Oxygen uptake from the atmosphere can be managed by varying the cysteine/protein ratio, using defined stirring speeds, or even employing stirring interruptions, when working at production scale.

Based on the results of the confirmation runs, the cysteine concentration was increased from 4 mM (molar ratio of cysteine to protein of 43.84) to 6 mM (molar ratio of cysteine to protein of 65.75), which should counterbalance the oxygen present in reaction solution. Furthermore, to reduce the level of dissolved oxygen present during the incubation phase of the selective reduction reaction, continuous mixing was replaced by mixing 2 minutes every hour during incubation. Although the selective reduction procedure was changed during process confirmation, a clear root cause was identified (level of oxygen transferred into solution during selective reduction), ensuring adequate activity by CEX in the drug substance by the adjusted cysteine treatment step.

Example 9: Characterization of the Selective Reduction Step

The influence of the input parameters protein concentration, cysteine concentration and stirrer speed on the selective reduction step were evaluated in a statistical design. The output parameters activity by CEX and purity by CE-SDS were used to assess product quality after selective reduction step and to define the proven acceptable ranges for the input parameters. Output parameters ranges were defined according to earlier design processes. These limits were used to define the input parameter ranges.

Additionally, the results of the three scale-down model qualification runs and seven selective reduction cycles performed at manufacturing-scale were used to assess product quality after selective reduction for the worst/best case studies regarding reductive power and the dedicated runs for incubation time and incubation temperature.

Example 9.1—Process Characterization: Response Surface Design

Example 9.1.1—Experimental Design and Methods

Protein content, cysteine concentration and stirring mode during incubation (no stirring, continuous stirring at 50 or 100 rpm) were selected as input parameters for the response surface design, see Table 25.

TABLE 25

Input parameters. 1) corresponds to a defined cysteine concentration during the selective reduction. "Content by ALC" refers to the concentration of the antibody.

| Name | Unit | Lower level | Medium level | Upper level |
| --- | --- | --- | --- | --- |
| Protein content by ALC | [mg/mL] | 10 | 12.7 | 15.4 |
| Dilution factor by TITR3 addition[1] | [-] | 15 (4.8 mM cysteine, 0.8 mM EDTA) | 20 (6.0 M cysteine) | 25 (8 mM cysteine; 1.3 mM EDTA) |
| Stirrer speed during incubation | [rpm] | 0 | 50 | 100 |

Various cysteine concentrations, expressed as "dilution factor by TITR3 addition," were employed that reflect process conditions and potential variations, e.g., induced by weighing inaccuracy, inaccuracy of solution addition, etc. The antibody concentration contributes to the ratio of cysteine to protein and was also tested within the present design in order to detect potential interactions. Additionally, the stirrer speed during incubation was tested as an input parameter because, as shown in Examples 8, oxygen transferred from the headspace into the solution influences the selective reduction step.

A Central Composite Face Design with 3 center point runs was used. This type of design supports calculation of mathematical models with linear terms, interaction terms and quadratic terms. Secukinumab, INAKT.F (stored below −60° C.) originating from manufacturing-scale run B012307 was used. Buffers used for process characterization were Titration Buffer AIN457-TITR1 (1M Tris base, pH 10.8 [pH range ≥10.0, conductivity 0.10-0.30 mS/cm]), Titration buffer AIN457-TITR2 (0.3 M o-phosphoric acid, pH 1.4 [pH range ≤2.0; conductivity range 19.5-22.7 mS/cm]); Titration buffer AIN457-TITR3 (120 mM cysteine-HCL+20 mM Di-Na-EDTA, pH 8.0 [pH range 7.8-8.2; conductivity range 14.7-18.3 mS/cm]).

The experiments were performed on the qualified scale-down model (described in detail in Example 10) in a stirred bioreactor (maximum 2 L volume) at ambient atmosphere with free air exchange and monitoring of pH, dissolved oxygen, stirrer speed and temperature. The experimental design plan is shown in Table 26. All input parameters that were not part of the individual studies were held constant at the respective target according to Table 27.

TABLE 26

Experimental design plan. 1) Center Point.

| Run | Protein content by ALC [mg/mL] | Dilution factor by TITR3 addition [-] | Stirrer speed during incubation [rpm] | Cysteine [mM] | Approx. molar ratio cysteine to protein [M/M] |
|---|---|---|---|---|---|
| REACT069[1] | 12.7 | 20 | 50 | 6.0 | 69.89 |
| REACT070 | 12.7 | 20 | 0 | 6.0 | 69.89 |
| REACT072 | 12.7 | 25 | 50 | 4.8 | 55.92 |
| REACT073[1] | 12.7 | 20 | 50 | 6.0 | 69.89 |
| REACT075 | 12.7 | 20 | 100 | 6.0 | 69.89 |
| REACT077 | 15.4 | 15 | 0 | 8.0 | 76.85 |
| REACT079 | 15.4 | 20 | 50 | 6.0 | 57.64 |
| REACT080 | 10.0 | 15 | 0 | 8.0 | 118.36 |
| REACT082 | 15.4 | 25 | 0 | 8.0 | 76.85 |
| REACT084 | 10.0 | 25 | 100 | 4.8 | 71.01 |
| REACT085 | 15.4 | 25 | 100 | 4.8 | 46.11 |
| REACT086 | 10.0 | 20 | 50 | 6.0 | 88.77 |
| REACT087 | 12.7 | 15 | 50 | 8.0 | 93.19 |
| REACT088[1] | 12.7 | 20 | 50 | 6.0 | 69.89 |
| REACT089 | 15.4 | 15 | 100 | 8.0 | 76.85 |
| REACT090 | 10.0 | 25 | 0 | 4.8 | 71.01 |
| REACT091 | 10.0 | 15 | 100 | 8.0 | 118.36 |

TABLE 27

Process parameters of the selective reduction step. 1) stirring for every hour for 2 minutes at a speed of 50 rpm.

| Process parameter | Unit | Target |
|---|---|---|
| Load pH | — | 8 |
| Load temperature | ° C. | as is |
| Protein concentration before pH adjustment and TITR3 addition | mg/mL | 13.5 |
| Incubation temperature | ° C. | 37 |
| Temperature after cooling | ° C. | 22 |
| Stirrer speed during heating and cooling | rpm | 50 |
| Stirrer speed during incubation [1)] | rpm | 0 |
| Heating time | min | 60 |
| Incubation time | min | 240 REACTPT.300 and 300 for REACTP |
| Cooling time | min | 60 |
| pH of REACT.P | — | 5.2 |
| Dissolved oxygen | % | as is |
| Dilution factor with TITR3 | — | 1:20 (6 mM) |

INAKT.F was thawed in a hand warm water bath and diluted with WFI to target concentration. After pH adjustment, 1 L of the solution was transferred into the qualified 2 L bioreactor equipped with a $dO_2$ probe and stirrer. The selective reduction was started by adding the calculated volume of cysteine stock solution (TITR3 buffer) to achieve the cysteine target concentration listed in Table 28. The solution was heated to incubation temperature of 37° C. within 60 minutes under stirring of 50 rpm. The solution was then incubated at 37° C. for 300 min either with continuous stirring at 50 or 100 rpm or with no stirring (0 rpm) according to the experimental design plan. After 300 minutes reaction time (60 minutes heating and 240 minutes incubation) a sample was withdrawn (REACT.PT300). After an additional 60 minutes incubation at 37° C. (60 minutes heating and 300 minutes incubation), the solution was cooled to ambient temperature within 60 minutes at a stirrer speed of 50 rpm and another sample was withdrawn (REACT.P, total reaction time 420 min). This procedure makes it possible to evaluate the design at two time points (referred to as "REACT.PT300" and "REACT.P") and to evaluate potential impact of incubation time.

Example 9.1.2—Output Parameters of Response Surface Design

The values for the product quality output parameters for samples REACT.PT300 and REACT.P are listed in Table 28 (ordered by ascending CEX activity in REACT PT300 samples) and Table 29 (ordered by ascending CEX activity in REACT P samples). In general, the data shows that purity by CE-SDS was high (>90%) in all runs, however some runs had a lower activity by CEX (<90%). With respect to CEX activity in REACT.PT300 samples (Table 28), there was one run with low activity (89.4%). In this run (REACT085) cysteine concentration was at the low limit, antibody concentration high (hence molar ratio cysteine to protein was the lowest), and stirring speed was the highest (highest oxygen transfer rate). Also, it can be seen that there is a group of eight runs with high activity (more than 96%) which contain all runs where no stirring took place.

TABLE 28

Input parameters and quality output parameter values REACT.PT300 and REACT.P sorted by ascending CEX for REACT.PT300 samples.

| Run | Antibody content by ALC [mg/mL] | Stirrer speed during incubation [rpm] | Cysteine conc. [mM] | Approx. molar ratio cysteine to protein [M/M] | React. PT300 activity by CEX [%] | React.P activity by CEX [%] | React. PT300 purity by CE-SDS [%] | React.P purity by CE-SDS [%] |
|---|---|---|---|---|---|---|---|---|
| REACT085 | 15.4 | 100 | 4.8 | 46.11 | 89.4 | 84.0 | 95 | 94 |
| REACT091 | 10.0 | 100 | 8.0 | 118.36 | 92.4 | 91.3 | 93 | 94 |
| REACT084 | 10.0 | 100 | 4.8 | 71.01 | 94.3 | 88.9 | 95 | 95 |
| REACT072 | 12.7 | 50 | 4.8 | 55.92 | 94.5 | 90.2 | 96 | 95 |

TABLE 28-continued

Input parameters and quality output parameter values REACT.PT300 and REACT.P sorted by ascending CEX for REACT.PT300 samples.

| Run | Antibody content by ALC [mg/mL] | Stirrer speed during incubation [rpm] | Cysteine conc. [mM] | Approx. molar ratio cysteine to protein [M/M] | React. PT300 activity by CEX [%] | React.P activity by CEX [%] | React. PT300 purity by CE-SDS [%] | React.P purity by CE-SDS [%] |
|---|---|---|---|---|---|---|---|---|
| REACT089 | 15.4 | 100 | 8.0 | 76.85 | 95.2 | 93.7 | 95 | 94 |
| REACT069[1] | 12.7 | 50 | 6.0 | 69.89 | 95.3 | 94.1 | 95 | 95 |
| REACT075 | 12.7 | 100 | 6.0 | 69.89 | 95.7 | 88.9 | 95 | 95 |
| REACT088[1] | 12.7 | 50 | 6.0 | 69.89 | 95.7 | 95.1 | 95 | 95 |
| REACT079 | 15.4 | 50 | 6.0 | 57.64 | 96.0 | 94.4 | 95 | 95 |
| REACT073[1] | 12.7 | 50 | 6.0 | 69.89 | 96.1 | 94.7 | 95 | 95 |
| REACT082 | 15.4 | 0 | 8.0 | 76.85 | 96.1 | 96.2 | 95 | 96 |
| REACT070 | 12.7 | 0 | 6.0 | 69.89 | 96.1 | 96.5 | 94 | 92 |
| REACT087 | 12.7 | 50 | 8.0 | 93.19 | 96.5 | 96.0 | 94 | 94 |
| REACT090 | 10.0 | 0 | 4.8 | 71.01 | 96.6 | 97.3 | 94 | 95 |
| REACT086 | 10.0 | 50 | 6.0 | 88.77 | 96.7 | 95.4 | 94 | 94 |
| REACT077 | 15.4 | 0 | 8.0 | 76.85 | 97.0 | 97.4 | 92 | 92 |
| REACT080 | 10.0 | 0 | 8.0 | 118.36 | 97.8 | 97.5 | 90 | 91 |

[1]Center Point.

As shown in Table 29, with respect to CEX activity in REACT.P samples, there was a group of six runs resulting in lower activity (<94%), which group contains all runs having high stirrer speed. Notably, all runs with no stirring resulted in highest CEX activity (more than 96%). Also it can be seen from Table 29, that CEX activity declined in REACT.P samples (compared to the CEX activity in REACT.PT300 samples) in runs carried out at 100 rpm, and (less pronounced) in runs carried out at 50 rpm. The highest decline in these runs is seen when the molar ratio of cysteine was at the lower end (e.g. decline from 89.4 to 84.0% in REACT085 where molar ratio was about 46:1 and similar in REACT075, REACT084 and REACT072).

TABLE 29

Input parameters and quality output parameter values REACT.PT300 and REACT.P sorted by ascending CEX for REACT.P samples.

| Run | Antibody content by ALC [mg/mL] | Stirrer speed during incubation [rpm] | Cysteine concn. [mM] | Approx. molar ratio cysteine to protein [M/M] | React. PT300 activity by CEX [%] | React.P activity by CEX [%] | React. PT300 purity by CE-SDS [%] | React.P purity by CE-SDS [%] |
|---|---|---|---|---|---|---|---|---|
| REACT085 | 15.4 | 100 | 4.8 | 46.11 | 89.4 | 84.0 | 95 | 94 |
| REACT075 | 12.7 | 100 | 6.0 | 69.89 | 95.7 | 88.9 | 95 | 95 |
| REACT084 | 10.0 | 100 | 4.8 | 71.01 | 94.3 | 88.9 | 95 | 95 |
| REACT072 | 12.7 | 50 | 4.8 | 55.92 | 94.5 | 90.2 | 96 | 95 |
| REACT091 | 10.0 | 100 | 8.0 | 118.36 | 92.4 | 91.3 | 93 | 94 |
| REACT089 | 15.4 | 100 | 8.0 | 76.85 | 95.2 | 93.7 | 95 | 94 |
| REACT069[1] | 12.7 | 50 | 6.0 | 69.89 | 95.3 | 94.1 | 95 | 95 |
| REACT079 | 15.4 | 50 | 6.0 | 57.64 | 96.0 | 94.4 | 95 | 95 |
| REACT073[1] | 12.7 | 50 | 6.0 | 69.89 | 96.1 | 94.7 | 95 | 95 |
| REACT088[1] | 12.7 | 50 | 6.0 | 69.89 | 95.7 | 95.1 | 95 | 95 |
| REACT086 | 10.0 | 50 | 6.0 | 88.77 | 96.7 | 95.4 | 94 | 94 |
| REACT087 | 12.7 | 50 | 8.0 | 93.19 | 96.5 | 96.0 | 94 | 94 |
| REACT082 | 15.4 | 0 | 8.0 | 76.85 | 96.1 | 96.2 | 95 | 96 |
| REACT070 | 12.7 | 0 | 6.0 | 69.89 | 96.1 | 96.5 | 94 | 92 |
| REACT090 | 10.0 | 0 | 4.8 | 71.01 | 96.6 | 97.3 | 94 | 95 |
| REACT077 | 15.4 | 0 | 8.0 | 76.85 | 97.0 | 97.4 | 92 | 92 |
| REACT080 | 10.0 | 0 | 8.0 | 118.36 | 97.8 | 97.5 | 90 | 91 |

[1]Center Point.

The statistical diagnosis (Table 30) indicates statistical significant models for purity by CE-SDS for both time points and for activity by CEX for REACT.P at the end of the selective reduction. The model for activity by CEX for REACT.PT300 shows lower statistical significance ($Q^2$ of 0.15).

TABLE 30

Model Diagnosis for the product quality output parameters of REACT.PT300 and REACT.P. A model that is in good agreement with the data will have a $R^2$ and $Q^2$ close to 1.0 and Model validity above 0.25. Models with low statistical significance have low $R^2$ and $Q^2$ values.

| Output | $R^2$ | $Q^2$ | Model validity | SD of replicates |
|---|---|---|---|---|
| REACT.PT300 | | | | |
| activity by CEX | 0.75 | 0.15 | 0.4 | 0.4 |
| purity by CE-SDS | 0.98 | 0.89 | −0.2 | 0.0 |
| REACT.P | | | | |
| activity by CEX | 0.92 | 0.75 | 0.48 | 0.5 |
| purity by CE-SDS | 0.87 | 0.59 | −0.2 | 0.0 |

Example 9.1.2.1—Modelling Evaluation of Product Quality Output Parameters at Time Point 1 (REACT.PT300)

The coefficient plot and the contour plot for CEX activity at time point REACT.PT300 demonstrate that the input parameter stirrer speed (stir) during incubation affects activity by CEX (data not shown). The parameters protein concentration (contA) and cysteine concentration (dil-c) show no statistically significant effect on activity by CEX within the investigated range. In order to achieve a high activity by CEX the stirrer speed during incubation should be low.

As shown in Table 29, all the experiments at time point REACT.PT300 had at least 90% purity by CE-SDS. The coefficient plot (data not shown) demonstrates that all three input parameters affect purity by CE-SDS. There are also quadratic terms for content by ALC (contA) and stirrer speed (stir). There are interaction terms of dilution factor by TITR3 addition (dil-c representing the cysteine concentration) and stirrer speed, as well as an interaction term of the dilution factor by TITR3 addition and content by ALC. In the contour plot (data not shown), the model coefficients as visualized indicate that high stirrer speed, high dilution factor by TITR3 addition (respectively a low cysteine concentration), and medium to high content by ALC positively influence purity by CE-SDS. All these settings reduce the reductive power of cysteine and positively influence antibody integrity. Nevertheless, as all runs have high purity by CE-SDS, and the whole investigated input parameter range is appropriate to ensure adequate purity by CE-SDS after selective reduction.

Example 9.1.2.2—Modelling of Product Quality Output Parameters at Time Point 2 (REACT.P)

Figure 13:
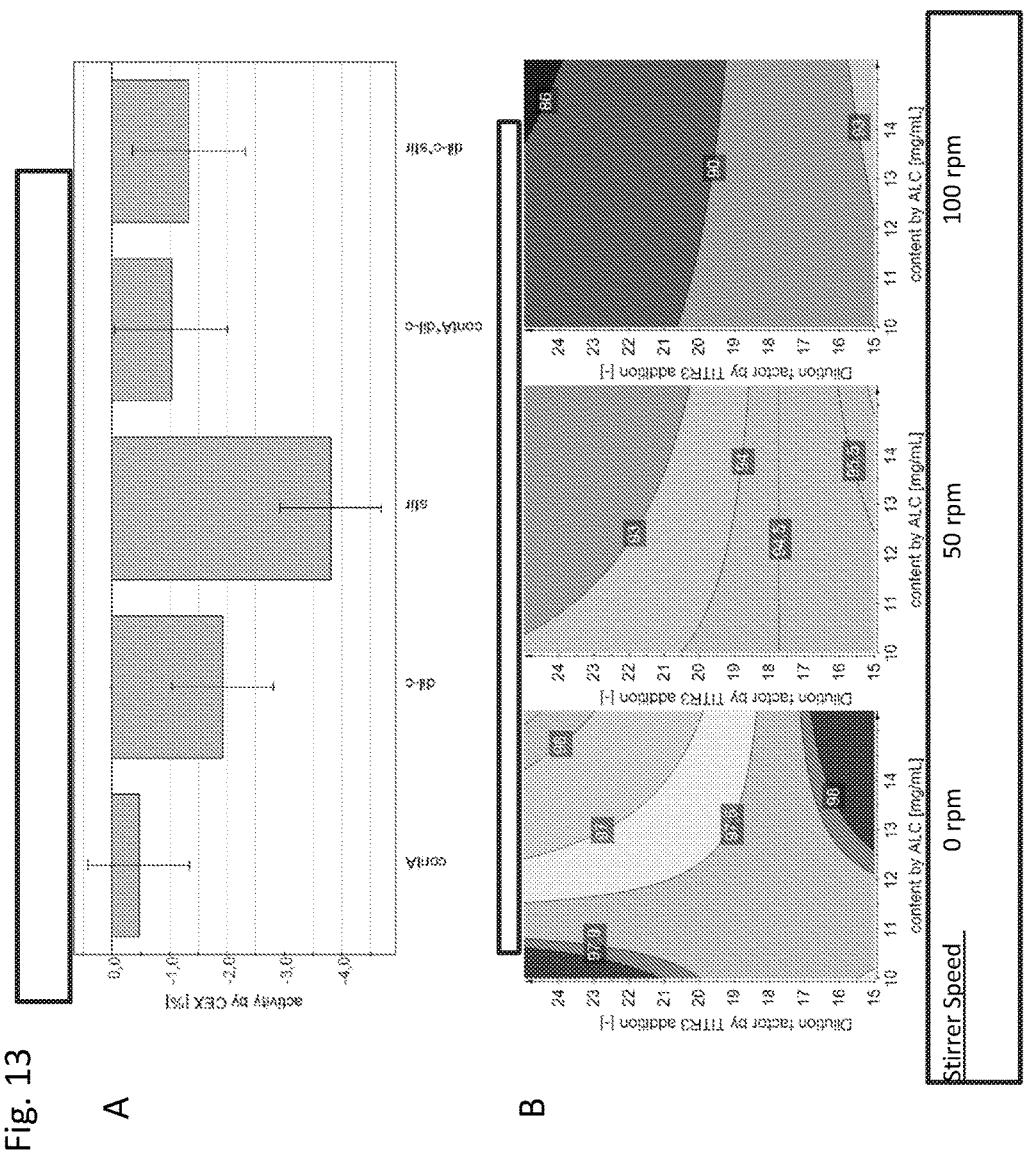
FIG. 13A shows a scaled and centered coefficient plot for activity by CEX of REACT.P.
FIG. 13B shows a 4D contour plot for activity by CEX of REACT.P. The plots of FIG. 13 analyze the impact of and interaction of cysteine concentration, protein content and stirrer speed on the output parameters activity by CEX and purity by CE-SDS.

The coefficient plot in FIG. 13A and contour plot in FIG. 13B for CEX activity at time point REACT.P confirms that especially the input parameter stirrer speed (stir) affects activity by CEX. Thus, in order to achieve a high activity by CEX, minimal stirring should be performed during incubation to limit oxygen transfer into the solution. Also, low dilution factor by TITR3 addition (dil-c, respectively a high cysteine concentration) is beneficial for activity by CEX after selective reduction. In addition, the interaction of stirrer speed and dilution by TITR3 addition has a significant—although small—impact on activity by CEX, whereas the interaction of content by ALC and dilution factor by TITR3 addition is borderline. The influence of content by ALC is not significant. The results clearly indicate that conditions which increase the reductive power, e.g., limited oxygen transfer by minimal stirring speed and higher cysteine concentration by lower dilution, result in higher activity by CEX.

As shown in Table 29, all the experiments at time point REACT.P had at least 90% purity by CE-SDS. The coefficient and contour plots (data not shown) for CE-SDS purity demonstrate that the input parameters content by ALC (representing protein concentration), dilution factor by TITR3 addition (dil-c, representing the cysteine concentration), and stirrer speed (stir, representing the oxygen transfer) have only a small effect on the purity by CE-SDS. The stirrer speed exhibits a quadratic effect and the interaction of dilution factor by TITR3 with stirrer speed is statistically significant. Purity by CE-SDS is improved by medium to high stirrer speed and high dilution factor by TITR3 addition. These settings reduce the reductive power of cysteine and positively influence antibody integrity. Nevertheless, as all runs meet the specified range for purity by CE-SDS, the whole investigated input parameter range is appropriate to ensure adequate purity by CE-SDS after selective reduction step.

Example 9.1.2.1—Relationship of Dissolved Oxygen Levels to Output Parameters

Figure 14:
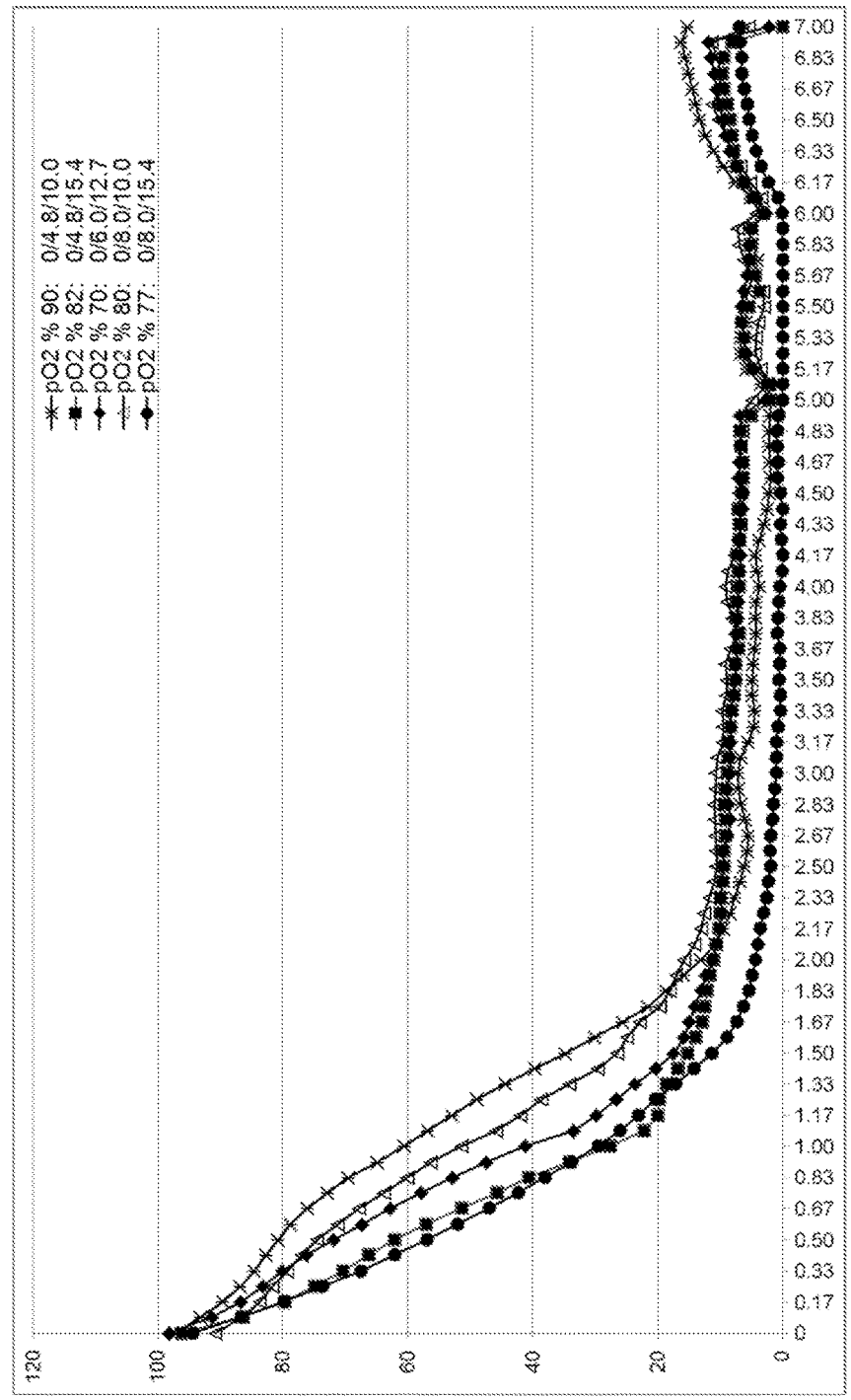
FIG. 14A shows the dissolved oxygen profiles of the process characterization runs at 0 rpm (the numbers in the legend indicate run number, stirrer speed and cysteine and antibody concentration).
FIG. 14B shows the dissolved oxygen profiles of the process characterization runs at 50 rpm (the numbers in the legend indicate run number, stirrer speed and cysteine and antibody concentration).
FIG. 14C shows the dissolved oxygen profiles of the process characterization runs at 100 rpm (the numbers in the legend indicate run number, stirrer speed and cysteine and antibody concentration).
FIG. 14D compares the dissolved oxygen profiles of the two runs performed at 50 mL scale at 50 rpm and 6.0 mM cysteine, one without antibody and the other with 12.7 g/L antibody.
Figure 14:
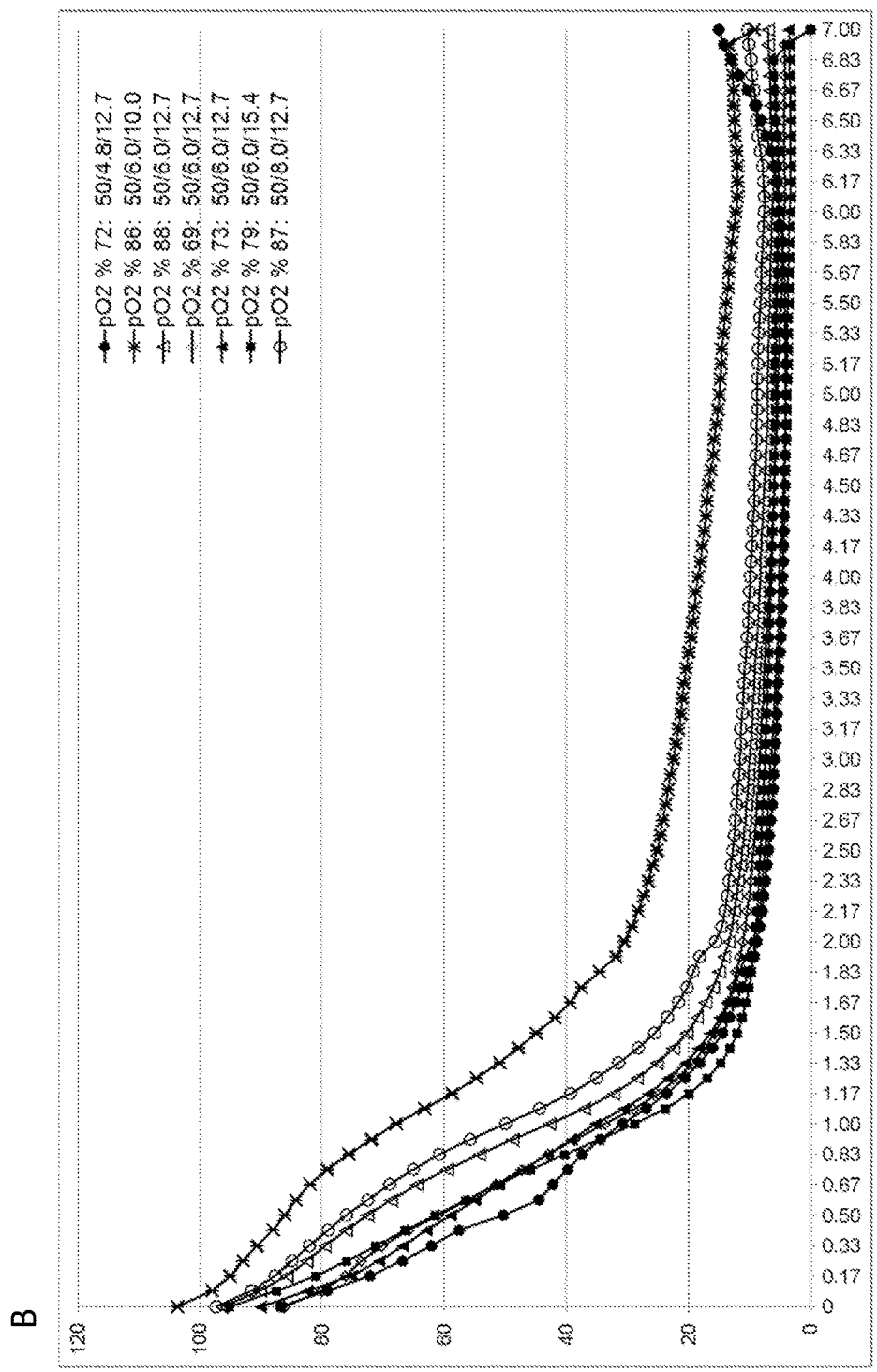
Figure 14:
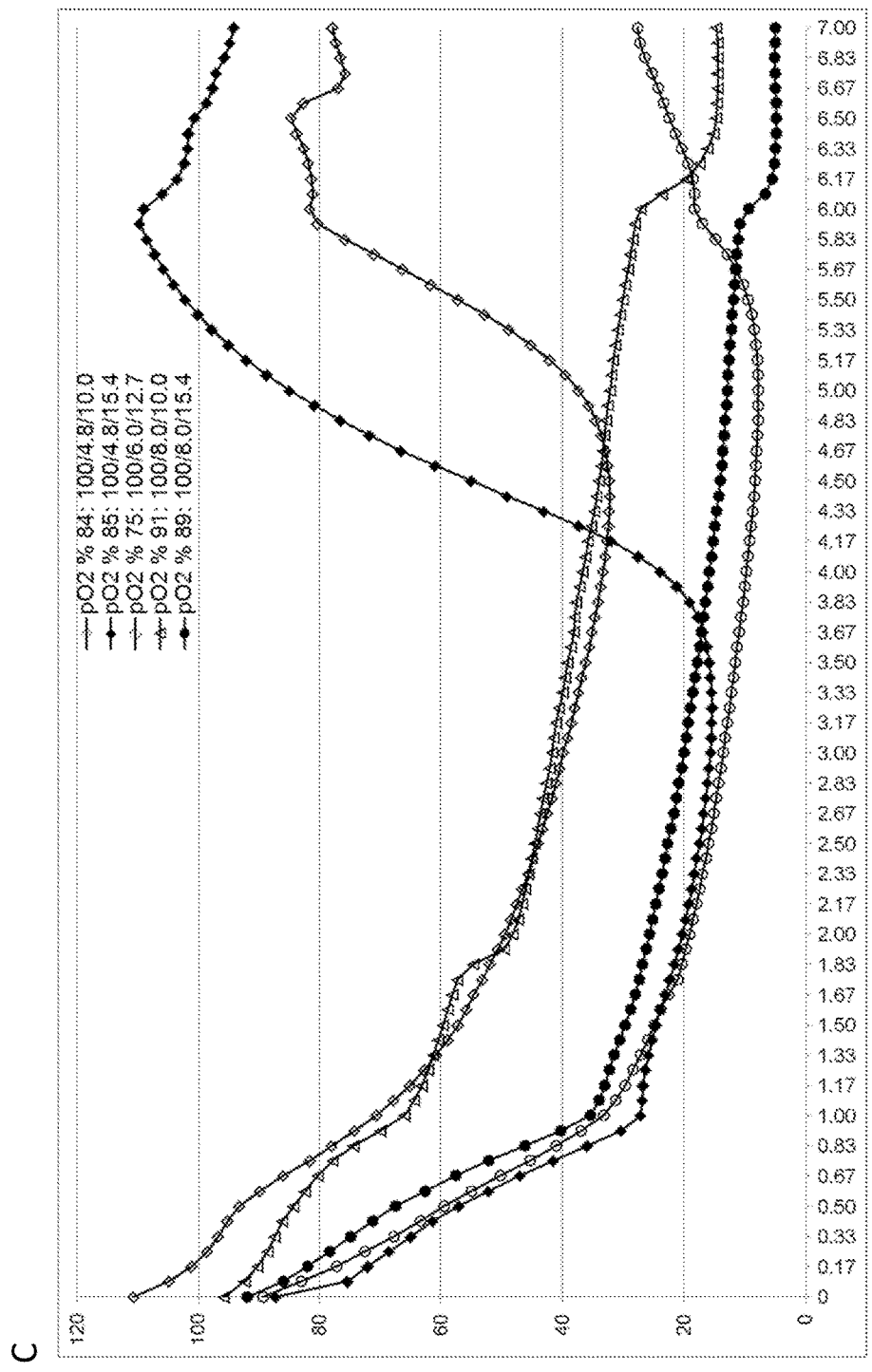

The oxygen profiles of the reactions shown in Table 26 were analyzed to determine the influence of the input parameters stirring speed, antibody content and cysteine concentration on levels of oxygen. Graphs of these oxygen profiles are provided in FIG. 14 (note: 0 to 1.00 on the x-axis corresponds to the 1 h heating phase, where stirring was at 50 rpm in all runs; 1.00 to 6.00 corresponds to the 5 h incubation phase, where stirring was either at 0 rpm [i.e., no stirring] 50, or 100 rpm; and 6.00 to 7.00 corresponds to the 1 h cooling phase, where stirring was at 50 rpm in all runs). All runs show a decrease of dissolved oxygen to low levels in the early phase. Notably, this decrease was less pronounced in runs with low antibody content (see runs REACT090 and REACT080 in the 0 rpm series (FIG. 14A), REACT086 in the 50 rpm series (FIG. 14B) and REACT084 and REACT091 in the 100 rpm series (FIG. 14C)) and most pronounced in runs having high antibody content (see profiles of the runs with 15.4 mg/mL graphs of FIG. 14).

In all runs without stirring during incubation (FIG. 14A), the $dO_2$ level remained below about 20% during both the incubation and cooling phase. Also, except for REACT086, in the runs using 50 rpm stirring during incubation (FIG. 14B), the $dO_2$ level stayed below about 20% during both the incubation and cooling step despite the oxygen transfer enabled in the incubation phase by 50 rpm stirring. However, in run REACT072, in which the cysteine concentration was low (4.8 mM), a slight increase of the oxygen level can be seen in the final cooling phase. The runs with 100 rpm stirring during incubation (FIG. 14C) showed very different profiles. First, as mentioned above, runs having low antibody content (10 mg/mL) (REACT084 and REACT091) showed a slower $dO_2$ decrease, which continued during the incubation phase. However, in run REACT084, in which the cysteine concentration was low (4.8 mM), the $dO_2$ level then increased during hours 5.00 and 6.00, the last hour of the incubation, to almost saturated level. Such an increase was observed also in run REACT085 even at an earlier time (hour 4.00). REACT085 also used a low level of cysteine, but high antibody content (15.4 mg/mL). An increase in the $dO_2$ level was also observed in run REACT075 during the cooling phase (hours 6.00 to 7.00). In run REACT075, the cysteine concentration was at the medium level (6.0 mM).

These profiles clearly indicate that oxygen is consumed in the reaction mixture at a rate higher than it is transferred into the mixture from the headspace, and that oxygen consumption is faster in runs having higher antibody concentration. This in turn suggests that the antibody itself may trigger $dO_2$ consumption. The increase of oxygen in later phases of selective reduction in runs having low cysteine levels indicates that the oxygen consumption is linked to a reaction with cysteine (Cys-SH), probably as follows: 4 Cys-SH+ $O_2 \rightarrow$ 2 Cys-SS-Cys+2 $H_2O$ and/or 2 Cys-SH+3 $O_2 \rightarrow$ 2 Cys-$SO_3H$. Indeed, the rate was fast enough to consume all cysteine after approximately 4 h in run REACT085, and after 5 h in run REACT084 (FIG. 14C). After consumption of the cysteine, $dO_2$ levels then recovered to saturated levels (100% $dO_2$).

Figure 14D:
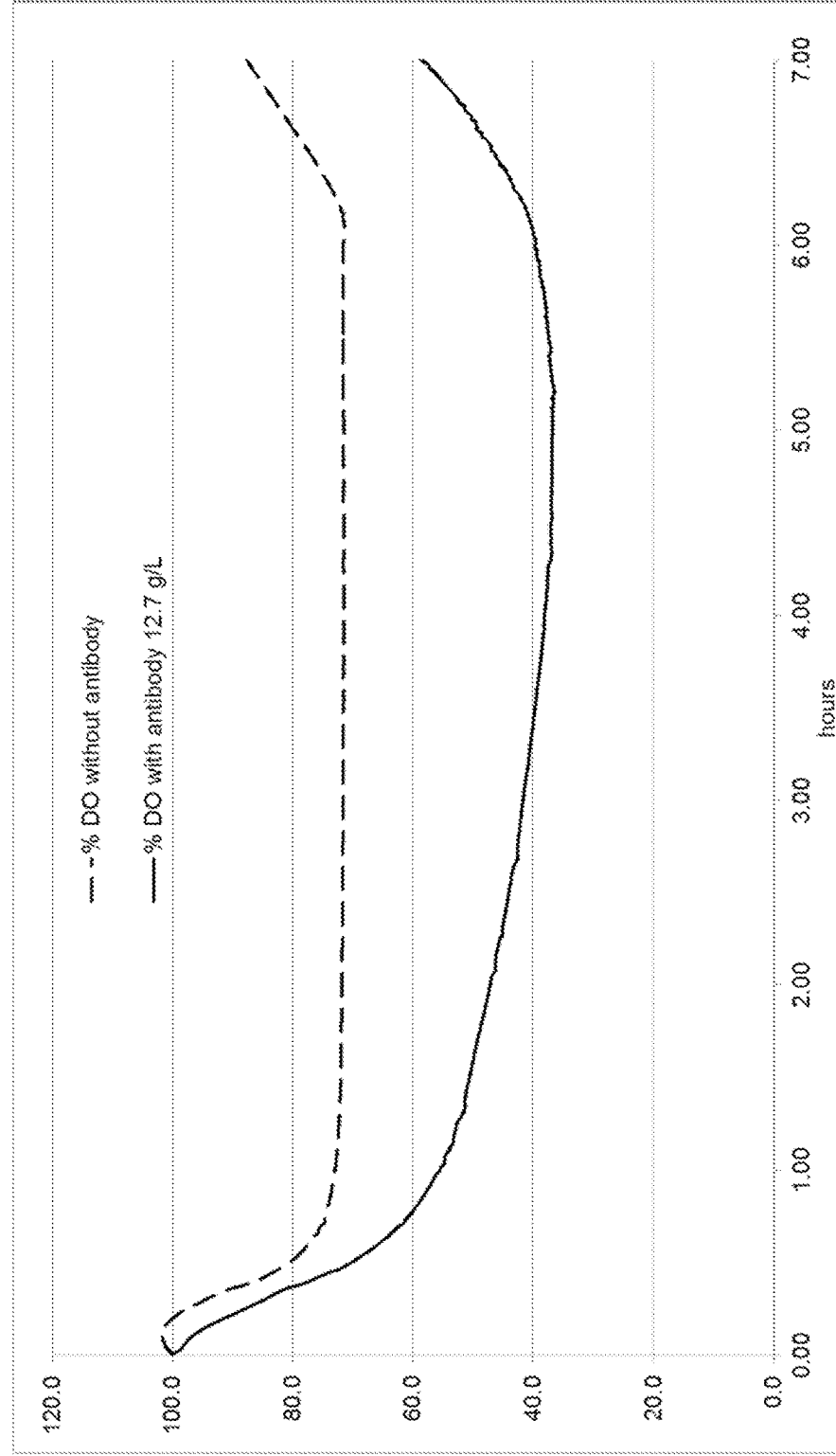

To study the impact of antibody on oxygen consumption, we performed two additional runs at 50 mL scale using 6 mM cysteine and a stirrer speed of 50 rpm. In one run, the antibody concentration was 12.7 mg/ml (molar ratio cysteine:antibody=69.89:1, i.e., about 70:1); in the other run the antibody concentration was zero. As shown in FIG. 14D, in the run without antibody there is a decrease of $dO_2$ to roughly 75% in the first hour, during which time the temperature of the reaction was raised from 20° C. to 37° C. This 75% decrease of $dO_2$ fits well to the reported decrease of $dO_2$ saturation concentration from 8.9 mg/L at 20° C. to 6.6 mg/L at 37° C. (U.S. Geological Survey TWRI Book 9, April, 98). The $dO_2$ level remains constant during the remainder of the incubation phase. Once the cooling phase begins (after 6 hours), there is an increase in the $dO_2$ level due to the lowering of temperature from 37° C. to 20° C. Thus, in the absence of antibody there is no consumption of oxygen in the solution, or consumption of oxygen by cysteine occurs at a low rate, such that the oxygen transfer from the headspace caused by stirring immediately compensates for that consumption. In contrast, in the run with antibody, there is a steady decrease in the $dO_2$ level up to approximately 5.5 hours. In the final 0.5 hour of the incubation phase there is a slight increase in the $dO_2$ level, followed by a stronger increase in the $dO_2$ level during the cooling phase (i.e., from hours 6 to 7). As such, in this antibody-containing run, probably most, if not all, cysteine was consumed after 5.5 hours. In fact, amino acid analysis of this run (data not shown) showed an elevated level of cystine, corresponding to almost complete consumption of the cysteine.

With this information, it is possible to correlate the low activity by CEX found in some runs with their $dO_2$ profiles. Run REACT085 (FIG. 14C) (molar ratio cysteine:antibody about 46:1) had 89.4% activity by CEX at REACT.PT300 (sample from 5.00 hour time-point) (see Table 28) because cysteine was consumed after the 4.00 time-point, leading to incomplete reduction of the antibody. REACT085 (FIG. 14C) at the later time point REACT.P (sample from endpoint 7.00 hour) had even less activity by CEX (84.0%, see Table 29) because the high level of oxygen in the last phase of the reaction, in the absence of cysteine, led to oxidative degradation of the antibody. Runs REACT084 (FIG. 14C) (molar ratio cysteine:antibody about 71:1) and REACT075 (FIG. 14C) (molar ratio cysteine:antibody about 71:1) were the two other runs with relatively low activity at the later time point REACT.P (both 88.9%), although the activity was high at the earlier REACT.PT300 time point. In these runs, the reduction of the antibody seemed to be complete at timepoint 5.00 hours (REACT.PT300 time point); however, degradation occurred by the later time point REACT.P due to the increased $dO_2$ level and absence of cysteine. Similarly, the relatively low activity found at later time point REACT.P for run REACT072 (FIG. 14B) (90.2%) (molar ratio cysteine:antibody about 56:1) is explained by the increase in the oxygen level during the cooling phase of the reaction. The high activities obtained in runs at 0 rpm (even in run REACT082, in which antibody content was high and cysteine concentration was low [molar ratio cysteine:antibody about 46:1]) occurred because the oxygen transfer rate was low and consumption of cysteine was therefore nominal, ensuring complete reduction (and also protection) against oxidative degradation during the later cooling phase of the reduction.

In conclusion, oxygen transfer should be kept low in the reduction system because oxygen consumes the reductant (cysteine), which consumption is mediated (or accelerated) by the antibody itself. There is therefore a two-fold impact of this cysteine consumption: 1) a loss of reductive power of the cysteine leads to incomplete deblocking of CysL97-SH at earlier time point REACT.PT 300; and 2) if there is no residual cysteine available to protect deblocked Cys97L-SH during the time between REACT.P300 and REACT.P, then reoxidation of deblocked Cys97L-SH can occur.

Example 9.2—Process Characterization: Worst/Best Case Scenarios

The main purpose of the worst/best case studies was the characterization of the input factors of the selective reduction step that were not tested during a design of experiments (DOE) study, but were assessed as possibly important in the process risk analysis. The data are also used to define the proven acceptable ranges and to support classification of the input parameters based on impact of their effect on product attributes.

Example 9.2.1—Experimental Design and Methods

Increased heating time was assessed as possibly significant, as it increases the oxygen transfer into the selective reduction solution due to extended stirring duration, which can lead to reduced reductive power by conversion of cysteine to cystine and hence less selective reduction of the antibody. For the same reason, enhanced initial $dO_2$ level was assessed as possibly significant input parameter.

The oxidation of the sulfhydryl group of cysteine is pH dependent. Consequently, the influence of pH was assessed as possibly significant input parameter.

High reductive power can lead to over-reduction of the antibody and an extended cooling time could promote antibody reassembly. Thus, extended cooling time was also assessed as possibly significant input parameter Although the temperature was already tested during earlier process development (32-42° C.), it was assessed as possibly significant. Typically, the chemical reaction rate decreases with a lower temperature. Therefore, the kinetic was determined at the upper and lower limit in dedicated runs.

The incubation time was also investigated. A low incubation time could lead to higher levels of over-reduced product in the selective reduction pool. Conversely, the extended incubation time could lead to lower activity by CEX as shown in the response surface design results (see Table 29, c.f. CEX activity of REACT.PT300 and REACT.P samples).

Three worst/best case sequences were defined to assess the influence of the parameters described above on the selective reduction step. The input parameters to assess the reductive power in a worst/best case sequence are shown in Table 30. The second worst/best case sequence was created to evaluate the influence of temperature on the selective reduction step (Table 31). The influence of the incubation time was evaluated in the third worst/best case study according to the input parameter listed in Table 32. The product quality output parameters used to assess the results of the worst/best case studies are activity by CEX and purity by CE-SDS.

TABLE 30

Input parameters to assess influence of reductive power.

| Name | Unit | Lower limit | Upper limit |
| --- | --- | --- | --- |
| Heating time including stirring | [min] | 45 | 90 |
| Cooling time including stirring | [min] | 45 | 90 |
| Dissolved oxygen at start | [%] | 60 | 100 |
| Process pH | [-] | 7.8 | 8.2 |

TABLE 31

Input parameters to assess influence of incubation temperature. 1) 32° C. was tested, as the reaction rate of the selective reduction at 18° C. was not sufficient, resulting in incomplete reactiviation.

| Name | Unit | Lower limit 1 | Lower limit 2 [1] | Upper limit |
| --- | --- | --- | --- | --- |
| Incubation temperature | [° C.] | 18 | 32 | 42 |

TABLE 32

Input parameters to assess influence of incubation time.

| Name | Unit | Lower limit | Upper limit |
| --- | --- | --- | --- |
| Incubation time | [min] | 210 | 330 |

Dedicated runs were performed to evaluate the influence of additional possibly important parameters. Secukinumab, INAKT.F (stored below −60° C.) originating from manufacturing-scale run B008530 was used. Buffers AIN457-TITR1, AIN457-TITR2 and AIN457-TITR3 are as described in Example 10. The experiments were performed on the qualified scale-down model (described in detail in Example 10) in an open stirred bioreactor (maximum 2 L volume) with pH, dissolved oxygen, stirrer speed and temperature monitoring For all runs, the process parameters from Table 27 were applied. All input parameters that were not part of the individual studies were held constant at the target in Table 27 within the operating range of the standard sequence.

Example 9.2.2—Results of Worst/Best Scenarios

The experimental design plan and the output parameters (purity by CE-SDS and activity by CEX) for investigation of the influence of heating time, cooling time, $dO_2$ at start and process pH, are shown in Table 33. The experimental design plan and the output parameters (purity by CE-SDS and activity by CEX) for investigation of the influence of incubation temperature are shown in Table 34. The experimental design plan and the output parameters (purity by CE-SDS and activity by CEX) for investigation of the incubation time are displayed in Table 35.

As shown in Table 33, duplicate runs with low reductive power, as well as high reductive power yielded high activity by CEX as well as purity by CE-SDS. Hence, the process is able to cover variations of the input parameters heating time and cooling time (including stirring), $dO_2$ level at start, and process pH within the tested ranges.

TABLE 33

Experimental design plan and output parameters for investigation of the influence of heating time, cooling time, $dO_2$ at start and process pH.

| Run | Heating time [min] | Cooling time [min] | Dissolved oxygen at start [%] | Process pH [-] | Activity by CEX [%] | Purity by CE-SDS [%] |
| --- | --- | --- | --- | --- | --- | --- |
| REACT076 [1] | 90 | 90 | 100 | 7.8 | 96.4 | 94 |
| REACT078 [2] | 45 | 45 | 60 | 8.2 | 97.4 | 93 |
| REACT098 [1] | 90 | 90 | 100 | 7.8 | 95.8 | 95 |
| REACT100 [2] | 45 | 45 | 60 | 8.2 | 94.1 | 94 |

[1] duplicate runs run with lower reductive power because of lower pH, higher $dO_2$ starting level and longer heating and cooling time.
[2] duplicate runs with higher reductive power because of higher pH, lower $dO_2$ starting level and shorter heating and cooling time.

The results of the experiments to evaluate the influence of the incubation temperature are shown in Table 34. It can be seen that purity by CE-SDS was always high, whereas high activity by CEX was obtained only in the runs of 32° C. and above.

TABLE 34

Experimental design plan and output parameters for investigation of the influence of incubation temperature. 1) Additional center point run.

| Run | Incubation temperature [° C.] | Activity by CEX [%] | Purity by CE-SDS [%] |
| --- | --- | --- | --- |
| REACT093 | 42 | 94.9 | 94 |
| REACT095 | 42 | 95.2 | 94 |
| REACT107 | 32 | 95.9 | 95 |
| REACT109 | 32 | 97.3 | 95 |
| REACT092 | 18 | 91.2 | 93 |
| REACT099 | 18 | 90.4 | 95 |
| REACT106 [1] | 37 | 95.6 | 96 |

Figure 15:
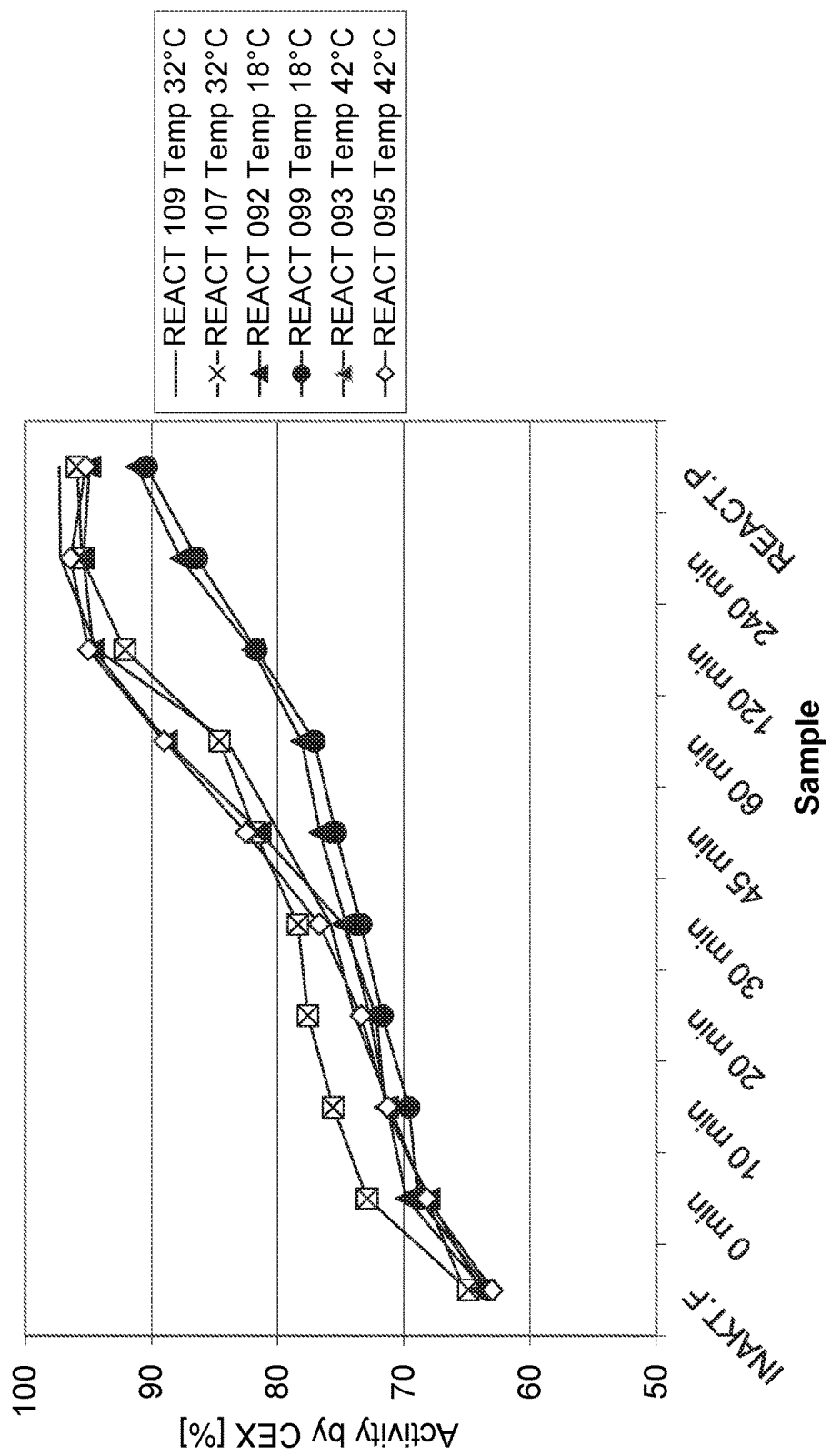
FIG. 15 shows selective reduction kinetics of activity by CEX at different incubation temperatures.

Additionally the kinetic of the activity by CEX was determined at the different incubation temperatures. These results are shown in FIG. 15. It can be seen that kinetics at 42° C. is faster than at 32° C., especially in the later phase (60 min and more). However, at both temperatures the same plateau is reached at 240 min and REACT.P. At 18° C., the reaction rate is slower, leading to lower increase of activity by CEX within the tested step duration.

The results of the experiments to evaluate the influence of the incubation time are shown in Table 35. In all cases high activity and purity was obtained.

TABLE 35

Experimental design plan and output parameters for investigation of the influence of incubation time. 1) low incubation time. 2) high incubation time.

| Run | Incubation time [min] | Activity by CEX [%] | Purity by CE-SDS [%] |
|---|---|---|---|
| REACT081[1] | 210 | 96.7 | 95 |
| REACT083[2] | 330 | 96.3 | 95 |
| REACT094[1] | 210 | 95.2 | 93 |
| REACT096[2] | 330 | 96.2 | 94 |

Example 9.3—Classification and Justification of Process Parameters

Example 9.3.1—Response Surface Design Study: Acceptable Ranges

Purity by CE-SDS was at least 90% in all experiments at time point 1 (REACT.PT300) and at the end of the selective reduction (REACT.P). To achieve high levels of purity by CE-SDS, the input parameter dilution factor by TITR3 addition should be set to high and stirrer speed should be set center to high. These conditions correspond to a low reductive power due to lower cysteine concentration and increased oxygen transfer over the headspace. The input parameter content by ALC, i.e., the antibody concentration, has significant influence at time point 1 (REACT.PT300) during the selective reduction step, and the ideal is around the center point. The influence of antibody concentration (content by ALC) on the absolute value of purity by CE-SDS is minor within the investigated ranges. Nevertheless, the specified purity value was met in all experiments and the whole range investigated for the parameters content by ALC (antibody concentration), dilution factor by TITR3 addition (cysteine concentration) and stirrer speed (oxygen transfer) is appropriate to ensure adequate purity by CE-SDS after selective reduction.

Activity by CEX was at least 90% for all but REACT085 (see Table 28) at time point 1 (REACT.PT300). This experiment was performed with stirrer speed at its high level, representing a higher oxygen transfer. Despite expectations, a longer incubation time (i.e., 60 additional minutes, time point REACT.P) was not particularly beneficial for the output parameter activity by CEX, as an additional two experiments (REACT075 and REACT084, see Table 29) displayed activity by CEX below 93%. These experiments have either high stirrer speed or high level of dilution factor by TITR3 addition, representing a low cysteine concentration and increased oxygen transfer over the headspace. These results suggest achieve highest activity by CEX, the input parameter stirrer speed should be set to a low level, implying a low oxygen transfer, and dilution factor by TITR3 addition should be set to center point or low level, implying a higher cysteine concentration. The input parameter content by ALC, representing the antibody concentration, had no significant influence on activity by CEX in these experiments.

The input parameter stirrer speed which mediates (oxygen transfer from headspace into solution is important for the selective reduction step and should be set to its lower level to ensure adequate activity by CEX. According to an additional manufacturing-scale run (B018838, data not shown) a maximum of 15 minutes stirring per hour was tested, resulting in an acceptable product quality after the selective reduction step. However, the results of Example 8 reveal that the oxygen transfer into solution by stirring is unique for each scale and setup and is controlled indirectly. Therefore, stirring conditions during incubation should be assessed in case of, e.g., process changes or scale-up. Stirring during incubation, which indirectly represents the level of $dO_2$ transfer into the reaction solution, is classified as a significant input parameter from a process perspective.

The input parameters content by ALC, namely the antibody concentration, and dilution factor by TITR3 addition, namely the cysteine concentration, show statistically significant effects, but are well-controlled and have minor influence on the selective reduction step. Hence, they are classified as non-key from a process point of view. As long as the mixing time during incubation is within the acceptable range, variations within the investigated ranges of cysteine concentration and antibody concentration will lead to adequate process performance and product quality after the selective reduction step. A list with the proven acceptable ranges for these input parameters is shown in Table 36.

TABLE 36

Acceptable ranges for stirrer speed during incubation, content by ALC and dilution factor by TITR3 addition (cysteine concentration). 1) according to characterization run at manufacturing-scale, batch B018838, SITE A, at 4 h incubation time.

| Name | Unit | Lower limit | Upper limit |
|---|---|---|---|
| Mixing time during incubation | [min/h] | 0 | 15[1] |
| content by ALC | [mg/mL] | 10 | 15.4 |
| dilution factor by TITR3 addition | [-] | 15 (8 mM cysteine, 1.3 mM EDTA) | 25 (4.8 mM cysteine, 0.8 mM EDTA) |

Example 9.3.2—Worst/Best Case Studies: Acceptable Ranges

The input parameters heating time and cooling time (including stirring), $dO_2$ level at start and process pH have no significant influence regarding the product quality attributes activity by CEX and purity by CE-SDS within the investigated range displayed in Table 37. However, due to the experience of the response surface design, too high oxygen transfer into the selective reduction solution should be avoided, as it reduces reductive power. The oxygen transfer is specific for each scale and setup, but in an aerobic process is controlled indirectly by other process conditions, such as stirring and airflow into the headspace. Therefore, stirring during heating and cooling, which affects the oxygen transfer, must be carefully evaluated, especially in case of, e.g., a process changes, process transfer, or scale-up. Accordingly, the heating and cooling time (including stirring) are classified as significant parameters from a process point of view. Although a range for heating and cooling time (including stirring) of 45-90 minutes was tested, the acceptable range was set to ≤90 minutes, as 90 minutes heating and cooling time (including stirring) reflects the worst case with respect to oxygen transfer leading to appropriate activity by CEX and purity by CE-SDS.

TABLE 37

Tested ranges of heating time, cooling time, dissolved oxygen at start and process pH.

| Name | Unit | Lower limit | Upper limit |
|---|---|---|---|
| Heating time including stirring | [min] | 45 | 90 |
| Cooling time including stirring | [min] | 45 | 90 |
| Dissolved oxygen at start | [%] | 60 | 100 |
| Process pH | [-] | 7.8 | 8.2 |

The results of the experiments investigating the input parameter incubation temperature demonstrate that an incubation temperature of 18° C. leads to slow reaction kinetics resulting in insufficient reactivation. The low temperature is not sufficient to increase activity by CEX within an incubation time of 240 min to levels higher than 93.0%. Therefore, the tested range of 18-42° C. is narrowed to 32-42° C. to ensure adequate activity by CEX after the selective reduction step, although the product quality attribute purity by CE-SDS can be achieved within an incubation temperature range of 18-42° C. The acceptable range for incubation temperature is therefore a lower limit of 32° C. and an upper limit of 42° C.

Finally, the tested range of 210-330 min incubation time ensures adequate activity by CEX and purity by CE-SDS after selective reduction step.

Summary and Conclusions Drawn from Example 9

Based on the results of the process characterization study, the acceptable ranges for the investigated process input parameters were defined. The selective reduction step is characterized by the two product quality output parameters purity by CE-SDS and activity by CEX. The parameter classification and acceptable ranges are summarized in Table 38. The ratio of cysteine:antibody for the PAR is about 46:1 to about 118:1. The ratio of cysteine:antibody for the SOR is about 54:1 to about 83:1.

TABLE 38

Input parameters of selective reduction step including classification. 1) after dilution with WFI before pH adjustment and TITR3 addition, 2) before heating. 3) during incubation. 4) according to characterization run at manufacturing-scale, batch B018838, at 4 h incubation time. 5) related to intermediate volume after addition of WFI and pH adjustment with TITR1.

| Input Parameter | Unit | Suggested Operating Range (SOR) | Proven Acceptable Range (PAR) |
|---|---|---|---|
| Content by ALC [1] | [mg/mL] | 12.0-15.0 | 10.0-15.4 |
| Dilution factor by TITR3 addition (cysteine concentration) [5] | [-] | 1:18-1:22 (5.5-6.7 mM cysteine, 1.1-0.9 mM EDTA) | 1:15-1:25 (4.8-8.0 mM cysteine, 1.3-0.8 mM EDTA) |
| Dissolved oxygen at start | [%] | ≥80 | ≥60 |
| Heating time including stirring | [min] | ≤75 | ≤90 |
| Mixing time during incubation | [min/hour] | 0-5 | 0-15 [4] |
| Incubation time | [min] | 240-300 | 210-330 |
| Cooling time including stirring | [min] | ≤75 | ≤90 |
| Process pH [2] | [pH] | 7.9-8.1 | 7.8-8.2 |
| Process temperature [3] | [° C.] | 35-39 | 32-42 |

At the beginning of the selective reduction step, oxygen moderates the reductive power of the cysteine, while continuous transfer of oxygen into the solution results in an increased oxygen level and less antibody activity by CEX. However, at the end of the selective reduction step, the introduction of oxygen could enhance the formation of the disulfide bonds in the antibody that were disassociated at the beginning of the reaction when the reductive power was high, and therefore oxygen is important to ensure adequate purity by non-reducing CE-SDS. The importance of the oxygen transfer for antibody activity is demonstrated by the results of the response surface design study, in which a significant effect of the stirrer speed on oxygen transfer, and hence product activity by CEX, was observed (see Table 28 and 29). However, stirrer speed has a different effect on the level of $dO_2$ depending on the size of the vessel, the size of the stirrer, the type of stirrer, etc. Thus, it is important to identify a variable that can be used to compare the oxygen transferred into a solution between physical setups.

Example 10: Oxygen Transfer Rate ($k_L a^*$) of the Scale-Down Model

In the previous example, we showed that, inter alia, the amount of $dO_2$ present during selective reduction, particularly during the incubation step has a strong influence on the quality and activity of secukinumab. When selective reduction is performed under aerobic conditions, the level of oxygen in the reaction is not controlled directly, but via other operating conditions, e.g., stir speed and airflow to the headspace. The physical setup of each reaction also influences the level of oxygen present in the reaction mixture (the equipment and operating conditions together form a "system"). "$k_L a^*$" can be used to compare the oxygen transferred into a solution between physical setups and during particular antibody processing steps (see, e.g., Garcia-Ochoa and Gomez (2009) Biotechnology Advances 27:153-176; Bandino et al. (2001) Biochem. Engineering J. 8:111-119; Juarez and Orejas (2001) Latin Am. Appl. Res. 31:433-439; Yange and Wang (1992) Biotechnol. Prog. 8:244-61). The $k_L a^*$ represents the amount of oxygen transferred into a solution over time via the headspace without sparging. This value is specific for each setup and scale, and depends on stirrer type, stirrer speed, filling volume and surface area of the solution in contact with the headspace, which is influenced by the individual geometry of each vessel. While the $k_La^*$ of each physical setup differs, because the level of oxygen in the solution during the selective reduction step significantly effects the activity and integrity of secukinumab, we expect that the selective reduction step, when performed in systems displaying similar $k_La^*$ ranges, will lead to preparations of secukinumab having similar quality.

The $k_La^*$ cannot be directly determined in the oxygen transfer experiments. Instead, the $dO_2$ in a test solution is replaced by nitrogen and the increase of $dO_2$ over time is monitored using a calibrated $dO_2$ probe, which allows creation of an experimental $dO_2$ curve. Thereafter, the $k_La^*$ value is calculated for the particular system by adapting the experimental $dO_2$ curve to a saturation curve (e.g., using Mathcad®) according to the equation shown below:

DO=C×$(1-e^{-kLa^*x(t-t0)})$, where DO=the measured value of dissolved oxygen, C is the saturation value of oxygen (meaning 100% when stirred infinitely and saturation is achieved), e=2.718281 . . . , t=time point corresponding to the DO value, and $t_0$=starting time point.

The equation represents the integrated form of an empirical formula established for determination of the oxygen transfer into solutions ($k_La^*$ value). The formula was confirmed by different authors in various experiments (Doran, P. M. 1995. Bioprocess Engineering Principles, Academic Press, San Diego, Calif., chapter 9.10.2, p. 210-213).

Example 10.1—Experimental and Statistical Design Methods

Because the dissolved oxygen level is an important influencing factor for redox reactions, the oxygen transfer was assessed for qualification of a scale-down model and for comparison with manufacturing-scale.

A statistical design was used to determine the dependency of the $k_La^*$ value with the input parameters of volume, air-flow into headspace, stirrer-speed and stirrer type. The input parameters are listed in Table 39. The factors were investigated on 3 levels, each according to a statistical design plan. The output parameter is the $k_La^*$ value.

TABLE 39

Input parameters for $k_La^*$ value determination of the scale-down model.

| Name | Abbreviation | Unit | Lower limit | Upper limit |
| --- | --- | --- | --- | --- |
| Volume | Vol | [L] | 0.7 | 1.7 |
| Airflow (headspace) | Air | [L/min] | 0 | 0.5 |
| Stirrer speed | Stir | [rpm] | 50 | 200 |

To determine the $k_La^*$ value for each sample, a 2 L bioreactor was filled with water and heated to 37° C. Airflow was controlled by a mass-flow meter and applied to the headspace. Thereafter, the solution was sparged with nitrogen gas to remove $dO_2$ from the water. Then, constant stirring was applied using a rushton turbine (radial). Over the course of time, the level of $dO_2$ in the water was recorded using an oxygen probe (calibrated at room temperature, about 18-25° C.) until the $dO_2$ reached 90%. Thereafter, the $k_La^*$ value was calculated by adapting the experimental $dO_2$ curve to a saturation curve as described above.

A Central Composite Face Centered design (CCF) with 3 center point runs was used. The design was chosen to determine the correlation between the most important process parameters and their influence on $k_La^*$. This type of design supports calculation of mathematical models with linear, interaction and quadratic terms.

Example 10.3—Output Parameter ($k_La^*$) Values

The values for the experimental conditions and the process performance output parameter $k_La^*$ are listed in Table 40.

TABLE 40

Statistical design-performed sequence and experimental conditions.

| Run [-] | Airflow [L/min] | Volume [L] | Stirrer speed [rpm] | Measured $k_La^*$ [1/h] |
| --- | --- | --- | --- | --- |
| 1 | 0.50 | 0.7 | 50 | 0.83 |
| 2 | 0.10 | 0.7 | 200 | 0.70 |
| 3 | 0.50 | 0.7 | 200 | 3.58 |
| 4 | 0.10 | 0.7 | 50 | 0.41 |
| 5 | 0.25 | 0.7 | 125 | 1.97 |
| 6 | 0.25 | 1.2 | 125 | 0.97 |
| 7 | 0.25 | 1.2 | 125 | 0.86 |
| 8 | 0.25 | 1.2 | 125 | 0.98 |
| 9 | 0.25 | 1.2 | 200 | 1.36 |
| 10 | 0.25 | 1.2 | 125 | 0.77 |
| 11 | 0.50 | 1.2 | 125 | 1.07 |
| 12 | 0.25 | 1.2 | 125 | 1.05 |
| 13 | 0.10 | 1.2 | 125 | 0.73 |
| 14 | 0.25 | 1.2 | 50 | 0.54 |
| 15 | 0.25 | 1.2 | 125 | 0.86 |
| 16 | 0.50 | 1.7 | 200 | 0.73 |
| 17 | 0.50 | 1.7 | 50 | 0.22 |
| 18 | 0.00 | 1.7 | 200 | 0.48 |
| 19 | 0.25 | 1.7 | 125 | 0.62 |
| 20 | 0.00 | 1.7 | 50 | 0.24 |

Example 10.4—Statistical Diagnostic for Output Parameter $k_La^*$

The quality of the models is represented by 4 tools; namely the $R^2$, $Q^2$, Model validity and the Standard Deviation (SD) of replicates. A model that explains the data well will have a $R^2$ and $Q^2$ close to 1.0 and Model validity above 0.25. In a model analysis, it was recognized that evaluation of the $k_La^*$ results without transformation leads to a model in which the residuals do not meet the requirements of a normal distribution. This indicates that a transformation of the $k_La^*$ value is necessary to describe the results in an adequate manner, which is sometimes observed for common $k_La^*$ measurements in bioreactors. The model diagnostics for the process performance output parameter are $R^2$=0.98; $Q^2$=0.91 (following transformation by the power of −0.5); model validity=0.56 and standard deviation of replicates=0.06, indicating a model with high statistical significance.

Example 10.5—Description of Mathematical Model

In the N-plot of residuals the standardized residuals (residuals of the responses divided by the standard deviation) are plotted on the horizontal axis and the normal probability on the vertical axis. Outliers can be graphically identified when they lay outside off 4 standardized residuals. Also, non-linear plots can indicate a model which needs an output parameter transformation ("Design of Experiments—Principles and Applications," (1999-2008) MKS Umetrics AB, ed. Eriksson et al.). The N-plot of residuals for the process output parameter $k_La^*$ (data not shown) indicates a good fit of the experimental result with the model. The values fit close to the regression line, which means that the model transformation is adequate (the standardized residuals meet the requirements of a normal distribution). Additionally, all experimental values are inside the range of ±3 standardized residuals, indicating that the measured values do not include any outliers.

The coefficient plot for the process output parameter (data not shown), indicates that the input parameters, airflow, volume and stirrer speed have significant influence on the process parameter $k_La^*$. The contour plot (data not shown) illustrates the effect of airflow, volume and stirrer speed on $k_La^*$—the higher the airflow, the lower the volume (i.e. larger the headspace) and the higher the stirrer speed, the higher is the oxygen transfer over the head-space expressed as $k_La^*$.

Using the contour and coefficient plots, the corresponding $k_La^*$ values of the experimental conditions were predicted with MODDE 8.02 by use of the statistical model. The results are shown in Table 41, which demonstrates the $k_La^*$ range that was tested during process characterization (see Example 9) using the scale-down model.

TABLE 41

Parameter settings and corresponding $k_La^*$ values used during process characterization studies.

| | Airflow [L/min] | Volume [L] | Stirrer speed [rpm] | Predicted $k_La^*$ [1/h] |
|---|---|---|---|---|
| Low stirrer speed | 0 | 1.2 | 0 | 0.18 |
| Center point | 0 | 1.2 | 50 | 0.27 |
| High stirrer speed | 0 | 1.2 | 100 | 0.37 |
| Worst/best case experiments | 0 | 1.0 | 50 | 0.28 |

Example 11: Oxygen Transfer Rate ($k_La^*$) at Manufacturing Scale

The $k_La^*$ during constant stirring (i.e., the type of stirring used during the heating and cooling phase of the selective reduction process) at manufacturing-scale (1800 L vessel) was determined.

Example 11.1—Determination of the $k_La^*$ Value at Manufacturing-Scale at SITE A

Example 11.1.1—Experimental and Statistical Design Methods

A statistical design was used to determine the dependency of the $k_La^*$ within the tested input parameter ranges. The input parameters are listed in Table 42 below. The factors are investigated on 3 levels each according to the statistical design plan. The output parameter is the $k_La^*$ value.

TABLE 42

Input parameters for $k_La^*$ value determination at manufacturing-scale SITE A.

| Name | Abbreviation | Unit | Lower limit | Upper limit |
|---|---|---|---|---|
| Volume | Vol | [L] | 400 | 800 |
| Stirrer speed | Stir | [rpm] | 100 | 300 |
| Temperature | Temp | [° C.] | 16 | 48 |

These experiments at SITE A were performed in a stainless steel vessel with a maximum working volume of 1800 L, a height of 2.7 m and a diameter of 1.0 m. To determine the $k_La^*$ value for each sample, the vessel was filled with water and heated to the indicated temperature. Thereafter, nitrogen gas was applied to the headspace to remove $dO_2$ from the water. Then, constant stirring was applied (using a propeller stirrer from the bottom). Over the course of time, the level of $dO_2$ in the water was recorded using an oxygen probe (calibrated at room temperature, e.g., 18-25° C.) until the $dO_2$ reached 90%. Thereafter, the $k_La^*$ value was calculated by adapting the experimental $dO_2$ curve to a saturation curve as described above. The input parameters and the corresponding results are shown in Table 43.

A Central Composite Face Centered (CCF) design with 4 center points was used. The design was chosen to determine the correlation between the most important input parameters and their influence on the oxygen transfer. This type of design supports calculation of mathematical models with linear, interaction and quadratic terms.

Example 11.1.2—Output Parameter ($k_La^*$) Values

The values for the experimental conditions and process performance output parameter $k_La^*$ are listed in Table 43.

TABLE 43

Statistical design-performed sequence and experimental conditions.

| Run [-] | Volume [L] | Stirrer speed [rpm] | Temperature [° C.] | Measured $k_La^*$ [1/h] |
|---|---|---|---|---|
| 1 | 602 | 99 | 33 | 0.20 |
| 2 | 410 | 99 | 16 | 0.47 |
| 3 | 605 | 200 | 33 | 0.29 |
| 4 | 596 | 201 | 16 | 0.22 |
| 5 | 419 | 300 | 49 | 1.69 |
| 6 | 804 | 100 | 49 | 0.12 |
| 7 | 388 | 201 | 32 | 1.01 |
| 8 | 808 | 300 | 16 | 0.22 |
| 9 | 637 | 201 | 33 | 0.27 |
| 10 | 803 | 201 | 33 | 0.20 |
| 11 | 600 | 300 | 33 | 0.37 |
| 12 | 808 | 100 | 16 | 0.09 |
| 13 | 400 | 300 | 16 | 1.24 |
| 14 | 815 | 300 | 49 | 0.39 |
| 15 | 612 | 201 | 49 | 0.29 |
| 16 | 616 | 201 | 33 | 0.30 |
| 17 | 608 | 200 | 33 | 0.23 |
| 18 | 396 | 100 | 49 | 0.97 |

Example 11.1.3—Statistical Diagnostic for Output Parameter $k_La^*$

The quality of the models is represented by 4 tools, namely the $R^2$, $Q^2$, Model validity and the Standard Deviation (SD) of replicates. A model that explains the data well will have a $R^2$ and $Q^2$ close to 1.0 and Model validity above 0.25. Models with low statistical significance have low $R^2$ and $Q^2$ values. It was recognized that evaluation of the $k_La^*$ results without transformation leads to a model in which the residuals do not meet the requirements of a normal distribution. This indicates, that a transformation of the $k_La^*$ is necessary to describe the results in an adequate manner. To gain a robust model, the output parameter was transformed by the power of −0.5. The model diagnostics for the process performance were $R^2$=0.95, $Q^2$=0.88, Model validity=0.82, SD=0.15, which indicates a model with high statistical significance.

Example 11.1.4—Description of Mathematical Model

The N-plot of residuals for the process output parameter $k_La^*$ value (data not shown) indicate a good fit of the experimental result with the model. The values fit close to the regression line, which means that the model transformation is adequate (the standardized residuals meet the requirements of a normal distribution). Additionally, all experimental values are inside the range ±3 standardized residuals, indicating that the measured values do not include outliers.

A coefficient plot (data not shown) indicates that all input parameters, namely stirring speed, volume and temperature, have significant influence on the process parameter $k_La^*$ value as the error bars do not cut the x-axis. Additionally, the interaction of stirrer speed and volume is significant. A contour plot of the $k_La^*$ value (data not shown) illustrates the effect of temperature, volume and stirrer speed on $k_La^*$, i.e., the higher the temperature, the lower the volume and the higher the stirrer speed, the higher the oxygen transfer over the headspace expressed as $k_La^*$.

Example 11.1.5—Results of Dedicated Run at Manufacturing Scale

The $k_La^*$ value was determined in a dedicated experiment and compared with the prediction of the model calculated by MODDE 8.02. The results of the prediction and the dedicated run are shown in Table 44. According to these results, the mathematical model was able to predict the $k_La^*$ value in an adequate manner.

TABLE 44

$k_La^*$ values (predicted and measured) of standard process conditions at manufacturing-scale (SITE A).

| Batch [-] | Volume [L] | Stirrer speed [rpm] | Temperature [° C.] | $k_La^*$ [1/h] |
|---|---|---|---|---|
| Model prediction | 606 | 200 | 38 | 0.32 |
| Result of the dedicated run | 606 | 200 | 38 | 0.25 |

Example 11.1.6—Predicted $k_La^*$ for the Process Conditions at SITE A

The $k_La^*$ for the process conditions used during campaign AT493021 at SITE A were predicted with the model calculated by MODDE 8.02. The results are shown in Table 45 with predicted $k_La^*$ values of 0.05 h$^{-1}$ to 0.69 h$^{-1}$ when constant stirring is applied. The values indicate that the process step is robust over a broad range of $k_La^*$ values resulting from different process volumes. The parameters having an influence on $k_La^*$ (and hence the oxygen transfer) should be considered for final assessment of process robustness, e.g., overall stirring time has a significant influence on the oxygen transfer.

TABLE 45

$k_La^*$ values of process conditions at manufacturing-scale (SITE A). 1) Volume exceeds the evaluated range. Extrapolation can lead to imprecise values.

| Batch [-] | Cycle [-] | Volume [L] | Stirrer speed [rpm] | Temperature [° C.] | Predicted $k_La^*$ [h$^{-1}$] |
|---|---|---|---|---|---|
| B010231 | 1 | 443 | 200 | 37 | 0.69 |
| B010231 | 2 | 466 | 200 | 37 | 0.60 |
| B010655 | 1 | 542 | 200 | 37 | 0.41 |
| B010655 | 2 | 569 | 200 | 37 | 0.37 |
| B010655 | 3 | 557 | 200 | 37 | 0.39 |
| B012307 | 1 | 1348[1)] | 200 | 37 | 0.05 |
| B013981 | 1 | 1142[1)] | 200 | 37 | 0.08 |

Example 12: Qualification Runs and Comparison of Scale-Down Model to Manufacturing-Scale at Site A

Example 12.1—Methods

Three scale-down model qualification runs (REACT065, REACT066, and REACT067) performed under standard conditions were compared with seven representative runs at manufacturing-scale. For the scale-down model qualification runs, secukinumab, INAKT.F (stored below −60° C.) originating from manufacturing-scale run B008530 (campaign AT493021, SITE A), was used. The load (INAKT.F) was thawed in a hand warm water bath (15-35° C.) before use. The steps of the full selective reduction procedure are displayed in Table 46.

TABLE 46

Description of selective reduction procedure. *calculation for addition of WFI:Vol (WFI) = (Vol (INAKT.F)*c (INAKT.F)/13.5 mg/mL) − Vol(INAKT.F); **calculation for addition of TITR3: Vol(TITR3) = (Vol(INAKT.F) + Vol(WFI) + Vol(TITR1)) * factor (TITR3), wherein factor (TITR3) = 0.05/0.95 = 0.05263 (6 mM Cysteine in reactivation solution).

| Step | Buffer | Target pH | Comment |
|---|---|---|---|
| Concentration adjustment | WFI | NA | Adjust protein concentration to 12.0-15.0 (13.5) mg/mL* |
| Check and adjust of dissolved oxygen (DO) level | NA | NA | DO > 80%, start pH-adjustment 1 |
| pH-adjustment 1 | AIN457-TITR1 (1M Tris) | 7.9-8.1 | Volume increase of approx. 5% |
| Addition of cysteine containing solution with stirring | AIN457-TITR3 (120 mM Cysteine HCl, 20 mM Na-EDTA, pH 8.0 ± 0.2) | NA | DO > 80%, start cysteine treatment; addition of cysteine solution **under stirring |
| Heating time to reaction | NA | NA | Heating from RT (18-25° C.) to |

TABLE 46-continued

Description of selective reduction procedure. *calculation for addition of WFI:Vol (WFI) = (Vol (INAKT.F)*c (INAKT.F)/ 13.5 mg/mL) − Vol(INAKT.F); **calculation for addition of TITR3: Vol(TITR3) = (Vol(INAKT.F) + Vol(WFI) + Vol(TITR1)) * factor (TITR3), wherein factor (TITR3) = 0.05/0.95 = 0.05263 (6 mM Cysteine in reactivation solution).

| Step | Buffer | Target pH | Comment |
|---|---|---|---|
| temperature with stirring | | | 37° C. under stirring in max. 1 h (75 minutes). Stirrer speed |
| Incubation | NA | NA | Incubation time: 250 min with 2 min. stirring per hour |
| Cooling time after reaction to room temperature with stirring | NA | NA | Cooling from 37° C. to RT (18-25° C.) under stirring in max. 1 h (75 minutes) |
| pH-adjustment 2 | AIN457-TITR2 (0.3M H₃PO₄) | 5.1-5.3 | Volume increase of approx. 15% |

The process parameters listed in Table 47 were applied for scale-down model qualification runs. The parameters correspond to the process conditions at manufacturing-scale (SITE A) and were scaled down appropriately.

TABLE 47

Process parameters of the selective reduction step. [1] stirring for 2 minutes each hour at 50 rpm.

| Process parameter | Unit | Target | Operating Range |
|---|---|---|---|
| Load pH | — | 8.0 | 7.9-8.1 |
| Load temperature | °C. | as is | 18-25 |
| Protein concentration before pH adjustment and TITR3 addition | mg/mL | 13.5 | 12-15 |
| Incubation temperature | °C. | 37 | 35-39 |
| Temperature after cooling | °C. | 22 | 18-25 |
| Stirrer speed during heating and cooling | rpm | 50 | 40-60 |
| Stirrer speed during incubation[1] | rpm | 0 | N/A |
| Heating time | min | 60 | ≤60 |
| Incubation time | min | 250 | 240-300 |
| Cooling time | min | 60 | ≤60 |
| pH of REACT.P | — | 5.2 | 5.1-5.3 |
| Dissolved oxygen | % | as is | >80 |
| Dilution factor with TITR3 | — | 1:20 (6 mM cysteine) | 1:20 (6 mM cysteine) |

Samples were withdrawn, pH was adjusted with 0.3 M phosphoric acid, pH 1.4 (AIN457-TITR2) to 5.2 (acceptable range 5.0-5.4) within 5 minutes, and then the samples were transferred to the analytical lab. All retained samples were frozen and stored at ≤−60° C. The qualification of the scale-down model was assessed by comparison of the product quality attributes activity by CEX and purity by CE-SDS, as previously described. The following time intervals were tested: 0, 10, 20, 30, 45, 60, 120, 240 min.

Example 12.2—Results

Figure 16:
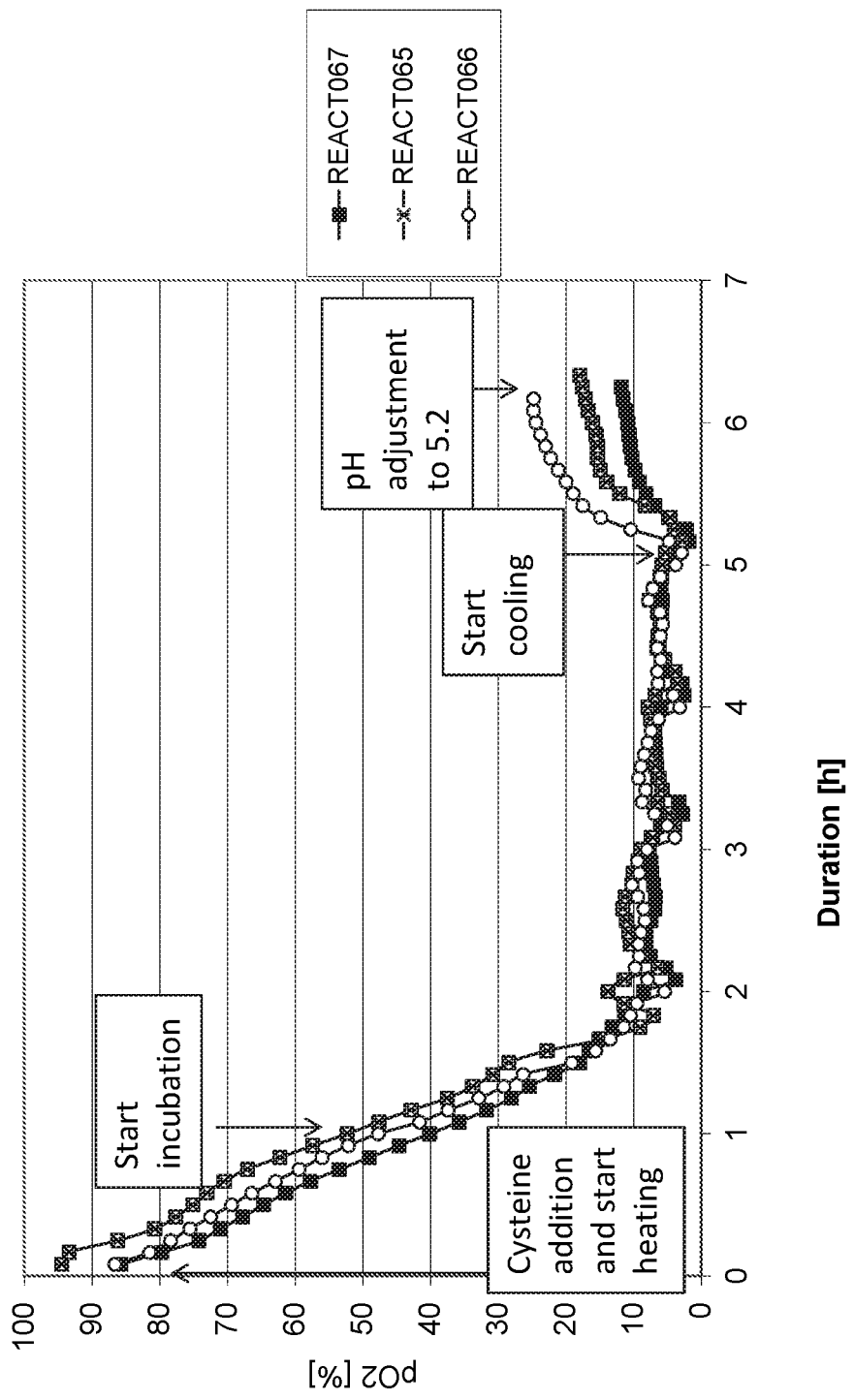
FIG. 16 shows an overlay of dissolved oxygen charts from scale-down model qualification runs, with an indication of the timing of various steps of the process (cysteine addition, heating, incubation, cooling, and pH adjustment).

Dissolved oxygen charts from three representative manufacturing-scale runs (data not shown) and the scale-down model qualification runs (FIG. 16) show the characteristic shape of the selective reduction step. The curves show that the dissolved oxygen is removed from the system by oxidation of cysteine. According to development experience, extended stirring results in higher oxygen transfer and leads to insufficient activity by CEX. Hence, the selective reduction solution is only stirred for 2-15 minutes per hour during incubation, thereby limiting the oxygen transfer into the solution and keeping the dissolved oxygen level low until the selective reduction is stopped. During the cooling phase, the oxygen level increases slightly due to the oxygen transfer into the solution by continuous mixing, while a certain amount of cysteine is oxidized, rendering it unavailable as reducing agent for the dissolved oxygen.

For the manufacturing-scale runs 3-6 of campaign AT493021 at SITE A, the activity by CEX was on average 96.3% with a standard deviation of 0.8%, while the purity by CE-SDS was on average of 92% with a standard deviation of 1%. The results of each run are displayed in Table 48, along with the predicted $k_La^*$ values derived from Table 45.

TABLE 48

Experimental results of the manufacturing-scale runs.

| Run | Activity by CEX [%] | Purity by CE-SDS [%] | Predicted $k_La^*$ [1/h] |
|---|---|---|---|
| B010231; Cycle#1 | 94.5 | 92 | 0.69 |
| B010231; Cycle#2 | 96.7 | 93 | 0.60 |
| B010655; Cycle#1 | 96.3 | 90 | 0.41 |
| B010655; Cycle#2 | 96.4 | 90 | 0.37 |
| B010655; Cycle#3 | 96.3 | 93 | 0.39 |
| B012307; Cycle#1 | 96.8 | 92 | 0.05 |
| B013981; Cycle#1 | 96.9 | 93 | 0.08 |
| Standard deviation | 0.8 | 1 | |
| Average ± 3 × Stdev | 96.3 ± 2.5 | 92 ± 4 | |

For the scale-down model qualification runs, the activity by CEX was on average value 95.0% with a standard deviation of 1.6%, while the purity by CE-SDS was on average 94% with a standard deviation of 1% (Table 49).

TABLE 49

Experimental results of the scale-down model qualification runs.

| Run | Activity by CEX [%] | Purity by CE-SDS [%] |
|---|---|---|
| Qualification run#1; REACT065 | 95.9 | 93.0 |
| Qualification run#2; REACT066 | 96.0 | 94.0 |
| Qualification run#3; REACT067 | 93.1 | 95.0 |
| Standard deviation | 1.6 | 1.0 |
| Average ± 3 × Stdev | 95.0 ± 4.9 | 94 ± 3 |

Figure 17:
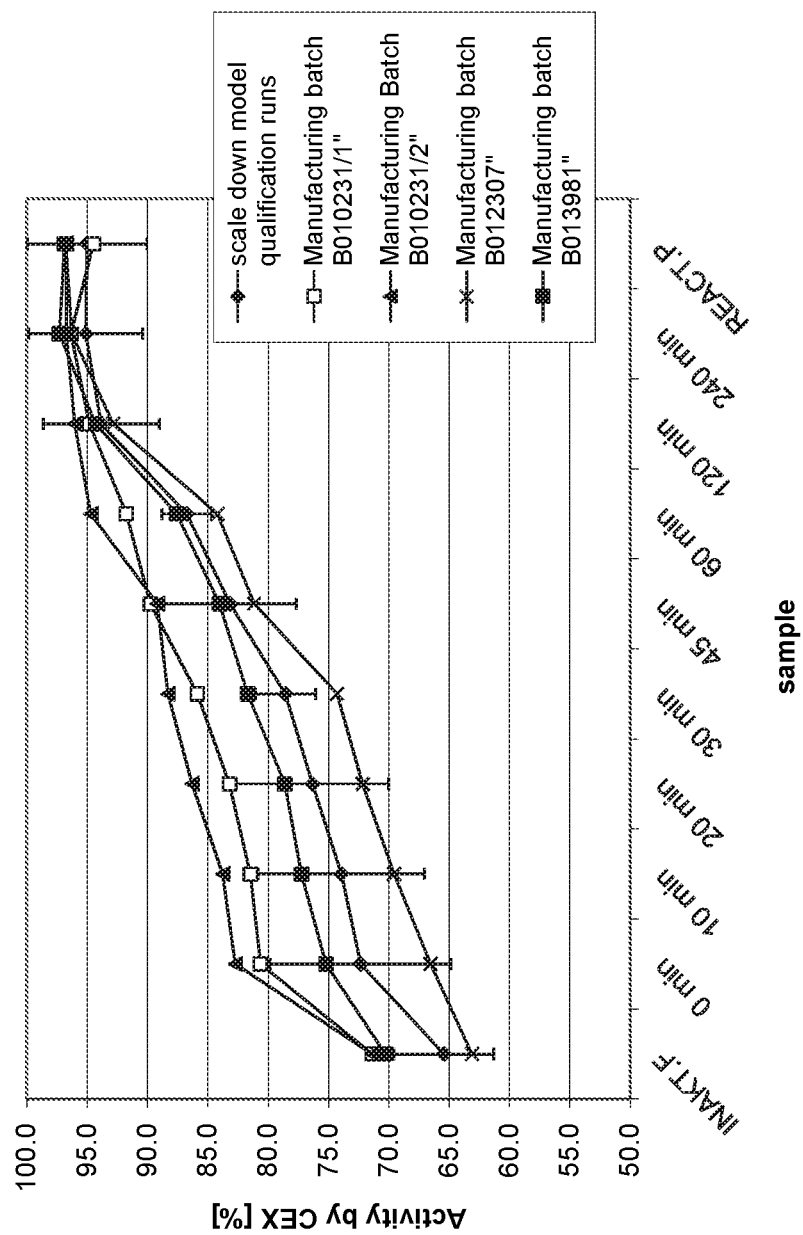
FIG. 17 shows the kinetic for activity by CEX of the manufacturing-scale runs and the scale-down model runs during selective reduction.

In addition to the assessment of product quality at the end of the selective reduction step, the kinetic for activity by CEX was also monitored and the results of the scale-down model runs (average of REACT065, 66 and 67) and manufacturing-scale at SITE A were compared. The results are shown in FIG. 17. The data obtained from the scale-down model are within the variation of the manufacturing scale, demonstrating that the kinetics at large-scale (Site A) and small-scale are comparable.

Example 13—Combined Analysis of $k_La^*$ Values from Examples 9-12

Due to the importance of the level of dissolved oxygen in the solution during the selective reduction reaction, controlled oxygen transfer from the head-space of a vessel is important for the selective reduction step. For each system, these variables can be captured as $k_La^*$ values. The $k_La^*$ is dependent on the stirrer speed, stirrer type, filling volume, temperature and surface area of the solution in contact with the headspace influenced by the individual geometry of each vessel. While $k_La^*$ will change depending on each setup, from the above experiments, it can be seen that a range of $k_La^*$ values are acceptable to ensure the quality and activity of secukinumab during the selective reduction process.

A predicted $k_La^*$ range of 0.18 10-0.37 $h^{-1}$ for the experimental conditions of the scale down studies was determined by use of the statistical model (Table 41). The $k_La^*$ value decreased as the stir speed decreased, given a set volume. Because the response surface design experimental conditions and set up in Example 9 are the same as those used with the scale-down model in Example 10, the predicted $k_La^*$ values of Table 41 can be correlated to the conditions and results in Table 28. This analysis is presented in Table 50.

The increased incubation time (relative to REACT.PT300 samples) appeared to contribute to poorer CEX values in some REACT.P runs.

As can be seen from Table 50 reactions with CEX activity greater than 90% have the following characteristics regarding the $k_La^*$ in the system during the incubation portion of the selective reduction reaction:

1) if the $k_La^*$ in the system during the incubation step of the selective reduction reaction is <0.37 $h^{-1}$, then the molar ratio of cysteine:antibody can vary between about 46:1 to about 118:1 (for both shorter and longer incubation times, e.g., about 210 to about 330 minutes, e.g., 240-300 minutes); and
2) the $k_La^*$ in the system during the incubation step of the selective reduction reaction can be as high as 0.37 $h^{-1}$ if the molar ratio of cysteine:protein is between about 56:1 to about 118:1 (for shorter incubation times, e.g., up to about 240 minute incubation) or between about 77:1 to about 118:1 (for longer incubation times, e.g., up to about 300 minute incubation).

TABLE 50

| Run | Protein (mg/ml) | Cysteine (mM) | Approx. molar ratio cysteine to protein (M/M) | kLa* ($h^{-1}$) | Spin (RPM) | Activity by CEX (%) REACT.PT300 (240 min inc.) | Purity by CE-SDS (%) REACT.PT300 (240 min inc.) | Activity by CEX (%) REACT.P (300 min inc.) | Purity by CE-SDS (%) REACT.P (300 min inc.) |
|---|---|---|---|---|---|---|---|---|---|
| REACT082 | 15.4 | 4.8 | 46.11 | 0.18 | 0 | 96.1 | 95 | 96.2 | 96 |
| REACT070 | 12.7 | 6.0 | 69.89 | 0.18 | 0 | 96.1 | 94 | 96.5 | 92 |
| REACT090 | 10.0 | 4.8 | 71.01 | 0.18 | 0 | 96.6 | 94 | 97.3 | 95 |
| REACT077 | 15.4 | 8.0 | 76.85 | 0.18 | 0 | 97.0 | 92 | 97.4 | 92 |
| REACT080 | 10.0 | 8.0 | 118.36 | 0.18 | 0 | 97.8 | 90 | 97.5 | 91 |
| REACT072 | 12.7 | 4.8 | 55.92 | 0.27 | 50 | 94.5 | 96 | 90.2 | 95 |
| REACT079 | 15.4 | 6.0 | 57.64 | 0.27 | 50 | 96.0 | 95 | 94.4 | 95 |
| REACT069 | 12.7 | 6.0 | 69.89 | 0.27 | 50 | 95.3 | 95 | 94.1 | 95 |
| REACT073 | 12.7 | 6.0 | 69.89 | 0.27 | 50 | 96.1 | 95 | 94.7 | 95 |
| REACT088 | 12.7 | 6.0 | 69.89 | 0.27 | 50 | 95.7 | 95 | 95.1 | 95 |
| REACT086 | 10.0 | 6.0 | 88.77 | 0.27 | 50 | 96.7 | 94 | 95.4 | 94 |
| REACT087 | 12.7 | 8.0 | 93.19 | 0.27 | 50 | 96.5 | 94 | 96.0 | 94 |
| REACT085 | 15.4 | 4.8 | 46.11 | 0.37 | 100 | 89.4 | 95 | 84.0 | 94 |
| REACT075 | 12.7 | 6.0 | 69.89 | 0.37 | 100 | 95.7 | 95 | 88.9 | 95 |
| REACT084 | 10.0 | 4.8 | 71.01 | 0.37 | 100 | 94.3 | 95 | 88.9 | 95 |
| REACT089 | 15.4 | 8.0 | 76.85 | 0.37 | 100 | 95.2 | 95 | 93.7 | 94 |
| REACT091 | 10.0 | 8.0 | 118.36 | 0.37 | 100 | 92.4 | 93 | 91.3 | 94 | kla* analysis for output parameter values REACT.PT300 and REACT. P. Molar ratios are rounded to the nearest whole number. The relative molecular mass of secukinumab, based on amino acid sequence, is 147,944 Daltons, which is used to calculate the molar ratio of cysteine to protein in column 4.

For experiments having a 240 minute incubation period (REACT.PT300) all reactions, except REACT085, resulted in very high selective reduction performance with adequate product quality as measured by CEX and CE-SDS (Table 50). REACT085 had a stir speed of 100 rpm, a $k_La^*$ value of 0.37 $h^{-1}$ during incubation, and a very low molar ratio of cysteine to antibody (about 46:1). The low molar ratio of cysteine to antibody, combined with high oxygen transfer into the vessel (represented by the high $k_La^*$ value), likely resulted in insufficient reactivation.

For experiments having a 300 minute incubation period (REACT.P) all reactions, except REACT085, REACT075, and REACT084 resulted in very high selective reduction performance with adequate product quality as measured by CEX and CE-SDS (Table 50). REACT085, REACT075, and REACT084 had a stir speed of 100 rpm, a $k_La^*$ value of 0.37 $h^{-1}$ during incubation, and a low-medium molar ratio of cysteine to antibody (about 46:1 and about 71:1). The low-medium molar ratio of cysteine to antibody, combined with high oxygen transfer into the vessel (represented by the high $k_La^*$ value), likely resulted in insufficient reactivation.

Of course, the $k_La^*$ during the heating and cooling phase can be much higher than the $k_La^*$ during the incubation phase, e.g., Table 54 shows a $k_La^*$ as high as 0.69 $h^{-1}$ can be applied during the heating/cooling phase and still produce high quality product.

Example 9 (process characterization studies) examined the output parameters activity by CEX and purity by CE-SDS using a scale-down model that applied constant stirring during the incubation phase. Example 10 examined $k_La^*$ values of the scale-down model that also applied constant stirring. Example 11 examined the $k_La^*$ values when using continuous stirring at manufacturing-scale. During actual manufacturing, continuous stirring is only applied during the heating and cooling phases of the selective reduction reaction, while intermittent stirring (e.g., 2-15 minutes per hour) is applied during the incubation phases of the selective reduction reaction. Therefore, during manufacturing, the $k_La^*$ of the system during the incubation phases of the selective reduction reaction step will be much lower than the $k_La^*$ values observed in Examples 10 and 11. Nevertheless, from the combined results of Examples 9-11, it can be seen that the entire selective reduction step (i.e., heating phase, incubation phase, and cooling phase) can be generally performed using a $k_L a^*$ of <0.37 h$^{-1}$, including about 240 to about 300 minute incubation phase, if the molar ratio of cysteine:antibody is between about 46:1 to about 118:1.

The Worst/Best case experiments of Example 9 were performed using the same qualified scale-down model, using a molar ratio of cysteine:antibody of about 66:1 with negligible stirring (i.e., 2 minutes per hour) during the incubation phase ($k_L a^*$ of <0.18 h$^{-1}$). Since reactions incubated for 210 to 330 minutes in the Worst/Best case experiments of Example 9 all produced high quality product, it is expected that the incubation time can be expanded to about 210-about 330 minutes if the $k_L a^*$ is low and the molar ratio of cysteine:antibody is medium (e.g., about 66:1).

Example 14—Preferred Selective Reduction Process Parameters and Procedures

The preferred process parameters of the selective reduction step are listed in Table 51. The molar ratio of cysteine:antibody for the set point is about 66:1, with a suggested operating range of about 54:1 to about 83:1, and a proven acceptable range of about 46:1 to about 118:1.

TABLE LLLLL

Selective reduction- list of process parameters.

| Parameter | Set-point/ Target | Suggested Operating Range | Proven Acceptable Range (PAR) |
|---|---|---|---|
| Incubation temperature [° C.] | 37 | 35-39 | 32-42 |
| Protein concentration before pH adjustment and addition of TITR3 buffer [g/L] | 13.5 | 12-15 | 10.0-15.4 |
| Process pH [-] | 8 | 7.9-8.1 | 7.8-8.2 |
| Dissolved oxygen (DO) at reactivation start [%] | as is | ≥80 | ≥60 |
| Dilution factor by AIN457-TITR3 addition | 1:20 (6.0 mM cysteine, 1.0 mM EDTA) | 1:18-1:22 (5.5-6.7 mM cysteine, 0.9-1.1 mM EDTA) | 1:15-1:25 (4.8-8.0 mM cysteine, 1.3-0.8 mM EDTA) |
| Approx. molar ratio cysteine:antibody [M/M] | 65.75:1 (about 66:1) | 54.24:1-82.60:1 (about 54:1 to about 83:1) | 46.11:1-118.36:1 (about 46:1 to about 118:1) |
| Incubation time for reactivation including stirring [min] | 250 | 240-300 | 210-330 |
| pH adjustment after temperature decrease [-] | 5.2 | 5.1-5.3 | |
| Heating time including stirring [min] | 60 | ≤75 | ≤90 |
| Stirring time during incubation [min/hour] | 2 | ≤5 | ≤15 |
| Stir speed during incubation [rpm] | 75 | 65-85 | 65-85 |
| Cooling time including stirring [min] | 60 | ≤75 | ≤90 |

The individual steps of the selective reduction procedure are displayed in Table 52. First, the protein concentration of the starting material is adjusted by addition of WFI to a target concentration of 13.5 mg/mL. Next, the pH is adjusted to 8.0 by addition of 1 M Tris. The dO$_2$ is checked and adjusted (e.g., to ≥60%), e.g., by further mixing, submerge aeration, etc., if the operating range is not met. The reaction is started by adding cysteine to 6 mM and thereafter the solution is heated (over about an hour) to incubation temperature (about 37° C.). The solution is incubated for about 250 minutes with about 2 minutes stirring per hour to limit oxygen transfer from headspace into solution during incubation time. Finally, the solution is cooled to room temperature (over about an hour) and the pH is adjusted to about 5.2, e.g., with 0.3 M ortho-phosphoric acid to stop the reaction.

TABLE 52

Description of selective reduction procedure.*calculation for addition of WFI:Vol (WFI) = (Vol (INAKT.F)*c (INAKT.F)/13.5 mg/mL) − Vol(INAKT.F); **calculation for addition of TITR3: Vol(TITR3) = (Vol(INAKT.F) + Vol(WFI) + Vol(TITR1)) * factor (TITR3), wherein factor (TITR3) = 0.05/0.95 = 0.05263 (6 mM Cysteine in reactivation solution).

| Step | Buffer | Target pH | Comment |
|---|---|---|---|
| Concentration adjustment | WFI | NA | Adjust protein concentration to 12.0-15.0 (13.5) mg/mL* |
| Check and adjust of dissolved oxygen (DO) level | NA | NA | DO > 80%, start pH-adjustment 1 |
| pH-adjustment 1 | AIN457-TITR1 (1M Tris) | 7.9-8.1 | Volume increase of approx. 5% |
| Addition of cysteine containing solution with stirring | AIN457-TITR3 (120 mM Cysteine HCl, 20 mM Na-EDTA, pH 8.0 ± 0.2) | NA | DO > 80%, start cysteine treatment; addition of cysteine solution **under stirring |
| Heating time to reaction temperature with stirring | NA | NA | Heating from RT (18-25° C.) to 37° C. under stirring in max. 1 h (75 minutes). Stirrer speed |
| Incubation | NA | NA | Incubation time: 250 min with 2 min. stirring per hour |
| Cooling time after reaction to room temperature with stirring | NA | NA | Cooling from 37° C. to RT (18-25° C.) under stirring in max. 1 h (75 minutes) |
| pH-adjustment 2 | AIN457-TITR2 (0.3M H$_3$PO$_4$) | 5.1-5.3 | Volume increase of approx. 15% |

What is claimed is:

1. A method for selectively reducing CysL97 in a preparation of secukinumab antibody that have been recombinantly produced by mammalian cells comprising:
   a) contacting the preparation with at least one reducing agent to form a reducing mixture, wherein the at least one reducing agent is a thiol-containing reducing agent having a standard oxidation-reduction potential, E°, of about −0.20 V-about −0.23 V at pH 7.0, as measured by thiol-disulfide exchange, and wherein the molar ratio of reducing agent to antibody in the reducing mixture is between about 46:1-about 118:1; and
   b) incubating the reducing mixture at a temperature of between about 32° C. to about 42° C. while maintaining a volumetric oxygen mass-transfer coefficient ($k_La^*$) <0.37 h$^{-1}$;
wherein prior to step a) the initial percent oxygen saturation in the preparation is at least 60%, as measured using an oxygen probe calibrated at 25° C.

2. The method according to claim 1, wherein the at least one reducing agent is cysteine, and wherein the molar ratio of cysteine:antibody in the reducing mixture is between about 46:1-about 118:1.

3. The method according to claim 2, wherein the $k_La^*$ is:
   a. <0.37 h$^{-1}$, and wherein the molar ratio of cysteine to secukinumab antibody in the reducing mixture is between about 56:1-about 118:1, and wherein the reducing mixture is incubated according to step b) for up to 240 minutes;
   b. <0.37 h$^{-1}$, and wherein the molar ratio of cysteine to secukinumab antibody in the reducing mixture is between about 77:1-about 118:1, and wherein the reducing mixture is incubated according to step b) for up to 300 minutes;
   c. <0.37 h$^{-1}$, and wherein the molar ratio of cysteine to secukinumab antibody in the reducing mixture is between about 46:1-about 118:1;
   d. <0.37 h$^{-1}$, and wherein the molar ratio of cysteine to secukinumab antibody in the reducing mixture is between about 54:1-about 82:1; or
   e. <0.27 h$^{-1}$.

4. The method according to claim 3, wherein the molar ratio of cysteine to secukinumab antibody in the reducing mixture is about 66:1.

5. The method according to claim 3, wherein the concentration of cysteine in the reducing mixture is about 4.0 mM-about 8.0 mM.

6. The method according to claim 2, wherein prior to step a), the concentration of secukinumab antibody in the preparation is about 4 mg/ml to about 19.4 mg/ml.

7. The method according to claim 6, wherein prior to step a) the pH of the preparation is about 7.3 to about 8.5.

8. The method according to claim 7, wherein prior to step a) the initial percent oxygen saturation in the preparation is at least 80%, as measured using an oxygen probe calibrated at 25° C.

9. The method according to claim 2, wherein between step a) and step b), the reducing mixture is heated to a temperature that is between about 32° C. to 42° C.

10. The method according to claim 9, wherein the reducing mixture is heated for about 45 to about 90 minutes.

11. The method according to claim 9, wherein the $k_La^*$ during heating is ≤0.69 h$^{-1}$.

12. The method according to claim 2, wherein between step a) and step b), the reducing mixture is heated to a temperature between about 32° C.-about 42° C. for about 45-about 90 minutes, wherein the $k_La^*$ during heating is ≤0.69 h$^{-1}$.

13. The method according to claim 2, wherein during step b) the reducing mixture is stirred for ≤15 minutes per hour.

14. The method according to claim 2, wherein the activity of secukinumab antibody in the preparation increases by at least 10% within about 60 minutes following step b), as measured by cystamine-cation exchange chromatography (cystamine-CEX).

15. The method according to claim 2, further comprising:
   c) after step b), cooling the reducing mixture to room temperature.

16. The method according to claim 15, wherein the mixture is cooled according to step c) for about 45 to about 90 minutes.

17. The method according to claim 15, wherein the $k_La^*$ during step c) is ≤0.69 h$^{-1}$.

18. The method according to claim 2, further comprising:
   c) adjusting the pH of the mixture resultant from step b) to between about 5.1 to about 5.3.

19. The method according to claim 18, wherein adjusting step c) comprises adding o-phosphoric acid to the mixture resultant from step b).

20. The method according to claim 18, wherein at least 90% of the secukinumab antibody in the mixture resultant from step c) is intact, as measured by CE-SDS.

21. The method according to claim 18, wherein at least 90% of secukinumab antibody in the mixture resultant from step c) is active, as measured by cystamine-CEX.

22. The method according to claim 2, wherein the reducing mixture further comprises about 0.8 mM to about 1.3 mM EDTA.

23. The method according to claim 2, wherein an oxidized form of the reducing reagent is not added to the reducing mixture.

24. The method according to claim 2, wherein a denaturant is not added to the reducing mixture.

25. The method according to claim 1, wherein the reducing mixture is incubated according to step b) for about 210 to about 420 minutes.

* * * * *

SEQUENCE LISTING

<160> NUMBER OF SEQ ID NOS: 15

<210> SEQ ID NO 1
<211> LENGTH: 5
<212> TYPE: PRT

-continued

```
<213> ORGANISM: artificial
<220> FEATURE:
<223> OTHER INFORMATION: CDR1 = hypervariable region 1 of heavy chain of
      AIN457

<400> SEQUENCE: 1

Asn Tyr Trp Met Asn
1               5

<210> SEQ ID NO 2
<211> LENGTH: 17
<212> TYPE: PRT
<213> ORGANISM: ARTIFICIAL
<220> FEATURE:
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
<211> LENGTH: 12
<212> TYPE: PRT
<213> ORGANISM: ARTIFICIAL
<220> FEATURE:
<223> OTHER INFORMATION: CDR1' = hypervariable region 1 of light chain
      of AIN457

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: ARTIFICIAL
<220> FEATURE:
<223> OTHER INFORMATION: CDR3' = hypervariable region 3 of light chain
      AIN457
```

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7

```
gag gtg cag ttg gtg gag tct ggg gga ggc ttg gtc cag cct ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt aac tat     96
Ser Leu Arg Leu Ser Cys Ala Ala Ser Gly Phe Thr Phe Ser Asn Tyr
            20                  25                  30 tgg atg aac tgg gtc cgc cag gct cca ggg aaa ggg ctg gag tgg gtg    144
Trp Met Asn Trp Val Arg Gln Ala Pro Gly Lys Gly Leu Glu Trp Val
        35                  40                  45 gcc gcc ata aac caa gat gga agt gag aaa tac tat gtg ggc tct gtg    192
Ala Ala Ile Asn Gln Asp Gly Ser Glu Lys Tyr Tyr Val Gly Ser Val
    50                  55                  60 aag ggc cga ttc acc atc tcc aga gac aac gcc aag aac tca ctg tat    240
Lys Gly Arg Phe Thr Ile Ser Arg Asp Asn Ala Lys Asn Ser Leu Tyr
65                  70                  75                  80 ctg caa atg aac agc ctg aga gtc gag gac acg gct gtg tat tac tgt    288
Leu Gln Met Asn Ser Leu Arg Val Glu Asp Thr Ala Val Tyr Tyr Cys
                85                  90                  95 gtg agg gac tat tac gat att ttg acc gat tat tac atc cac tat tgg    336
Val Arg Asp Tyr Tyr Asp Ile Leu Thr Asp Tyr Tyr Ile His Tyr Trp
            100                 105                 110 tac ttc gat ctc tgg ggc cgt ggc acc ctg gtc act gtc tcc tca        381
Tyr Phe Asp Leu Trp Gly Arg Gly Thr Leu Val Thr Val Ser Ser
        115                 120                 125
```

<210> SEQ ID NO 8
<211> LENGTH: 127
<212> TYPE: PRT
<213> ORGANISM: HOMO SAPIENS

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9

```
gaa att gtg ttg acg cag tct cca ggc acc ctg tct ttg tct cca ggg    48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc    96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc   144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt   192
Ile Tyr Gly Ala Ser Ser Arg Ala Thr Gly Ile Pro Asp Arg Phe Ser
        50                  55                  60 ggc agt ggg tct ggg aca gac ttc act ctc acc atc agc aga ctg gag   240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg   288
Pro Glu Asp Phe Ala Val Tyr Tyr Cys Gln Gln Tyr Gly Ser Ser Pro
                85                  90                  95 tgc acc ttc ggc caa ggg aca cga ctg gag att aaa cga               327
Cys Thr Phe Gly Gln Gly Thr Arg Leu Glu Ile Lys Arg
            100                 105
```

<210> SEQ ID NO 10
<211> LENGTH: 109
<212> TYPE: PRT
<213> ORGANISM: HOMO SAPIENS

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105
```

<210> SEQ ID NO 11
<211> LENGTH: 10
<212> TYPE: PRT
<213> ORGANISM: artificial
<220> FEATURE:
<223> OTHER INFORMATION: CDR1-x = hypervariable domain x of heavy chain of AIN457

<400> SEQUENCE: 11

Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 215
<212> TYPE: PRT
<213> ORGANISM: homo sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

```
Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 15
<211> LENGTH: 457
<212> TYPE: PRT
<213> ORGANISM: homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Ile His Tyr Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350
```

-continued

```
Pro Arg Glu Pro Gln Val Tyr Thr Leu Pro Pro Ser Arg Glu Glu Met
    355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```